US006727300B2

(12) United States Patent
Sassi

(10) Patent No.: US 6,727,300 B2
(45) Date of Patent: Apr. 27, 2004

(54) POLYMERIC ARTICLES CONTAINING HINDERED AMINE LIGHT STABILIZERS BASED ON MULTI-FUNCTIONAL CARBONYL COMPOUNDS

(75) Inventor: Thomas P. Sassi, Stamford, CT (US)

(73) Assignee: Cytec Technology Corp., Wilmington, DE (US)

( * ) Notice: Subject to any disclaimer, the term of this patent is extended or adjusted under 35 U.S.C. 154(b) by 338 days.

(21) Appl. No.: 10/087,266

(22) Filed: Oct. 25, 2001

(65) Prior Publication Data

US 2002/0161075 A1 Oct. 31, 2002

Related U.S. Application Data

(63) Continuation-in-part of application No. 09/704,840, filed on Nov. 3, 2000.

(51) Int. Cl.$^7$ ............................................. C08K 5/3435
(52) U.S. Cl. .................. 524/103; 524/99; 546/188; 546/242; 546/244; 528/289
(58) Field of Search .................. 524/99, 103; 546/188, 546/242, 244; 528/289

(56) References Cited

U.S. PATENT DOCUMENTS

| 3,043,709 A | 7/1962 | Amborski .................. 428/216 |
| 3,309,220 A | 3/1967 | Osteen ....................... 427/160 |
| 3,487,505 A | 1/1970 | Chisholm et al. ........ 425/133.5 |
| 3,557,265 A | 1/1971 | Chisholm et al. ........... 264/46.1 |
| 3,640,928 A | 2/1972 | Murayama et al. ............ 45/60 |
| 3,840,494 A | 10/1974 | Murayama et al. ............ 45/60 |
| 4,021,432 A | 5/1977 | Holt et al. ............. 260/293.64 |
| 4,049,647 A | 9/1977 | Holt et al. .................. 542/426 |
| 4,086,204 A | 4/1978 | Cassandrini et al. ....... 260/45.8 |
| RE30,385 E | 8/1980 | Hillard et al. ............. 260/45.8 |
| 4,223,412 A | 9/1980 | Aoyagi et al. ................... 3/1.9 |
| 4,233,412 A | 11/1980 | Rody et al. .................. 525/167 |
| 4,265,805 A | 5/1981 | Thomas ..................... 260/45.8 |
| 4,314,933 A | 2/1982 | Berner .................... 260/45.75 N |
| 4,325,863 A | 4/1982 | Hinsken et al. ............. 624/111 |
| 4,331,586 A | 5/1982 | Hardy ......................... 525/186 |
| 4,338,244 A | 7/1982 | Hinsken et al. ............. 524/109 |
| 4,344,876 A | 8/1982 | Berner ......................... 524/91 |
| 4,353,965 A | 10/1982 | Olson et al. ................ 428/412 |
| 4,356,307 A | 10/1982 | Kelkenberg et al. ........ 546/200 |
| RE31,342 E | 8/1983 | Holt et al. .................. 542/427 |
| 4,426,471 A | 1/1984 | Berner ......................... 524/91 |
| 4,426,472 A | 1/1984 | Berner ......................... 524/99 |
| 4,481,664 A | 11/1984 | Linger et al. .................... 382/8 |
| 4,540,623 A | 9/1985 | Im et al. ...................... 428/220 |
| 4,619,956 A | 10/1986 | Susi ............................. 524/87 |
| 4,668,588 A | 5/1987 | Kishima ..................... 428/412 |
| 4,722,806 A | 2/1988 | Lai et al. .................... 252/403 |
| 4,740,542 A | 4/1988 | Susi ............................. 524/87 |
| 4,937,026 A | 6/1990 | Goossens et al. ............ 264/129 |
| 4,940,742 A | 7/1990 | Aumueller et al. ........... 524/93 |
| 4,960,863 A | 10/1990 | Rosenquist ................. 528/480 |
| 4,992,322 A | 2/1991 | Curry et al. ................. 428/215 |
| 5,017,702 A | 5/1991 | Aumueller et al. ............ 546/99 |
| 5,071,981 A | 12/1991 | Son et al. .................... 544/198 |
| 5,106,972 A | 4/1992 | Burdeska et al. ............ 544/219 |
| 5,175,312 A | 12/1992 | Dubs et al. .................. 549/307 |
| 5,216,052 A | 6/1993 | Nesvadba et al. ........... 524/108 |
| 5,252,643 A | 10/1993 | Nesvadba .................... 524/111 |
| 5,288,788 A | 2/1994 | Shieh et al. ................. 524/495 |
| 5,300,678 A | 4/1994 | Merger et al. ............... 560/157 |
| 5,445,872 A | 8/1995 | Suhadolnik et al. ......... 428/215 |
| 5,461,151 A | 10/1995 | Waterman .................... 544/216 |
| 5,574,162 A | 11/1996 | Galbo et al. ................. 546/188 |
| 5,721,298 A | 2/1998 | Waterman et al. ........... 524/100 |
| 5,726,309 A | 3/1998 | Stevenson et al. ........... 544/216 |
| 6,271,377 B1 | 8/2001 | Galbo et al. .................. 546/14 |

FOREIGN PATENT DOCUMENTS

| DE | 3922496 | 1/1991 |
| DE | 4316611 A | 11/1993 |
| DE | 4316622 A | 11/1993 |
| DE | 4316876 | 11/1993 |
| EP | 309400 | 3/1989 |
| EP | 309401 | 3/1989 |
| EP | 309402 | 3/1989 |
| EP | 434608 | 6/1991 |
| EP | 589839 | 3/1994 |
| EP | 591102 | 4/1994 |
| GB | 2269819 A | 2/1994 |
| GB | 2290745 | 6/1995 |

OTHER PUBLICATIONS

Dixit, A.N. et al., "Facile Acid Catalyzed Ring Cleavage of N–acylated Lactams," Tetrahedron Letters 35:33, 6133–1634, 1994.

Duong, T. et al., "Central Nervous System Active Compounds. I The Synthesis of Some Caprolactam Derivatives Substituted at N1, C2 and C3," Aust. J. Chem. 29:2651–2665, 1976.

Effenberger, F. et al., "Darstellung von Aminosauren aus Halogencarbonsaure–alkyl–estem mit Alkalimetallcyanaten," Chem Ber. 114:173–189, 1981.

Iwakura, Y. et al., "The Syntheses and Some Reactions of ω–isocyanatoalkanecarboxylic Acid Chlorides and Isocyanatobenzoyl Chlorides," J. Org. Chem. 31:142–146. 1966.

Taub, B. et al., "Synthesis of N–Carboalkoxy–ε–Aminocaproic Acid Esters," J. Chem. Eng. Data 9:106, 1964.

Ullmann's Encyclopedia of Industrial Chemistry, 5$^{th}$ Edition, vol. A18, pp. 368–426. VCH, Weinheim, 1991.

Ullmann's Encyclopedia of Industrial Chemistry, 5$^{th}$ Edition, vol. A18, pp. 429–471, VCH, Weinheim, 1991.

Ullmann's Encyclopedia of Industrial Chemistry, 5$^{th}$ Edition, vol. A18, pp. 451–453.

Ullmann's Encyclopedia of Industrial Chemistry, 5$^{th}$ Edition, vol. A18, p. 469, VCH Verlagsgesellschaft, Weinheim, 1991.

Ullmann's Encyclopedia of Industrial Chemistry, 5$^{th}$ Edition, vol. A18, pp. 491–500.

Primary Examiner—Peter Szekely
(74) Attorney, Agent, or Firm—James A. Jubinsky; Claire M. Schultz; Fran Wasserman

(57) ABSTRACT

Polymeric articles containing at least one polymeric material and a sufficient amount of at least one novel hindered amine light stabilizers to inhibit at least one of photo- or thermal degradation. The hindered amine light stabilizer may be a monomeric or an oligomeric hindered amine light stabilizer.

13 Claims, No Drawings

POLYMERIC ARTICLES CONTAINING HINDERED AMINE LIGHT STABILIZERS BASED ON MULTI-FUNCTIONAL CARBONYL COMPOUNDS

This application is a continuation-in-part of U.S. application Ser. No. 09/704,840, filed Nov. 3, 2000.

FIELD OF THE INVENTION

This invention relates generally to novel hindered amine light stabilizers (HALS) and their use as a protectant against ultraviolet radiation or light ("UV light"). Also included are concentrates and articles including such stabilizers, and methods of making all of the above.

BACKGROUND

It is well known that ultraviolet ("UV") light or radiation, especially sunlight, can cause degradation of a variety of materials, especially polymeric materials. Often this results in embrittlement or yellowing of the materials, which may be in the form of molded articles, extruded articles, films, tapes, coatings, or the like. However, this degradation can be inhibited by the incorporation of light stabilizers in, or on, the polymeric articles. The most commonly used stabilizers are UV-absorbers, hindered amine light stabilizers ("HALS"), and phenolic and non-phenolic antioxidants.

HALS scavenge free radicals formed in polymeric material when the material is exposed to UV light. The functional component of the HALS molecule is typically the 2,2,6,6-tetraalkylpiperidine moiety. Typically, the 2,2,6,6-tetraalkylpiperidine moiety is anchored to a carbonyl or melamine functional group (See, e.g., U.S. Pat. Nos. 4,331,586; 3,840,494; Re. 31,342; Re. 30,385; 3,640,928; 4,086,204; 4,265,805). Anchoring the 2,2,6,6-tetraalkylpiperidine moiety to a carbonyl or melamine functional group typically lowers the volatility and extractability of a stabilizer. Low volatility is an important characteristic of light stabilizers in applications where high temperatures are encountered, which occurs frequently in the processing of thermoplastics and in the curing of thermoset resins and coatings. Often, high temperatures are also present in the end-use applications for the stabilized material. Low volatility helps prevent loss of the stabilizer during processing, curing, and high temperature end uses. Typically, HALS molecules containing the 2,2,6,6-tetraalkylpiperidine group anchored to a carbonyl group are made by reacting a 2,2,6,6-tetraalkylpiperidin-4-ol or 4-amino-2,2,6,6-tetramethylpiperidine with a carboxylic acid chloride or ester.

U.S. Pat. Nos. Re. 31,342, 4,021,432 and 4,049,647 disclose a class of 1- and 4-substituted piperidines that are stabilizers for organic materials. The stabilizers are produced by reacting the corresponding 1-substituted piperidinols with acid chlorides, or the corresponding 4-substituted piperidines, with a compound introducing a residue into the 1-position of the piperidine moiety.

U.S. Pat. No. 3,840,494 discloses a polymer composition stabilized against photo- and thermal deterioration by incorporating therein acid esters of 4-piperidinol derivatives in an amount sufficient to prevent such deterioration. The acid esters of the 4-piperidinol derivatives are prepared by reacting the 4-piperidinol derivative with a carboxylate ester in xylene with sodium hydroxide. For example, the reaction of 4-hydroxy-2,2,6,6-tetramethylpiperidine with ethyl benzoate produces 4-benzoyloxy-2,2,6,6-tetramethylpiperidine.

Similarly, the 2,2,6,6-tetramethylpiperidin-4-ol can be reacted with diesters or diacid chlorides to produce diester-HALS. Also, the 2,2,6,6-tetramethylpiperidin-4-ol can be reacted with a diisocyanate to produce a diurethane-HALS. However, the relatively high cost of diisocyanates makes them less practical than diesters when preparing HALS.

Compounds which have an ester functionality at one terminus of a hydrocarbon chain and a urethane functionality at the other terminus of the hydrocarbon chain (alkoxycarbonylamino alkanoates) are known for various other uses other than light stabilization and can be prepared by a variety of synthetic schemes (See, e.g., Effenberger, F.; Drauz, K.; Foerster, S.; Mueller, W., *Chem. Ber.*, 114(1), 173–89; Dixit, A.; Tandel, S.; Rajappa, S.; *Tett. Lett.*; 35(33), 6133–4, Duong, et al., *Aust. J. Chem.*, 29, 2651–61, 1976; Iwaka et al., *J. Org. Chem.*, 31, 142–46, 1966; Taub; Hino; *J. Chem. Eng. Data*, 9, 106, 1964; U.S. Pat. No. 5,300,678 to Merger et al.).

U.S. Pat. No. 5,574,162 discloses 1-hydrocarbyloxy substituted HALS, which also contain reactive functional groups that chemically attach to selected polymer substrates by condensation reactions.

Oligomeric HALS are also known. For example, TINUVIN 622 is a commercially available oligomeric HALS produced by Ciba Specialty Chemicals Inc. of Hawthorne, N.Y. TINUVIN 622 can be produced by the reaction of dimethyl succinate with N-(2-hydroxyethyl)-2,2,6,6-tetramethyl-4-piperidinol. U.S. Pat. No. 4,223,412 discloses condensation and addition polymers wherein the recurrent molecular unit contains a polyalkylpiperidine radical that are useful as light stabilizers for plastics. In one embodiment the copolymer is formed by copolymerization or copolycondensation of polyalkylpiperidine containing monomers with polyalkylpiperidine free monomers such as caprolactam.

U.S. Pat. No. 6,271,377 discloses HALS which are substituted on the N-atom by N-alkyloxy moieties containing one to three hydroxyl groups.

U.S. Pat. No. 4,331,586 to Hardy discloses oligomers that contain at least one piperidyl moiety in the repeating unit for use as light stabilizers. While providing protection for polymeric materials, such as polypropylene, polymeric films containing the disclosed oligomeric HALS became brittle after exposure to UV light for about 1,700 hours.

HALS compounds may be used individually or in combination with other light stabilizers to inhibit photodegradation of polymers. For example, UV light absorbers, such as benzotriazoles and benzophenones, were initially used to stabilize polymeric materials and to prevent degradation of such materials from exposure to UV light. Later, it was discovered that HALS compounds were more effective than UV light absorbers alone, and thus, UV light absorbers are presently used in combination with at least one HALS compound in most conventional applications (See, e.g., U.S. Pat. Nos. 4,740,542; 4,619,956; 5,461,151; 5,721,298). Similarly, HALS compounds are often employed in combination with other stabilizers, such as antioxidants (See, e.g., U.S. Pat. No. 4,722,806). Combining the HALS with another stabilizer may provide a polymeric material with better resistance to weathering.

U.S. Pat. No. 4,619,956 discloses a method of stabilizing a polymer film, coating, or molded article against the action of light, moisture and oxygen by incorporating a HALS compound and a tris-aryl-s-triazine UV light absorber into a polymer. Preferably, the HALS compound is a 2,2,6,6-tetraalkylpiperidine compound, salt, or metal complex, and the UV light absorber is a tris-aryl-2-triazine of formula

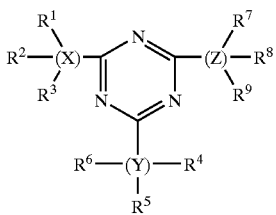

where X, Y, and Z are each aromatic carbocyclic groups, and at least one of the aromatic groups has a hydroxy group ortho to the point of attachment to the triazine ring. Each of $R^1$ to $R^9$ is hydrogen, hydroxy, alkyl, alkoxy, sulfonic, carboxy, halo, haloalkyl, or acylamino. Each of the UV light absorbers and HALS compound are used in an amount of from about 0.01 to 5 percent by weight, but only formulations having equal amounts of UV light absorber and HALS compound are exemplified. The compositions are effective in stabilizing the polymeric material, which does not begin to lose gloss or turn yellow until after about 1,000 to 2,400 hours of exposure to UV light.

Thus, a need still remains for improved articles, and compositions and methods of use and preparation thereof, that stabilize polymeric materials and provide protection from exposure to UV light for extended periods of time. The present invention provides such compositions, articles and methods.

SUMMARY OF THE INVENTION

The invention relates to polymeric articles that include at least one polymeric material and a sufficient amount of at least one compound of formula I, II, or III to inhibit at least one of photo- or thermal degradation. The compound of formula (I) is:

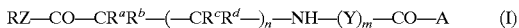

wherein n is an integer from 1 to 15, m is either 0 or 1; $R^a$, $R^b$, $R^c$, and $R^d$ are each a hydrogen or a hydrocarbyl group; Y is $CO-(CR^eR^f)_p$, wherein $R^e$ and $R^f$ are each a hydrogen or hydrocarbyl group and p is zero or an integer from 1 to 20 or $CO-C_6H_4-$, wherein the substitution pattern on the phenylene group is an ortho, meta, or para substitution pattern and one or more of the hydrogens of the phenylene group may be substituted by a hydrocarbyl group or a functional group; Z is —O— or —NG—, wherein G is H, $C_1-C_{12}$ alkyl or the radical R; and wherein R is

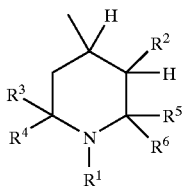

wherein $R^1$ is hydrogen, $C_1-C_{18}$, alkyl, O, OH, $CH_2CN$, $C_1-C_{18}$, alkoxy, $C_1-C_{18}$ hydroxyalkoxy, $C_5-C_{12}$ cycloalkoxy, $C_5-C_{12}$ hydrocycloalkoxy, $C_3-C_6$ alkenyl, $C_1-C_{18}$ alkynyl, $C_7-C_9$ phenylalkyl, unsubstituted or substituted on the phenyl with 1, 2 or 3 $C_1-C_4$ alkyls, or an aliphatic $C_1-C_8$ acyl; $R^2$ is hydrogen, $C_1-C_{18}$ alkyl, or benzyl; $R^3$, $R^4$, $R^5$, and $R^6$ are each a hydrogen, $C_1-C_8$ alkyl, benzyl or phenethyl, or two geminal R moieties, which together with the carbon to which they are attached form a $C_5-C_{10}$ cycloalkyl; and A is either ZR or a hydrocarbyl group. The compound of formula II is:

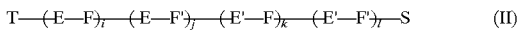

wherein i, j, k, and l are integers from about 0 to 300 and the sum of i, j, k, and l is greater than 2, wherein E—F is

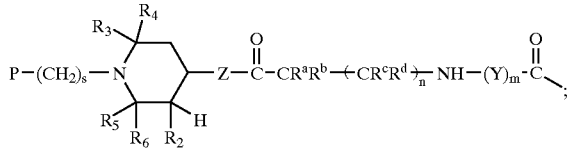

E—F' is

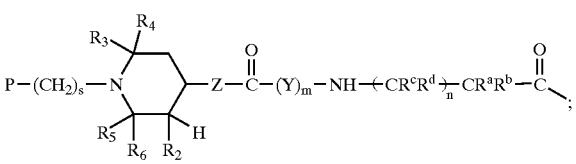

E'—F is

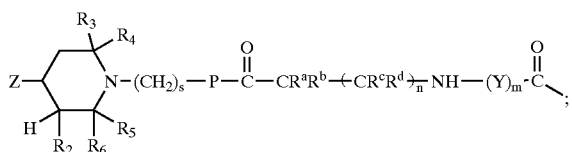

E'—F' is

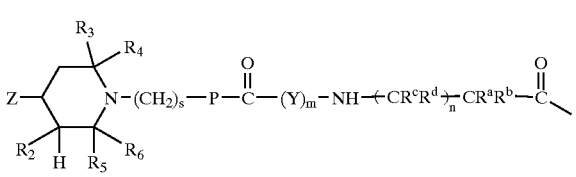

S is a hydrogen, or a unit derived from a piperidin-4-ol or a 4-aminopiperidine moiety having the structure

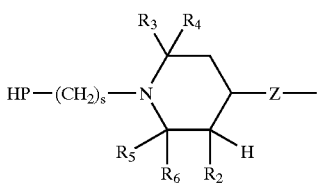

or

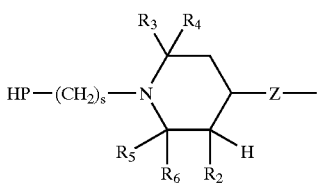

and T is a hydrogen or a unit derived from a multi-functional carbonyl compound having the structure

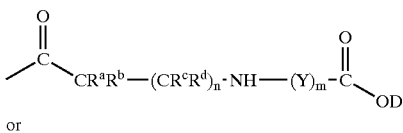

or

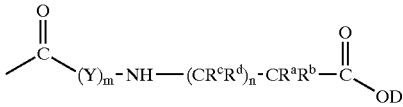

wherein D is a hydrocarbyl group, n is an integer from 1 to 15, m is either 0 or 1, s is 0 or an integer from 1 to 10; $R^a$, $R^b$, $R^c$, and $R^d$, are each a hydrogen or a hydrocarbyl group; Y is CO—$(CR^eR^f)_p$, wherein $R^e$ and $R^f$ are each a hydrogen or hydrocarbyl group and p is an integer from 0 to 20 or CO—$C_6H_4$—, wherein the substitution pattern on the phenylene group is an ortho, meta, or para substitution pattern, and one or more of the hydrogens of the phenylene group may be substituted by a hydrocarbyl group or a functional group; $R^2$ is hydrogen, $C_1$–$C_8$ alkyl, or benzyl; $R^3$, $R^4$, $R^5$, and $R^6$ are each a hydrogen, $C_1$–$C_8$ alkyl, benzyl or phenethyl, or two geminal R moieties, which together with the carbon to which they are attached form a $C_5$–$C_{10}$ cycloalkyl; Z is —O— or NG, wherein G is H or $C_1$–$C_{12}$ alkyl; and when s is greater than 0, P is NH or O; and when s is 0, P=O or O—L—O, where L is a hydrocarbylene. The compound of the formula III is

 (III)

wherein i and j are integers from about 0 to 300 and the sum of i and j is greater than 2, M—F is

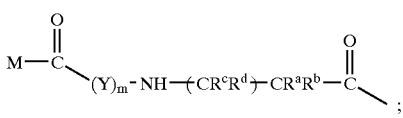

M—F' is

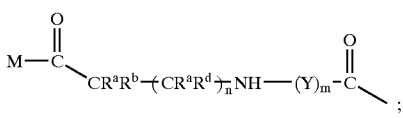

T is a hydrogen or a unit derived from a multi-functional carbonyl compound having the structure

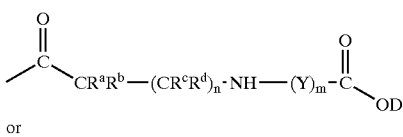

or

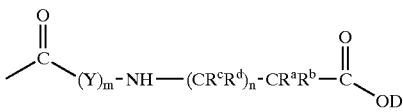

wherein D is a hydrocarbyl group, n is an integer from about 1 to 15, m is either 0 or 1, $R^a$, $R^b$, $R^c$, and $R^d$, are each a hydrogen or a hydrocarbyl group; Y is CO—$(CR^eR^f)_p$, wherein $R^e$ and $R^f$ are each a hydrogen or hydrocarbyl group and p is an integer from about 0 to 20 or CO—$C_6H_4$—, wherein the substitution pattern on the phenylene group is an ortho, meta, or para substitution pattern, and one or more of the hydrogens of the phenylene group may be substituted by a hydrocarbyl group or a functional group; and M is a moiety derived from one or more diamino or a dihydroxy group that contains a 4-aminopiperidine radical of general structure

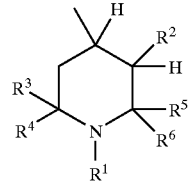

wherein $R^1$ represents hydrogen, $C_1$–$C_{18}$ alkyl, O, OH, $C_1$–$C_{18}$ alkoxy, $C_1$–$C_{18}$ hydroxyalkoxy, $C_5$–$C_{12}$ cycloalkoxy, $C_5$–$C_{12}$ hydroxycycloalkoxy, $CH_2CN$, $C_3$–$C_6$ alkenyl, $C_1$–$C_{18}$ alkynyl, $C_7$–$C_9$ phenylalkyl, unsubstituted or substituted on the phenyl with 1, 2 or 3 $C_1$–$C_4$ alkyls, or an aliphatic $C_1$–$C_8$ acyl; $R^2$ is hydrogen, $C_1$–$C_8$ alkyl, or benzyl; $R^3$, $R^4$, $R^5$, and $R^6$ are each a hydrogen, $C_1$–$C_8$ alkyl, benzyl or phenethyl, or two geminal R moieties, which together with the carbon to which they are attached, form a $C_5$–$C_{10}$ cycloalkyl; and M is bonded to the multi-functional carbonyl compound by the hydroxy or amino group of M.

The amount of compound of formula I, II, or III may be from about 0.01 to 10 percent by weight of the polymeric article. The polymeric material may be polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof. The polymeric material may be a copolymer or homopolymer of a polyolefin. The polymeric material may comprise a polyamide.

The polymeric article may also include one or more additives selected from the group consisting of antioxidants, UV absorbers and light stabilizers, metal deactivators, phosphites and phosphonites, hydroxylamines, nitrones, thiosynergists, peroxide scavengers, polyamide stabilizers, basic co-stabilizers, nucleating agents, fillers and reinforcing agents, benzofuranones, indolinones, acid scavengers, antistatic agents, blowing agents, catalysts, clarifying agents, emulsifiers, fillers, flameproofing agents, fluorescent whitening agents, infrared absorbers, leveling assistants, lubricants, metal deactivators, mold release agents, nucleating agents, optical brighteners, pigments, plasticizers, rheological additives, and mixtures thereof. The one or more additives may be present in an amount of up to about 10 percent by weight of the polymeric article.

The present invention also relates to a multilayer polymeric article comprising a polymeric article having at least one surface and a thin film of a polymer composition applied to at least one surface of the polymeric article and including a sufficient amount of at least one compound of formula I, II, or III to inhibit at least one of photo- or thermal degradation.

The thin film may be applied to each surface of the polymeric article. The amount of the compound may be from about 0.1 to 20 percent by weight of the thin film. The thin film may be from about 5 to 500 μm in thickness. The polymeric article may be a thermoplastic and the thin film may be a thermoplastic. The thermoplastic article and the thin film may be made of the same thermoplastic resin.

The invention further relates to a coating comprising a sufficient amount of at least one compound of formula I, II, or III in an amount sufficient to inhibit at least one of photo- or thermal degradation. The amount of at least one compound of formula I, II, or III may be from about 0.01 to 20 percent by weight of the article.

The invention also relates to a concentrate containing from about 15 to 95 percent of at least one compound of formula I, II, or III.

DETAILED DESCRIPTION OF THE INVENTION

An improved class of HALS compounds has now been discovered that provides substantially similar or superior UV light protection over a longer period of time compared to conventional HALS compounds. The HALS compounds of the present invention are based on the reaction of a lactam with the carbonyl group of a carbonyl compound. The HALS compounds of the present invention include compounds where the functional component of the HALS compound, a piperidin-4-ol or 4 aminopiperidine group, is anchored to the terminus of a hydrocarbon chain by an ester functionality or an amide functionality and wherein the other end of the hydrocarbon chain terminates with an amide linkage that is not a HALS functionality. These may be referred to as "ester/amide HALS compounds" and "amide/amide HALS compounds." Alternatively, both ends of the hydrocarbon chain can terminate with the piperidin-4-ol or 4 aminopiperidine group. In this embodiment, the HALS molecule is anchored to one terminus of the hydrocarbon chain by an ester functionality and to the other terminus by a urethane functionality. These may be referred to as "ester/urethane HALS compounds." Furthermore, the HALS molecule may be anchored to one terminus of the hydrocarbon chain by an amide functionality and to the other terminus by a urea functionality. These may be referred to as "amide/urea HALS compounds." In yet another series of compounds, the piperidin-4-ol or 4 aminopiperidine group is bonded by an ester linkage to one terminus of the hydrocarbon chain and by an oxamate linkage at the other terminus of the hydrocarbon chain to provide "ester/oxamate HALS compounds," or the piperidin-4-ol or 4 aminopiperidine group is bonded by an amide linkage to one terminus of the hydrocarbon chain and by an oxamide linkage at the other terminus of the hydrocarbon chain to provide "amide/oxamide HALS compounds."

Monomeric HALS Compounds of the Invention

These HALS compounds are represented by the general formula (I)

$$RZ\text{—}CO\text{—}CR^aR^b\text{—}(\text{—}CR^cR^d\text{—})_n\text{—}NH\text{—}(Y)_m\text{—}CO\text{—}A \qquad (I)$$

wherein n is an integer from 1 to 15, preferably 4 to 11; m is either 0 or 1; $R^a$, $R^b$, $R^c$, and $R^d$, are each a hydrogen or a hydrocarbyl group; Y is $CO\text{—}(CR^eR^f)_p$, wherein $R^e$ and $R^f$ are each a hydrogen or hydrocarbyl group and p is zero or an integer from 1 to 20 or $CO\text{—}C_6H_4\text{—}$, and the substitution pattern on the phenylene group, i.e., $\text{—}C_6H_4\text{—}$, may be an ortho, meta, or para substitution pattern, in addition one or more of the hydrogens of the phenylene group may be substituted by a hydrocarbyl group or other functional group commonly found in organic molecules; Z is $\text{—}O\text{—}$ or NG, wherein G is H, $C_1\text{–}C_{12}$ alkyl or the radical R; wherein the radical R represents:

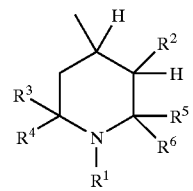

wherein $R^1$ represents hydrogen, $C_1\text{–}C_{18}$ alkyl, O, OH, $CH_2CN$, $C_1\text{–}C_{18}$ alkoxy, $C_1\text{–}C_{18}$ hydroxyalkoxy, $C_5\text{–}C_{12}$ cycloalkoxy, $C_5\text{–}C_{12}$ hydroxycycloalkoxy, $C_3\text{–}C_6$ alkenyl, $C_1\text{–}C_{18}$ alkynyl, $C_7\text{–}C_9$ phenylalkyl, unsubstituted or substituted on the phenyl with 1, 2 or 3 $C_1\text{–}C_4$ alkyls, or an aliphatic $C_1\text{–}C_8$ acyl; $R^2$ is hydrogen, $C_1\text{–}C_8$ alkyl, or benzyl; $R^3$, $R^4$, $R^5$, and $R^6$ are each a hydrogen, $C_1\text{–}C_8$ alkyl, benzyl or phenethyl, or two geminal R moieties, which together with the carbon to which they are attached, form a $C_5\text{–}C_{10}$ cycloalkyl; and A is either ZR or a hydrocarbyl group.

The term "hydrocarbyl," as used herein, is a monovalent hydrocarbon group in which the valency is derived by extraction of a hydrogen from a carbon. Hydrocarbyl includes, for example, aliphatics (straight and branched chain), cycloaliphatics, aromatics and mixed character groups (e.g., aralkyl and alkaryl). Hydrocarbyl also includes groups with internal unsaturation and activated unsaturation. More specifically, hydrocarbyl includes, but is not limited to, alkyl, cycloalkyl, aryl, aralkyl, alkaryl, alkenyl, cycloalkenyl, and alkynyl, typically having from about 1 to 24 carbon atoms, preferably having from about 1 to 12 carbon atoms. A hydrocarbyl may contain one or more carbonyl groups (which is/are included in the carbon count) and/or a heteroatom or heteroatoms (such as at least one oxygen, nitrogen, sulfur, or silicon) in the chain or ring. In addition, a hydrocarbyl may have one or more of the hydrogens of the hydrocarbon group replaced by a functional group commonly found in organic molecules. The phrase "functional group commonly found in organic molecules" means non-hydrocarbyl groups that are typically found in organic molecules including, but not limited to, halides, cyano groups, amino groups, thiol groups, carboxylate groups, hydroxyl groups, sulfonate groups, nitroso groups, nitro groups, and the like.

The term "hydrocarbylene" in the context of the present invention is a divalent hydrocarbon group in which both valencies derive by abstraction of hydrogens from carbon atoms. Included within the definition of hydrocarbylene are the same groups as indicated above for hydrocarbyl and functional hydrocarbyl with, of course, the extra valency (for example, alkylene, alkenylene, arylene, etc.).

In a preferred embodiment of the invention, $R^1$ is H, $C_1$–$C_4$ alkyl, $C_1$–$C_{18}$ alkoxy, $C_5$–$C_{12}$ cycloalkoxy, O, or OH; $R_2$ is H, or $C_1$–$C_4$ alkyl; $R^3$, $R^4$, $R^5$, and $R^6$ are H or $C_1$–$C_4$ alkyl; $R^a$, $R^b$, $R^c$, and $R^d$, are each a hydrogen, aromatic, or $C_1$–$C_4$ alkyl; and n is from about 2 to 10. In a more preferred embodiment, R represents the 2,2,6,6-tetramethylpiperidine radical (i.e., $R^3$, $R^4$, $R^5$, $R^6$ are methyl and $R^2$ is hydrogen) or 1,2,2,6,6-pentamethylpiperidine radical (i.e., $R^2$, $R^3$, $R^5$, and $R^6$ are methyl); $R^a$, $R^b$, $R^c$, and $R^d$ are each a hydrogen; Z is —O—; m is 0 or 1; and n is 4 to 10.

Synthesis of Monomeric HALS Compounds

The HALS compounds of the formula (I) are typically prepared by the reaction of a multi-functional carbonyl compound with a 4-piperidin-ol or a 4-aminopiperidine moiety. The multi-functional carbonyl compound has the general structure:

DO—CO—$CR^aR^b$—(—$CR^cR^d$—)$_n$—NH—(Y)$_m$—CO—B wherein n is an integer from 1 to 15, preferably 4 to 11; m is either 0 or 1; $R^a$, $R^b$, $R^c$ and $R^d$, are each a hydrogen or a hydrocarbyl group; Y is CO—($CR^eR^f$)$_p$, wherein $R^e$ and $R^f$ are each a hydrogen or hydrocarbyl group, and p is zero or an integer from about 1 to 20 or CO—$C_6H_4$—, and the substitution pattern on the phenylene group, i.e., —$C_6H_4$—, is an ortho, meta, or para substitution pattern, in addition one or more of the hydrogens of the phenylene group may be substituted by a hydrocarbyl group or a functional group commonly found in organic molecules; D is a hydrocarbyl group; and B is either OD or D; and reacting the carbonyl compound with a 1-substituted piperidin-4-ol or 4-aminopiperidine of general structure:

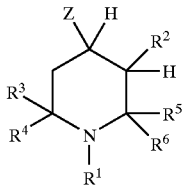

wherein Z is OH or NHG, wherein G is H or $C_1$–$C_{12}$ alkyl or the radical R (wherein R is defined above); and $R^1$ is hydrogen, $C_1$–$C_{18}$ alkyl, O, OH, $CH_2CN$, $C_1$–$C_{18}$ alkoxy, $C_1$–$C_{18}$ hydroxyalkoxy, $C_5$–$C_{12}$ cycloalkoxy, $C_5$–$C_{12}$ hydrocycloalkoxy, $C_3$–$C_6$ alkenyl, $C_1$–$C_{18}$ alkynyl, $C_7$–$C_9$ phenylalkyl, unsubstituted or substituted on the phenyl with 1, 2 or 3 $C_1$–$C_4$ alkyls, or an aliphatic $C_1$–$C_8$ acyl; $R^2$ is hydrogen, $C_1$–$C_8$ alkyl, or benzyl; $R^3$, $R^4$, $R^5$, and $R^6$ are each a hydrogen, $C_1$–$C_8$ alkyl, benzyl or phenethyl, or two geminal R moieties, which together with the carbon to which they are attached, to form a $C_5$–$C_{10}$ cycloalkyl.

The reaction between the multi-functional carbonyl compound and the 4-piperidin-ol or 4-aminopiperidine moiety is conducted for a sufficient time for the compound of formula (I) to be formed. The phrase "conducted for a sufficient time for the compound of [a given formula] to be formed" means that after the reactants are combined they are allowed to react for sufficient time to produce a detectable amount of the desired compound, i.e., the compound of a given formula. By "detectable amount" of a compound is meant an amount of the compound that can be detected by any means readily available to those of ordinary skill in the art. Means for detecting the formation of a compound in a reaction mixture include, but are not limited to, thin layer chromatography (TLC), high performance liquid chromatography (HPLC), gas chromatography (GC), column chromatography, nuclear magnetic resonance spectroscopy (NMR), infra-red (IR) spectroscopy, ultra-violet (UV) or visible (VIS) spectroscopy, and wet-chemical analysis, for example. The length of time for the desired compound to be produced is dependent on a number of variables and, thus, cannot be generalized. For example, the reaction time is dependent on the temperature, the pressure, the specific reactants (i.e., the multi-functional carbonyl compound and the 1-substituted piperidin-4-ol or 4-aminopiperidine), and the solvent and catalyst, if present. Acceptable parameters that produce the desired product, however, may be readily determined by those of ordinary skill in the art without undue experimentation.

The reaction may be carried out in the absence of a solvent or in the presence of a solvent. When the reaction is carried out in the absence of a solvent either the multi-functional carbonyl compound or the 4-piperidin-ol or 4-aminopiperidine may be present in an excess and employed as the reaction medium. Alternatively, the multi-functional carbonyl compound and 4-piperidin-ol or 4-aminopiperidine can be present in a stoichiometric amount. The multi-functional carbonyl compound and 4-piperidin-ol or 4-aminopiperidine may be present in a melt. Preferably, the reaction is carried out in an organic solvent. Any solvent compatible with the reagents may be used. Preferred solvents for use in the method of the invention include, but are not limited to, hydrocarbon solvents such as a saturated alkanes; benzene; toluene; xylenes; halogenated hydrocarbons; ethers such as ethyl ether; cyclic ethers such as tetrahydrofuran and dioxane; amides such as dimethylformamide; sulfoxides such as dimethylsulfoxide; ketones such as 2-butanone or methyl isobutyl ketone; and the like; or combinations thereof. The more preferred solvents include toluene, benzene, and xylenes.

When the reaction is carried out in a solvent the concentration of the multi-functional carbonyl in the organic solvent is generally from about 0.025 M to 2.5 M, preferably from about 0.125 M to 2 M, and more preferably from about 0.25 M to 1.35 M. The molar ratio of the 1-substituted piperidin-4-ol or 4-aminopiperidine to the multi-functional carbonyl compound is between about 20:1 and 1:5, preferably between about 10:1 and 1:3, and more preferably between about 5:1 and 1:5.

The reaction of the multi-functional carbonyl compound and 4-piperidin-ol or 4-aminopiperidine produces an alcohol of structure DOH. Preferably, the alcohol is removed from the reaction mixture as it is formed to help drive the reaction to completion. The alcohol may be removed by any means available to those of ordinary skill in the art such as distillation and or azeotropic distillation.

Preferably, the reaction is conducted in the presence of a catalyst. The optional catalyst may be a basic or an acidic catalyst. The phrase "base catalyst" means any compound that can abstract a proton. Base catalysts suitable for the invention include, but are not limited to, alkoxide ions; hydroxide ion; amide ion; and amines such as triethylamine, DBU (1,8-diazabicyclo [5,4,0] undec-7-ene), or DBN (1,5-diazabicyclo [4,3,0] non-5-ene). When an amine is used as the base, it is preferred that the amine is a tertiary amine.

The phrase "acid catalyst" means any inorganic or organic acid with at least one acidic proton or a Lewis acid. The organic acids include any organic compound that contains at least one acidic functional group, including one or more of $RCO_2H$, $RSO_3H$, $RSO_2H$, RSH, ROH, $RPO_3H$, $RPO_2H$, wherein R is a hydrocarbyl group. Preferred protic acids include HCl, HBr, HI, HNO$_3$, HNO$_2$, H$_2$S, H$_2$SO$_4$, H$_3$PO$_4$, H$_2$CO$_3$, acetic acid, formic acid, propionic acid, butanoic acid, benzoic acid, phthalic acid, oxalic acid, malonic acid, succinic acid, glutaric acid, adipic acid, methanesulfonic acid, and p-toluenesulfonic acid, or mixtures thereof. Lewis acids suitable for the method of the invention include, but are not limited to, aluminum halides, alkylaluminum halides, boron halides, dialkyl tin oxides and derivatives thereof, tin halides, titanium halides, lead halides, zinc halides, iron halides, gallium halides, arsenic halide, copper halides, cadmium halides, mercury halides, antimony halides, and the like. Preferred Lewis acids include aluminum trichloride, aluminum tribromide, 1,3,-diacetoxy-1,1,3, 3-tetrabutyldistannoxane, trimethylaluminum, boron trifluoride, boron trichloride, zinc dichloride, titanium tetrachloride, titanium (IV) isopropoxide, tin dichloride, tin tetrachloride, a tetraalkoxytitanate or a mixture thereof.

The acid or base catalyst may also be a solid supported catalyst such as amberlyst catalysts.

The catalyst is typically added in an amount of less than about 30 mole percent based on the molar quantity of the multi-functional carbonyl compound, preferably less than about 20 mole percent based on the molar quantity of the multi-functional carbonyl compound, more preferably less than about 10 mole percent based on the molar quantity of the multi-functional carbonyl compound, and most preferably less than about 5 mole percent by weight based on the weight of the multi-functional carbonyl compound.

The preferred base catalyst for use in the method of the invention is methoxide ion. The preferred acid catalyst is a Lewis acid. The preferred Lewis acid is 1,3-diacetoxy-1,1, 3,3-tetrabutyldistannoxane.

Preferably, the reaction is allowed to proceed for a time that is less than about 20 hours and more preferably less than about 10 hours. Typically, the reaction temperature is from about room temperature to 150° C., for example, up to the boiling point of the solvent. Typically, the reactions are run at atmospheric pressure. Representative reaction conditions for forming the compound of formula (I) are provided in the examples.

After the compound of formula (I) is formed, it is recovered from the reaction mixture by any means available to those of ordinary skill in the art. Methods for recovering compounds from a reaction mixture include, but are not limited to, chromatography, recrystallization, distillation, extraction, and the like. More than one method may be used to recover a compound from the reaction mixture.

In a preferred embodiment, the substituted 4-piperidin-4-ol is 1,2,2,6,6-pentamethyl-4-piperidinol or 2,2,6,6-tetramethyl-4-piperidinol and the multi-functional carbonyl compound is methyl 6-(methoxycarbonylamino)hexanoate, butyl 6-(butoxycarbonylamino)undecanoate, methyl 6-(butoxycarbonylamino)undecanoate, butyl 6-(methoxycarbonylamino)undecanoate, or methyl 6-(methoxycarbonylamino)undecanoate.

The multi-functional carbonyl compounds can be prepared by any method available to those of ordinary skill in the art. In one embodiment, the multi-functional carbonyl compound is prepared by reacting a lactam with a carbonyl compound. For example, the multi-functional carbonyl compound can be prepared by the base catalyzed reaction of a lactam and a carbonyl compound according to the method disclosed in U.S. Pat. No. 5,300,678, the contents of which are expressly incorporated herein by reference thereto.

Any lactam may be used according to the method of the invention. Preferably the size of the lactam ring is from about 4 to 13 atoms. More preferably the lactam is caprolactam or laurolactam.

The carbonyl compound must include at least one reactive carbonyl group. "Reactive carbonyl group" means any carbonyl group that is attached to a good leaving group and, thus, is activated towards nucleophilic acyl substitution. The reactive carbonyl group may be, for example, an ester or acid chloride. Preferably the carbonyl compound is an ester. More preferred carbonyl compounds include dialkyl carbonates, dialkyl oxalates, dialkyl diesters, or alkyl esters. The general structure of the carbonyl compound is

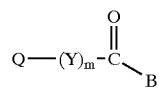

wherein m is either 0 or 1, Q is a good leaving group, such as chloride or OD, wherein D is a hydrocarbyl group, preferably methyl, and B is Q or a hydrocarbyl group and Y is CO—(CR$^e$R$^f$)$_p$, wherein R$^e$ and R$^f$ are each a hydrogen or hydrocarbyl group and p is zero or an integer from about 1 to 20 or CO—C$_6$H$_4$—, and the substitution pattern on the phenylene group, i.e., —C$_6$H$_4$—, may be an ortho, meta, or para substitution pattern, in addition one or more of the hydrogens of the phenylene group may be substituted by a hydrocarbyl group or other functional group commonly found in organic molecules.

When the carbonyl compound is a dialkyl carbonate, the resulting multi-functional carbonyl compound is a hydrocarbon chain that terminates on one end with an ester functionality and the other end with a urethane functionality. When the carbonyl compound is a dialkyl oxalate, the resulting multi-functional carbonyl compound is a hydrocarbon chain that terminates on one end with an ester functionality and the other end with an oxamate functionality. When the carbonyl compound is a dialkyl ester, the resulting multi-functional carbonyl compound is a hydrocarbon chain that includes an amide linkage and terminates on each end with an ester functionality. When the carbonyl compound is an alkyl ester, the resulting multi-functional carbonyl compound is a hydrocarbon chain that terminates on one end with an ester functionality and the other end with an amide functionality.

The reaction of the lactam with the carbonyl compound can be conducted in a solvent or in the absence of a solvent. When the reaction is conducted in the absence of a solvent, excess carbonyl compound may be employed as the reaction medium and, thus, the carbonyl compound may be present in an excess compared to the lactam. The lactam, however, may also be present in an excess and employed as the reaction medium. Alternatively, the lactam and carbonyl compound can be present in a stoichiometric amount. The lactam and carbonyl compound may be present in a melt. When the reaction is conducted in the absence of a solvent, the excess carbonyl compound or lactam may be recovered by, for example, distillation and reused. An advantage of not using a solvent is that the problems associated with disposal of waste solvents are avoided.

In another embodiment one or more different lactams are reacted with one or more different carbonyl compounds. For example, two lactam molecules can be reacted with 1 molecule of carbonyl compound.

Solvents suitable for the method of the invention include, but are not limited to, hydrocarbon solvents such as a saturated alkane; benzene; toluene; xylenes; halogenated hydrocarbons; ethers such as ethyl ether; cyclic ethers such as tetrahydrofuran and dioxane; amides such as dimethylformamide; sulfoxides such as dimethylsulfoxide; ketones such as 2-butanone or methyl isobutyl ketone; alcohols; and the like; or mixtures thereof. When the reaction is carried out in a solvent the concentration of the lactam in the solvent is from about 0.025 M to 10 M, preferably from about 0.375 M to 6 M, and more preferably from about 0.25 M to 4 M. The mole ratio of lactam to carbonyl compound is typically from about 1:10 to 5:1, preferably from about 1:5 to 2:1, and more preferably from about 1:2.5 to 1.5:1.

The reaction is allowed to proceed for a sufficient time to form a detectable amount of the multi-functional carbonyl compound. In general the reaction time is less than about 12 hours. Typically, the reaction temperature is from about room temperature to 150° C., for example, up to the boiling point of the solvent, when a solvent is used. The reaction is typically conducted at room temperature.

The present invention also provides an improved method for preparing the multi-functional carbonyl compound. According to the method of the invention the lactam and a carbonyl compound are reacted in the presence of an acid catalyst, preferably a Lewis acid catalyst.

Any Lewis acid catalyst can be used according to the method of the invention. For example, any of the above-mentioned Lewis acid catalysts may be used. Preferably the Lewis acid catalyst is titanium (IV) isopropoxide. Lewis acids are a preferred catalyst since they can be easily removed from the reaction mixture. For example, many Lewis acids, such as tetraorganotitanates, can be readily hydrolyzed with a stoichometric amount of water, leading to a highly insoluble titanium dioxide that can easily be removed from the reaction mixture by filtration. Other Lewis acids, such as, for example, boron trifluoride etherate, are sufficiently volatile that they can easily be removed from the reaction mixture by distillation. Thus, using a Lewis acid can advantageously avoid having to extract the reaction mixture with an aqueous solvent to remove the catalyst. By avoiding an extraction step to remove the catalyst, the method of the invention generates less aqueous waste that ultimately has to be disposed of.

In another improved method of the invention, the lactam and carbonyl compound are allowed to react with an alkoxide anion as a basic catalyst, preferably methoxide anion. The reaction, however, is conducted at a temperature of less than about 20° C., preferably less than about 19° C., and more preferably less than about 15° C. The lactam and carbonyl compound are allowed to react for less than about 5 hours, preferably less than about 2 hours, and more preferably less than about 1 hour. Conducting the reaction at a low temperature is preferred since temperatures can be kept below the flash point of many reagents and, thus, such low temperature reactions can be significantly safer. For example, dimethyl carbonate (which is a common carbonyl compound for use in the method of the invention) has a flash point of 19° C. By running the reaction at a temperature below 19° C., i.e., below the flash point, the method is significantly safer than prior art methods that require higher temperatures.

When the multi-functional carbonyl compound is formed, it can be recovered from the reaction mixture before it is reacted with the 1-substituted piperidin-4-ol or 4-aminopiperidine to form the HALS of the invention. The multi-functional carbonyl compound may be recovered by any means available to those of ordinary skill in the art. Optionally, the multi-functional carbonyl compound is not recovered from the reaction mixture and instead the 1-substituted piperidin-4-ol or 4-aminopiperidine is added to the reaction mixture after a detectable amount of the multi-functional carbonyl compound is formed. The 1-substituted piperidin-4-ol or 4-aminopiperidine and the multi-functional carbonyl compound can then react to form the HALS of the invention.

In a preferred method, the compound of formula (I) is prepared by reacting the lactam, carbonyl compound, and 1-substituted piperidin-4-ol or 4-aminopiperidine in a single step. The lactam, the carbonyl compound, and the 1-substituted piperidin-4-ol or 4-aminopiperidine are combined and allowed to react at the same time, rather than reacting the lactam and carbonyl compound to form the multi-functional carbonyl compound in a first step and then, in a subsequent step, reacting the multi-functional carbonyl compound with the 1-substituted piperidin-4-ol or 4-aminopiperidine. The lactam, the carbonyl compound, and the 1-substituted piperidin-4-ol or 4-aminopiperidine are combined in a reaction vessel and allowed to react for sufficient time to form a detectable amount of the HALS of formula (I).

The ratio of lactam to carbonyl compound in this embodiment of the method is from about 2:1 to 1:4, preferably from about 1:1 to 1:2; and the ratio of lactam to 1-substituted piperidin-4-ol or 4-aminopiperidine is from about 1:1 to 1:6, preferably from about 1:2 to 1:4.

The single step reaction can be conducted in a solvent or in the absence of a solvent. When a solvent is used, any solvent that is compatible with the reagents may be used. Representative solvents include, but are not limited to, those solvents described above for the reaction of a 1-substituted piperidin-4-ol or 4-aminopiperidine with a multi-functional carbonyl compound. Preferably, the reaction in this embodiment is carried out in the presence of a solvent. When a solvent is employed, the concentration of lactam is typically from about 0.025 M to 10 M, preferably from about 0.325 M to 6 M, and more preferably from about 0.75 M to 4 M.

Preferably, the reaction is carried out in the presence of a catalyst. The same catalysts may be used as were used in the reaction of a 1-substituted piperidin-4-ol or 4-aminopiperidine with a multi-functional carbonyl compound. The catalyst is typically present in an amount of less than about 30 mole percent, preferably less than about 20 mole percent, and more preferably less than about 10 mole percent, and most preferably less than 5 mole percent, relative to the amount of carbonyl compound.

Preferably, the carbonyl compound is an ester, i.e., Q=OD, so that the reaction produces an alcohol of structure HOD. Preferably, the alcohol is removed from the reaction mixture as it is formed to drive the reaction to completion. The alcohol may be removed by any means available to those of ordinary skill in the art, such as distillation and/or azeotropic distillation.

Preferably, the reaction time is less than about 20 hours and more preferably less than about 10 hours. Typically, the reaction temperature is between about room temperature and 250° C. Typically, the reactions are run at atmospheric pressure. Representative reaction conditions for forming the HALS of formula (I) by the single step process are provided in the examples. When the HALS of formula (I) is formed it may be recovered from the reaction mixture by any means available to those of ordinary skill in the art.

Oligomeric HALS Compounds of the Invention

The invention also includes oligomeric HALS having the general formula (II)

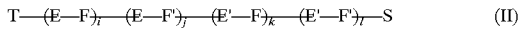

(II)

wherein i, j, k, and l are integers from about 0 to 300, preferably about 0 to 200, and more preferably 0 to about 100. The sum of i, j, k, and l is greater than 2, preferably, the sum of i, j, k, and l is greater than about 3 and more preferably is greater than about 6. Preferably at least two of i, j, k, and l are 1 or more, or (III)

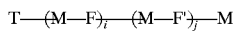 (III)

wherein i and j are integers from about 0 to 300, preferably about 0 to 200, and more preferably 0 to about 100. The sum of i and j is greater than 2. Preferably, the sum of i and j is greater than about 3, more preferably greater than about 6. Preferably at least two of i, j, k, and l are equal to or greater than 1.

In formula (II) E and E' are a piperidin-4-ol or 4-aminopiperidine moiety and F and F' are each a moiety derived from a multi-functional carbonyl compound. T can be F, F', or hydrogen and S can be E, E', or hydrogen.

E-F includes:

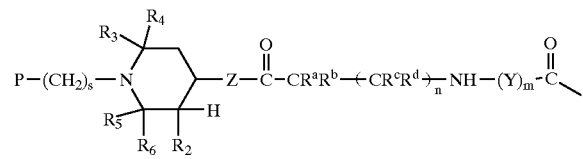

E-F' includes:

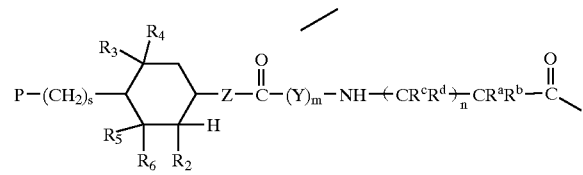

E'-F includes:

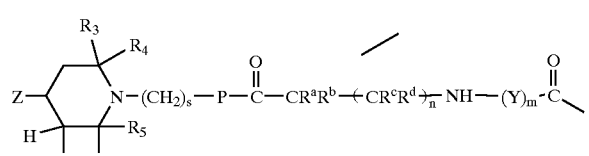

and E'-F' includes:

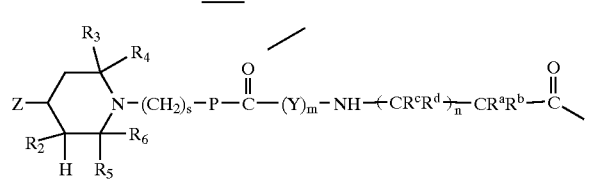

E—F' includes:

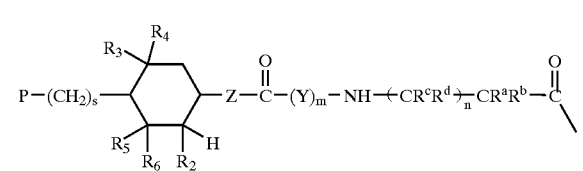

E'—F includes:

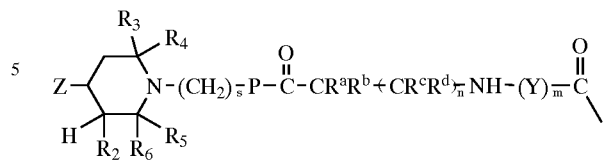

E'—F' includes:

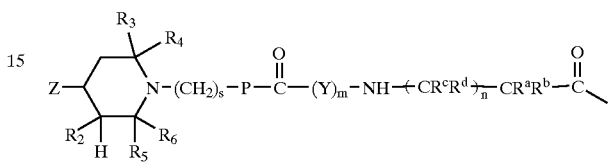

In formula (III), M is a diamino or a dihydroxy group that contains the 4-aminopiperidine group, R, as defined above. By "diamino or a dihydroxy group" is meant a group derived from a compound that contains at least two hydroxy groups, at least two amino groups, or at least one amino group and one hydroxy group. The amino group can be either a primary or secondary amino group.

M—F includes:

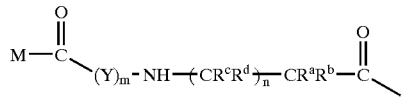

M—F' includes:

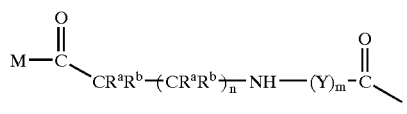

In the oligomeric HALS of formula (III) the diamino or dihydroxy group that contains the 4-aminopiperidine group, i.e., M, is bonded to the multi-functional carbonyl compound by the hydroxy or amino group.

Formulas II and III may be a block copolymer or a random copolymer, i.e., the units E—F, E—F', E'—F, and E'—F' or M—F and M—F' are distributed randomly throughout the polymer chain. In the above oligomeric HALS of structure (II) or (III) S is a hydrogen, or a unit derived from a piperidin-4-ol or a 4-aminopiperidine moiety and has the structure

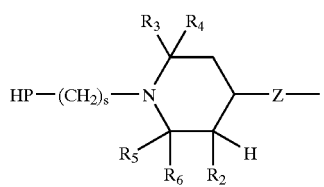

or

-continued

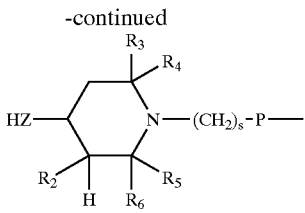

and T is a hydrogen or a unit derived from a multi-functional carbonyl compound and has the structure

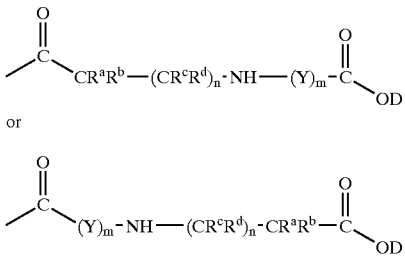

wherein D is a hydrocarbyl group.

In the oligomeric HALS of formula (II) and (III) n is an integer from 1 to 15, preferably 4 to 11, m is either 0 or 1, s is 0 or an integer from about 1 to 10; $R^a$, $R^b$, $R^c$, and $R^d$, are each a hydrogen or a hydrocarbyl group; Y is CO—$(CR^eR^f)_p$, wherein $R^e$ and $R^f$ are each a hydrogen or hydrocarbyl group and p is zero or an integer from about 1 to 20 or CO—$C_6H_4$—, wherein the substitution pattern on the phenylene group is an ortho, meta, or para substitution pattern, and one or more of the hydrogens of the phenylene group may be substituted by a hydrocarbyl group or a functional group commonly found in organic molecules; Z is —O— or NG, wherein G is H or $C_1$–$C_{12}$ alkyl; $R^2$ is hydrogen, $C_1$–$C_8$ alkyl, or benzyl; $R^3$, $R^4$, $R^5$, and $R^6$ are each a hydrogen, $C_1$–$C_8$ alkyl, benzyl or phenethyl, or two geminal R moieties, which together with the carbon to which they are attached, form a $C_5$–$C_{10}$ cycloalkyl; and when s is greater than 0, P is NH or O; and when s is 0, P=O or O—L—O, where L is a hydrocarbylene.

As noted above, in the HALS of formula (II), E, E' and S are units derived from a piperidin-4-ol or a 4-aminopiperidine moiety and F, F' and T are units derived from a multi-functional carbonyl compound and in the HALS of formula (III) F and F' are derived from a multi-functional carbonyl compound and M is as defined above. In the HALS of formula (II) it is preferably that the mole percent of the units derived from the multi-functional carbonyl compound is greater than the mole percent of the units derived from a piperidin-4-ol or a 4-aminopiperidine moiety. In the HALS of formula (III) it is preferably that the mole percent of the units derived from the multi-functional carbonyl compound is greater than the mole percent of the diamino or dihydroxy group that contains the 4-aminopiperidine group, i.e., M,. This is advantageous since they are less expensive.

Preferably, in the oligomeric HALS of formula (II), $R_2$ is H, or $C_1$–$C_4$ alkyl; $R^3$, $R^4$, $R^5$, and $R^6$ are each H or $C_1$–$C_4$ alkyl; $R^a$, $R^b$, $R^c$, and $R^d$, are each a hydrogen, aromatic, or $C_1$–$C_4$ alkyl; n is from about 4 to 11; and s is from about 2 to 5. In a more preferred embodiment, $R^2$ is a hydrogen; $R^3$, $R^4$, $R^5$, and $R^6$ are each methyl; $R^a$, $R^b$, $R^c$, and $R^d$, are each a hydrogen, Z is 0, n is between 4 and 11, and s is 2, m is 0 and P is O.

In another embodiment, $R^2$ is hydrogen, $R^3$, $R^4$, $R^5$ and $R^6$ are methyl, $R^a$, $R^b$, $R^c$ and $R^d$ are each hydrogen, Z is 0, n is from 4 to 11 and s is 0.

Preferably, in the oligomeric HALS of formula (III), M is N,N'-bis(2,2,6,6-tetramethyl-4-piperidinyl)-1,6-hexanediamine (BPIP) or N-(2,2,6,6-tetramethylpiperidinol)diethanolamine and n is from about 4 to 11.

Advantageously, the number average molecular weight of the oligomeric HALS compound of formula (II) and (III) is typically from about 400 to 20,000, preferably, from about 1,000 to 15,000, and more preferably from about 2,000 to 9,000.

Synthesis of Oligomeric HALS Compounds

The present invention also relates to a method of forming oligomeric HALS of formula (II) and formula (III). Oligomeric HALS of formula (II) are prepared by reacting a multi-functional carbonyl compound of general structure DO—CO—$CR^aR^b$—(—$CR^cR^d$—)$_n$—NH—$(Y)_m$—CO—OD   (IV)

wherein n is an integer from about 1 to 15, preferably 4 to 11, m is either 0 or 1; $R^a$, $R^b$, $R^c$, and $R^d$, are each a hydrogen or a hydrocarbyl group; Y is CO—$(CR^eR^f)_p$, wherein $R^e$ and $R^f$ are each a hydrogen or hydrocarbyl group and p is zero or an integer from about 1 to 20 or CO—$C_6H_4$—, wherein the substitution pattern on the phenylene group may be an ortho, meta, or para substitution pattern, and one or more of the hydrogens of the phenylene group may be substituted by a hydrocarbyl group or a functional group commonly found in organic molecules; and D is a hydrocarbyl group, with a 1-substituted piperidin-4-ol or 4-aminopiperidine of general structure:

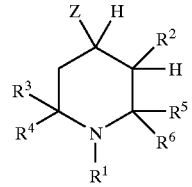

wherein Z is OH or or NHG, wherein G is H or $C_1$–$C_{12}$ alkyl; $R^2$ is —$(CH_2)_s$—OH, —$(CH_2)_s$—$NH_2$, $C_1$–$C_{18}$ hydroxyalkoxy or $C_1$–$C_{12}$ hydroxycycloalkoxy; wherein s is an integer from about 1 to 10, preferably 2 to 8; $R^2$ represents hydrogen, $C_1$–$C_8$ alkyl, or benzyl; $R^3$, $R^4$, $R^5$, and $R^6$ are each a hydrogen, $C_1$–$C_8$ alkyl, benzyl or phenethyl, or two geminal R moieties, which together with the carbon to which they are attached, form a $C_5$–$C_{10}$ cycloalkyl.

Oligomeric HALS of formula (III) are prepared by reacting a multi-functional carbonyl compound of general structure (IV) with a diamino or a dihydroxy compound that contains the 4-aminopiperidine group. Preferably, the diamino or dihydroxy compound includes N,N'-bis(2,2,6,6-tetramethyl-4-piperidinyl)-1,6-hexanediamine (BPIP) or N-(2,2,6,6-tetramethylpiperidinol) diethanolamine.

The multi-functional carbonyl compounds are prepared by any method available to those of ordinary skill in the art. Preferably, the multi-functional carbonyl compounds are prepared by the method of the invention wherein a carbonyl compound is reacted with a lactam in the presence of a Lewis acid or wherein a carbonyl compound is reacted with a lactam and an alkoxide at a low temperature, i.e., less than 20° C. The carbonyl compound, however, must have two reactive carbonyl groups or a single carbonyl group that is activated with two leaving groups (for example, phosgene or a dialkyl carbonate). Preferably, the leaving group is an ester. Preferred carbonyl compound include dialkyl carbonates, dialkyl oxalates, and dialkyl esters.

The reaction can be carried out in the absence of a solvent or in the presence of an organic solvent. When the reaction is carried out in the absence of a solvent, either the multi-functional carbonyl compound or the 1-substituted piperidin-4-ol or 4-aminopiperidine (for compound (II)) or the diamino or dihydroxy compound that contains the 4-aminopiperidine group (for compound (III)) may be present in an excess and employed as the reaction medium. Alternatively, the multi-functional carbonyl compound and the 1-substituted piperidin-4-ol or 4-aminopiperidine or the diamino or a dihydroxy compound that contains the 4-aminopiperidine group can be present in stoichiometric amounts. The reaction can also be conducted in a melt.

Preferably, the reaction is carried out in an organic solvent. Any solvent compatible with the reagents may be used. Preferred solvents for use in the method of the invention include, but are not limited to, hydrocarbon solvents such as a saturated alkanes; benzene; toluene; xylenes; halogenated hydrocarbons; ethers such as ethyl ether; cyclic ethers such as tetrahydrofuran and dioxane; amides such as dimethylformamide; sulfoxides such as dimethylsulfoxide; ketones such as 2-butanone or methyl isobutyl ketone; and the like; or a mixture thereof. The more preferred solvents include toluene, benzene, and xylenes, or a mixture thereof.

The concentration of the multi-functional carbonyl compound in the organic solvent is generally present in an amount of from about 0.025 M to 2.5 M, preferably from about 0.125 M to 0.2 M, and more preferably from about 0.25 M to 1.35 M. The molar ratio of the multi-functional carbonyl compound to the 1-substituted piperidin-4-ol or 4-aminopiperidine, used to prepare the oligomeric HALS of formula (II), or to the diamino or dihydroxy compound that contains the 4-aminopiperidine group, used to prepare the oligomeric HALS of formula (III), is from about 5:1 to 1:5, preferably from about 2:1 to 1:2, and more preferably from about 1.2:1 to 1:1.2.

In a preferred embodiment of the method of making the oligomeric HALS of formula (II), the substituted piperidin-4-ol or 4-aminopiperidine includes N-(2-hydroxyethyl)-2,2,6,6-tetramethyl-4-piperidinol. In a preferred embodiment of the method of making the oligomeric HALS of formula (III), the diamino or a dihydroxy compound that contains the 4-aminopiperidine group 4-aminopiperidine includes BPIP or N-(2,2,6,6-tetramethyl piperidinol) diethanolamine or a mixture thereof.

Optionally, but preferably the reaction is conducted in the presence of a catalyst. The catalyst may be a basic catalyst or an acid catalyst. Preferably, the base catalyst is methoxide ion. Preferably the acid catalyst includes a Lewis acid. The preferred Lewis acid includes 1,3-diacetoxy-1,1,3,3-tetrabutyldistannoxane.

The catalyst is typically added in an amount of less than about 30 mole percent by weight based on the weight of the multi-functional carbonyl compound, preferably less than about 20 mole percent by weight based on the weight of the multi-functional carbonyl compound, more preferably less than about 10 mole percent by weight based on the weight of the multi-functional carbonyl compound, and most preferably less than about 5 mole percent by weight based on the weight of the multi-functional carbonyl compound.

The reaction of the multi-functional carbonyl compound and the 1-substituted piperidin-4-ol or 4-aminopiperidine, used to prepare the oligomeric HALS of formula (II), or the diamino or dihydroxy compound that contains the 4-aminopiperidine group, used to prepare the oligomeric HALS of formula (III), is conducted for sufficient time to form a detectable amount of the oligomeric HALS of formula (II) or (III). The reaction time temperature and pressure may readily be determined by one of ordinary skill in the art without undue experimentation. Typically, the reaction time is less than about 20 hours, preferably less than about 15 hours, and more preferably less than about 10 hours. Typically, the reaction temperature is from about room temperature to about 150° C., for example, up to the boiling point of the solvent. Preferably, the reaction is carried out at atmospheric pressure. Representative reaction conditions for forming the compound of formula (II) or (III) are provided in the examples.

After the oligomeric HALS of formula (II) or (III) are formed, they are recovered from the reaction mixture by any means available to those of ordinary skill in the art.

In a preferred method, the oligomeric HALS of formula (II) and (III) are formed by reacting a lactam, a carbonyl compound of general structure

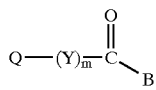

wherein m is either 0 or 1, Q is a good leaving group, such as chloride or OD, wherein D is a hydrocarbyl group, preferably methyl, and B is Q or a hydrocarbyl group and Y is CO—$(CR^eRR^f)_p$, wherein $R^e$ and $R^f$ are each a hydrogen or hydrocarbyl group and p is zero or an integer from about 1 to 20 or CO—$C_6H_4$—, and the substitution pattern on the phenylene group may be an ortho, meta, or para substitution pattern, in addition one or more of the hydrogens of the phenylene group may be substituted by a hydrocarbyl group or other functional group commonly found in organic molecules, and a 1-substituted piperidin-4-ol or 4-aminopiperidine, in the case of oligomeric HALS of formula (II), or a diamino or a dihydroxy compound, in the case of oligomeric HALS of formula (III), in a single step. The lactam, carbonyl compound, and a 1-substituted piperidin-4-ol or 4-aminopiperidine or a diamino or a dihydroxy compound that contains the 4-aminopiperidine group are combined in a reaction vessel and allowed to react for sufficient time to form a detectable amount of the compound of formula (II) or (III). The ratio of lactam to carbonyl compound is from about 2:1 to 1:4, preferably from about 1:1 to 1:2 and the ratio of lactam to 1-substituted piperidin-4-ol or 4-aminopiperidine or diamino or a dihydroxy compound is from about 2:1 to 1:2, preferably about 1:1.

The single step reaction may be conducted in a solvent or in the absence of a solvent. Preferably, the reaction is conducted in the presence of a solvent. When a solvent is used any solvent that is compatible with the reagents may be used. Representative solvents include, but are not limited to, those solvents described above for the reaction of a 1-substituted piperidin-4-ol or 4-aminopiperidine with a multi-functional carbonyl compound. When a solvent is employed, the concentration of the lactam is typically from about 0.075 M to 10 M, preferably from about 0.375 M to 6 M, and more preferably from about 0.75 M to 4 M.

Optionally, but preferably, the reaction is carried out in the presence of a catalyst. The same catalysts may also be used as were used in the reaction of a 1-substituted piperidin-4-ol or 4-aminopiperidine with a multi-functional carbonyl compound. The catalyst is typically present in an amount of less than about 30 mole percent, preferably less than about 20 mole percent, more preferably less than about 10 mole percent, and most preferably less than 5 mole percent relative to the amount of carbonyl compound.

In general the reaction time is less than about 20 hours, preferably less than about 15 hours, and more preferably less than about 10 hours. Typically, the reaction temperature is from about room temperature to 250° C. Preferably, the reaction is carried out at atmospheric pressure. Representative reaction conditions for forming the oligomeric HALS in a single step according to the method of the invention can readily be determined by one of ordinary skill in the art, but guidance is also provided in the examples.

When the oligomeric HALS of formula (II) or (III) is formed it may be recovered from the reaction mixture by any means available to those of ordinary skill in the art.

Polymeric Articles Including HALS and Manufacture of the Same

The HALS of the present invention, i.e., HALS of formula (I), (II), or (III) may be provided as neat compounds or may be provided in the form of a concentrate including from about 15 to 98 percent by weight, and preferably from about 20 to 95 percent by weight, preferably from about 25 to 90 percent by weight, and more preferably from about 40 to 70 percent of at least one of the HALS compounds of formula (I), (II), or (III) and a polymeric resin.

The HALS compounds of the present invention impart superior weatherability and yellowing resistance to polymers. In addition, the HALS compounds of the present invention typically exhibit low volatility. Thus, the present invention also provides polymeric articles stabilized by including an effective amount of the newly discovered HALS compounds to inhibit at least one of photo- or thermal degradation and methods of making the polymeric articles. Any suitable polymer compatible with a HALS composition of the invention may be combined with one or more HALS of the invention to form a polymeric article protected from UV light. The polymeric article includes at least one polymeric material and a sufficient amount of at least one HALS of formula (I), (II), or (III) to inhibit at least one of photo- or thermal degradation. Typically, the polymeric article is stabilized by blending from about 0.01 percent to 10 percent by weight, preferably from about 0.03 percent to 1 percent by weight, and more preferably from about 0.05 percent to 0.5 percent by weight of at least one HALS of formula (I), (II), or (III) with a polymeric material used to form the article. The article may be an extruded article, a molded article, a tape, a film, a fiber, or a coating, for example.

The method of making the polymeric articles includes blending a polymeric material with from about 0.01 percent to 10 percent by weight, preferably from about 0.03 percent to 1 percent by weight, and more preferably from about 0.05 percent to 0.5 percent by weight at least one HALS compounds of the present invention to form a stabilized polymeric composition, and forming an article from the polymeric composition. The polymeric article may be formed by extrusion, sheet extrusion, injection molding, blow molding, injection blow molding, rotational or roto-molding, calendering, thermoforming, compression molding, vacuum molding, pressure molding, reaction injection molding, solvent casting, fiber spinning, and other similar techniques available to those of ordinary skill in the art. The HALS of the invention may be added to the polymeric material by any means known in the art, and one of ordinary skill in the art may readily envision a variety of such ways to combine one or more HALS compounds and one or more polymeric materials to form polymeric articles according to the invention.

A variety of other conventional additives, individually or in combination, may also be added to the polymeric material. Examples of such additives include, but are not limited to one or more of the following classes:

a. Antioxidants (i) Alkylated monophenols, such as 2,6-di-tert-butyl-4-methylphenol, 2-tert-butyl-4,6-dimethylphenol, 2,6-di-tert-butyl-4-ethylphenol, 2, 6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol; nonylphenols which are liner or branched in the side chains such as 2,6-di-nonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol, CYANOX® 1790, CYANOX® 2246, and CYANOX® 425 Antioxidants, commercially available from CYTEC INDUSTRIES of West Paterson, N.J., IRGANOX® 1010 Antioxidant and IRGANOX® 1076 Antioxidant, commercially available from of CIBA SPECIALTIES of Hawthorne, N.Y., and mixtures thereof;

(ii) Alkylthiomethylphenols, such as 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol, and mixtures thereof;

(iii) Hydroquinones and alkylated hydroquinones, such as 2,6-di-tert-butyl-4-methoxyhenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, and bis (3,5-di-tert-butyl-4-hydroxyphenyl)adipate.

(iv) Tocopherols, such as α-tocopherol (vitamin E), β-tocopherol, γ-tocopherol, δ-tocopherol, and mixtures thereof;

(v) Hydroxylated thiodiphenyl ethers, such as 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide, and mixtures thereof;

(vi) Alkylidenebisphenols, such as 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α, α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxylbenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis (3'-tert-butyl-4'-hydroxyphenyl)butyrate], bis(3-tert-butyl4-hydroxy-5-methylphenyl)dicyclopentadiene, bis[2-(3'-tert-butyl-2'-hydroxy-5'methylbenzyl)-6- tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane, and mixtures thereof;

(vii) O—, N— and S-benzyl compounds, such as 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate, and mixtures thereof;

(viii) Hydroxybenzylate malonates, such as dioctadecyl-2,2-bis(3,5-di-tert-butyl-2-hydroxybenzyl)malonate, dioctadecyl-2-(3-tert-butyl-4-hydroxy-5-methylbenzyl)malonate, didodecyl-mercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate, and mixtures thereof;

(ix) Aromatic hydroxybenzyl compounds, such as 1,3,5-tris(3,5-di-tert-butyl-4-hydroxybenzyl)-2,4,6trimethylbenzene, 1,4-bis(3,5-di-tert-butyl-4-hydroxybenzyl)-2,3,5,6-tetramethylbenzene, 2,4,6-tris (3,5-di-tert-butyl-4-hydroxybenzyl)phenol, and mixtures thereof;

(x) Triazine compounds, such as 2,4-bis(octylmercapto-6-(3,5-di-tert-butyl-4-hydroxy-anilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4hydroxyphenoxy)-1,3,5-triazine, 2,4,6-tris(3,5-di-tert-butyl-4-hydroxyphenoxy)-1,3,5-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate, and mixtures thereof;

(xi) Benzylphosphonates, such as dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid, and mixtures thereof;

(xii) Acylaminophenols, such as 4-hydroxylauranilide, 4-hydroxystearanilide, and octyl N-(3,5-di-tert-butyl-4-hydroxyphenyl)carbamate, and mixtures thereof;

(xiii) Esters of β-(3,5-di-tert-butyl-4-hydroxyphenyl) propionic acid; β-(5-tert-butyl-4-hydroxy-3-methylphenyl)propionic acid; β-(3,5-dicyclohexyl-4-hydroxyphenyl)propionic acid; 3,5-di-tert-butyl-4-hydroxyphenyl acetic acid with mono- or polyhydric alcohols, such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, and mixtures thereof;

(xiv) Amides of β-(3,5-di-tert-butyl-4-hydroxyphenyl) propionic acid, such as N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine, and mixtures thereof;

(xv) Ascorbic acid (Vitamin C) or salt or ester thereof;

(xvi) Aminic antioxidants, such as N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfon-amoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine such as p,p'-di-tert-octyldiphenylamine, 4-n-butylaminophenol, 4-butyrylaminophenol, 4-nonanoylaminophenol, 4-dodecanoylaminophenol, 4-octadecanoylamino-phenol, bis(4-methoxyphenyl)amine, 2,6-di-tert-butyl-4-dimethylaminomethylphenol, 2,4'-diaminophenylmethane, 4,4'-diaminodiphenyl-methane, N,N,N',N'-tetramethyl-4,4'-diaminodiphenylmethane, 1,2-bis[(2-methylphenyl) amino]ethane, 1,2-bis(phenylamino)propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenyl-amines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octyl phenothiazines, a mixture of mono- and dialkylated tert-octylphenothiazines, -allylphenothiazine, N,N,N',N'-tetraphenyl-1,4-diaminobut-2-ene, N,N-bis(2,2,6,6-tetramethyl-piperid-4-yl)hexamethylenediamine, bis(2,2,6,6-tetramethylpiperid-4-yl)sebacate, 2,2,6,6-tetra-methylpiperidin-4-one, 2,2,6,6-tetramethylpi-peridin-4-ol, and mixtures thereof;

b. Conventional UV-Absorbers and Light Stabilizers
  (i) 2-(2'-Hydroxyaryl)benzotriazoles, such as 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl) benzotriazole or 2-(2H-benzotriazol-2-yl)-4-tert-octyl-phenol known as CYASORB® UV-5411 Light Stabilizer, commercially available from CYTEC INDUSTRIES of West Paterson, N.J., 2-(3',5'-di-tert-butyl-2'-hydroxyphenyl)-5-chlorobenzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octoxyphenyl)benzotriazole, 2-(3',5'-di-tert-amyl-2'-hydroxphenyl)benzotriazole, 2-(3',5'-bis(α,α-dimethylbenzyl)-2'-hydroxyphenyl)-benzotriazole, a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole and 2-(3'-tert-butyl-2'-hydroxy-5'-(2-isooctyloxycarbonylethyl) phenylbenzotriazole, 2,2-methylenebis[4-(1,1,3,3-tetramethylbutyl)-6-benzotriazole-2-yl phenol], the transesterification product of 2-[3'-tert-butyl-5'-(2-methoxycarbonylethyl)-2'-hydroxyphenyl] benzotriazole with polyethylene glycol 300, [R—CH₂CH—COO(CH₂)₃]₂— where R=3'-tert-butyl-4'-hydroxy-5'-2H-benzotriazol-2-yl phenyl, TINUVIN® 900 Light Stabilizer, commercially available from CIBA SPECIALTIES, and mixtures thereof;
  (ii) 2-Hydroxybenzophenones, for example the 4-hydroxy, 4-methoxy, 4-octoxy CYASORB® UV-531 Light Stabilizer, commercially available from CYTEC INDUSTRIES), 4-decyloxy, 4-dodecyloxy, 4-benzyloxy, 4,2',4'-trihydroxy and 2'-hydroxy-4,4'-dimethoxy compounds, and mixtures thereof;
  (iii) Esters of substituted and unsubstituted benzoic acids or salicylic acid compounds, such as 4-tert-butyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxy-benzoate, hexadecyl 3,5-di-tert-butyl-4-hydroxy-benzoate, octadecyl 3,5-di-tert-butyl-4-hydroxy-benzoate, and 2-methyl-4,6-di-tert-butylphenyl-3,5-di-tert-butyl-4-hydroxybenzoate, and mixtures thereof;
  (iv) Acrylates or alkoxycinnamates, such as ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, and mixtures thereof;
  (v) Nickel compounds including nickel (II) complexes of amines and thio-bis-phenols, such as nickel complexes of 2,2'-thio-bis-[4-(1,1,3,3-tetramethylbutyl) phenol], including the 1:1 or 1:2 complex, with or without additional ligands, such as n-butylamine, triethanolamine or N-cyclohexyldiethanolamine, nickel dibutyldithiocarbamate, nickel salts of monoalkyl esters including the methyl or ethyl ester of 4-hydroxy-3,5-di-tert-butylbenzylphosphonic acid, nickel complexes of ketoximes including 2-hydroxy-4-methylphenyl undecyl ketoxime, nickel complexes of 1-phenyl-4-lauroyl-5-hydroxypyrazole, with or without additional ligands, and mixtures thereof;
  (vi) Sterically hindered amines, as well as the N compounds thereof (e.g., N-alkyl, N-hydroxy, N-alkoxy and N-acyl), such as bis(2,2,6,6-tetramethyl-piperidin-4-yl) sebacate, bis(2,2,6,6-tetramethyl-piperidin-4-yl)succinate, bis(1,2,2,6,6-pentamethyl-piperidin-4-yl)sebacate, bis(1-octyloxy-2,2,6,6-tetramethylpiperidin-4-yl)sebacate, bis(1,2,2,6,6-pentamethylpiperidin-4-yl) n-butyl 3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethylpiperidin-4-yl) hexamethylenediamine and 4-tert-octylamino-2,6-dichloro-1,3,5-triazine, tris(2,2,6,6-tetramethylpiperidin-4-yl) nitrilotriacetate, tetrakis(2,2,6,6-tetramethylpiperidin-4-yl)-1,2,3,4-butanetetra-carboxylate, 1,1'-(1,2-ethanediyl)bis(3,3,5,5-tetramethylpiperazinone), 4-benzoyl-2,2,6,6-tetra-methylpiperidine, 4-stearyloxy-2,2,6,6-tetramethyl-piperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, the condensate of N,N'-bis(2,2,6,6-tetramethylpiperidin-4-yl) hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-bis(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(1-ethanoyl-2,2,6,6-tetramethylpiperidin-4-yl)pyrrolidin-2,5-dione, 3-dodecyl-1-(2,2,6,6-tetramethylpiperidin-4-yl) pyrrolidin-2,5-dione, 3-dodecyl-1-(1,2,2,6,6-pentamethylpiperidin-4-yl)pyrrolidine-2,5-dione, a mixture of 4-hexadecyloxy- and 4-stearyloxy-2,2,6,6-tetramethylpiperidine, the condensate of N,N'-bis(2,2,6,6-tetramethylpiperidin-4-yl)hexamethylenediamine and 4-cyclohexylamino-2,6-dichloro-1,3,5-triazine, the condensate of 1,2-bis(3-aminopropylamino)ethane, 2,4,6-trichloro-1,3,5-triazine and 4-butylamino-2,2,6,6-tetramethylpiperidine (CAS Reg. No. [136504-96-6]), N-(2,2,6,6-tetramethyl piperidine-4-yl)-n-dodecylsuccinimide, N-(1,2,2,6,6-pentamethylpiperidin-4-yl)-n-dodecylsuccinimide, 2-undecyl-7,7,9,9-tetramethyl-1-oxa-3,8-diaza-4-oxospiro[4.5]decane, oxo-piperanzinyl-triazines or so called PIP-T HALS, e.g., GOODRITE® 3034, 3150 and 3159 commercially available form BF Goodrich Chemical Co. of Akron, Ohio and similar materials disclosed in U.S. Pat. No. 5,071,981, photobondable HALS such as SANDUVOR® PR-31 AND PR-32 commercially available from Clariant Corp. of Charlotte N.C., and similar materials disclosed in GB-A-2269819, the reaction product of 7,7,9,9-tetramethyl-2-cycloundecyl-1-oxa-3,8-diaza-4-oxospiro[4.5]decane and epichlorohydrin. Examples of the tetramethylpiperidine derived HALS include CYASORB® UV-3346 Light Stabilizer, commercially available from CYTEC INDUSTRIES, SANDUVOR® 3055HALS, SANDUVOR® 3056HALS, and SANDUVOR® 3058HALS, commercially available from SANDOZ Corporation of Charlotte, N.C., CHIMASORB® 944 Stabilizer, TINUVIN® 622 Stabilizer, and TINUVIN® 144 Stabilizer, each commercially available from CIBA SPECIALTIES, and mixtures thereof. See also generally U.S. Pat. Nos. 5,106,891, 4,740, 542, 4,619,956, 4,426,471, 4,426,472, 4,356,307, 4,344,876, 4,314,933; GB-A-2269819, EP-A-309400, EP-A-309401, EP-A-309402 and EP-A-0434608, each of which is incorporated herein by reference in their entirety;

(vii) Oxamides, oxanilides, benzoxazinones, benzoxazoles, or triazines, such as 2,2'-(1,4-methylene)bis [4H-3,1-benzoxazin-4-one] (CYASORB® UV-3638 Light Stabilizer, commercially available from CYTEC INDUSTRIES), 4,4'-dioctyloxyoxanilide, 2,2'-diethoxyoxanilide, 2,2'dioctyloxy-5,5 '-di-tert-butoxanilide, 2,2'-didodecyloxy-5,5 '-di-tert-butyloxanilide, 2-ethoxy-2'-ethyloxanilide, N,N'-bis(3-dimethylaminopropyl) oxamide, 2-ethoxy-5-tert-butyl-2'-ethyloxanilide and its mixture with 2-ethoxy-2'-ethyl-5,4'-di-tert-butoxanilide, mixtures of o- and p-methoxy disubstituted oxanilides and mixtures of o- and p-ethoxy disubstitutoctyloxyphenyl-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)-phenyl]-4,6-bis(2,4-dimethylphenyl)-1,3,5-triazine, 2-[4-dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy) phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, and CYAGARD® UV-1164L Light Stabilizer, commercially available from CYTEC INDUSTRIES, and mixtures thereof;

(c) Metal deactivators, such as N,N'-diphenyloxamide, N-salicylal-N'-salicyloyl hydrazine, N,N'-bis (salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide, and mixtures thereof;

(d) Phosphites and phosphonites including peroxide decomposers, such as alkyl phosphites, aryl phosphites, and aralkyl phosphites, such as triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite ULTRANOX® 618 Antioxidant, bis-(2,4-di-tert-butylphenyl)pentaerythritoldiphosphite ULTRANOX® 626 Antioxidant, commercially available from GE Specialty Chemicals of Parkersburg, W.Va., tris(2,4-di-tert-butylphenyl)phosphite, diisodecyl pentaerythritol diphosphite, bis(2,6-di-tert-butyl-4-methylphenyl)pentaerythritol diphosphite, bis (isodecyloxy)pentaerythritol diphosphite, bis(2,4-di-tert-butyl-6-methylphenyl)pentaerythritol diphosphite, bis(2,4,6-tris(tert-butyl)phenyl)pentaerythritol diphosphite, tristearyl sorbitol triphosphite, tetrakis(2, 4-di-tert-butylphenyl)-4,4'-biphenylene diphosphonite, 6-isooctyloxy-2,4,8,10-tetra-tert-butyl-12H-dibenzo[d, g]-1,3,2-dioxaphosphocin, 6-fluoro-2,4,8,10-tetra-tert-butyl-12-methyl-dibenzo[d,g]-1,3,2-dioxaphosphocin, bis(2,4-di-tert-butyl-6-methylphenyl)methylphosphite, bis(2,4-di-tert-butyl-6-methylphenyl)ethylphosphite, and mixtures thereof;

(e) Hydroxylamines, such as N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecyl-hydroxylamine, -heptadecyl-N-octadecylhydroxylamine, N,N-dialkylhydroxylamine derived from hydrogenated tallow fatty amines, and mixtures thereof;

(f) Nitrones, such as N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecyl nitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrones derived from N,N-dialkylhydroxylamines prepared from hydrogenated tallow fatty amines, and mixtures thereof;

(g) Thiosynergists, such as dilauryl thiodipropionate and distearyl thiodipropionate, and mixtures thereof;

(h) Peroxide scavengers such as esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis (β-dodecylmercapto)propionate, and mixtures thereof;

(i) Polyamide stabilizers, such as copper salts in combination with iodides and/or phosphorus compounds and salts of divalent manganese, and mixtures thereof;

(j) Basic co-stabilizers, such as melamine, polyvinylpyrrolidone, dicyandiamide, triallyl cyanurate, urea compounds, hydrazine compounds, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate, tin pyrocatecholate, and mixtures thereof;

(k) Nucleating agents including inorganic substances, such as talc and metal oxides (e.g., titanium oxide or magnesium oxide), and phosphates, carbonates and sulfates of, preferably, alkaline earth metals; organic compounds, such as mono- or polycarboxylic acids and salts thereof, for example 4-tert-butylbenzoic acid, adipic acid, diphenylacetic acid, sodium succinate and sodium benzoate; polymeric compounds such as ionic copolymers ("ionomers"), and mixtures thereof;

(l) Fillers and reinforcing agents, such as calcium carbonate, silicates, glass fibers, asbestos, talc, kaolin, mica, barium sulfate, metal oxides and hydroxides, carbon black, graphite, wood flour and flours or fibers from other natural products, and synthetic fibers, and mixtures thereof;

(m) Benzofuranones and indolinones, such as those disclosed in U.S. Pat. Nos. 4,325,863, 4,338,244, 5,175,312, 5,216,052, and 5,252,643, and DE-A-4316611, DE-A-4316622, DE-A-4316876, EP-A-0589839 and EP-A-0591102; 3-[4-(2-acetoxy-ethoxy)phenyl]-5,7-di-tert-butyl-benzofuran-2-one, 5,7-di-tert-butyl-3-[4-(2-stearoyloxyethoxy)-phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, and mixtures thereof;

(n) Sulfur containing antioxidants, such as organic sulfides and disulfides and include distearyl thiodipropionate CYANOX® STDP Antioxidant, commercially available from CYTEC INDUSTRIES, pentaerythritol tetrakis(beta-laurylthiopropionate) SEENOX® 412 S Antioxidant, commercially available from Witco Chemical Corporation of Brooklyn, N.Y., and mixtures thereof. A person skilled in the art is well aware, for example, that any one or more of these additives may be combined, such as in CYANOX® 2777 Antioxidant, commercially available from CYTEC INDUSTRIES, which combines a phenolic antioxidant and a phosphite antioxidant. The composition may contain quenchers such as CYASORB® UV-1084 Light Stabilizer, CYASORB® UV-531 Light Stabilizer, each commercially available from CYTEC INDUSTRIES.

(o) Other additives, such as acid scavengers, antistatic agents, blowing agents, catalysts, clarifying agents, emulsifiers, fillers, flameproofing agents, fluorescent whitening agents, infrared absorbers, levelling assistants, lubricants, metal deactivators, mold release agents, nucleating agents, optical brighteners, pigments, plasticizers, rheological additives, and mixtures thereof.

The present invention also contemplates an additive composition comprising the HALS of formula (I), (II), or (III) and at least one of the aforementioned additives. The amount of the HALS to the other additives is from about 500:1 to 1:500 by weight.

The total amount of additives may be present in an amount up to about 10 percent, preferably from about 0.1 percent to about 5 percent by weight, and more preferably from about 0.2 percent to 3 percent by weight, based on the weight of the polymer.

The light-stabilized polymeric article may be formed from a polymeric material by incorporating the presently claimed compounds into polymeric materials, either chemically or physically. Non-limiting examples of polymeric materials that may be so stabilized are polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof.

The degradable polymer may be any polymer requiring stabilization, and includes homopolymers and copolymers of various monomers. It may be an addition polymer, a condensation polymer, a graft polymer, a thermosetting polymer, a photopolymer, a polymer blend or a thermoplastic polymer. It may be in the form of a fiber, a polymer film such as polypropylene films, a thin film such a solvent based coating, a water-based coating, a stoving lacquer, a powder coating, a gel coat, and the like, or it may be in the form of a molded article. Examples of degradable polymers which can be stabilized include, but are not limited to:

1. Homo- and copolymers of monoolefins and diolefins including, but not limited to, ethylene, propylene, isobutylene, butene, methylpentene, hexene, heptene, octene, isoprene, butadiene, hexadiene, dicyclopentadiene, ethylidene, and cycloolefins such as cyclopentene and norbornene; for example, polyethylenes (which optionally can be cross-linked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE) or polypropylene (PP) or polymers of ethylene propylene diene monomer (EPDM); and blends thereof.

2. Copolymers of one or more monoolefins and/or diolefins with carbon monoxide and/or with other vinyl monomers, including acrylic and methacrylic acid, acrylates and methacrylates, acrylamides, acrylonitriles, styrenes, vinyl acetate (such as ethylene/vinyl acetate copolymers (EVA)), vinyl halides, vinylidene halides, maleic anhydride, and allyl monomers such as allyl alcohol, allyl amine, allyl glycidyl ether and compounds thereof; and blends thereof.
3. Hydrocarbon resins (such as $C_5$–$C_9$) including hydrogenated modifications thereof, and mixtures of polyalkylenes and starch; and blends thereof.
4. Homo- and copolymers of styrenes such as styrene, p-methylstyrene and α-methylstyrene such as polystyrene, polyalphamethylstyrene, high impact polystyrene (HIPS); and blends thereof.
5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine, allyl glycidyl ether; and blends thereof.
6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; acrylonitrile/styrene/acrylonitrile polymers (ASA) styrene and acrylonitrile on ethylene/propylene/diene copolymers; styrene and acrylonitrile on polyalkyl acrylates or methacrylates; and styrene and acrylonitrile on acrylate/butadiene (ABS) copolymers; and blends thereof.
7. Halogen-containing polymers such as poly vinyl chloride (PVC), chlorinated polyethylene (CPE), or polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride, other vinyl monomers or other polyvinyl halides; and blends thereof.
8. Homo- and copolymers derived from α,β-unsaturated acids and compounds thereof such as acrylic acid, methacrylic acid, acrylates, methacrylates, acrylamides and acrylonitriles; and blends thereof.
9. Copolymers of the monomers mentioned in (5) above with other unsaturated monomers such as olefins and diolefins (e.g., butadiene), styrenes, vinyl halides, maleic anhydride and allyl monomer such as allyl alcohol, allyl amine, allyl glycidyl ether; and blends thereof.
10. Homo- and copolymers derived from unsaturated alcohols and amines or the acyl compounds or acetals thereof, such as vinyl alcohol (including polyvinyl alcohol crosslinked polyvinyl alcohol), vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenic unsaturated monomers mentioned above; and blends thereof.
11. Homo- and copolymers of cyclic ethers such as alkylene glycols and alkylene oxides, as well as copolymers with bisglycidyl ethers; and blends thereof.
12. Polyacetals such as polyoxymethylene (POM) and those polyoxymethylenes which contain ethylene oxide as a comonomer; and polyoxymethylenes modified with thermoplastic polyurethanes, acrylates and/or MBS; and blends thereof.
13. Polyphenylene oxides (PPO) and sulfides; and blends thereof.
14. Polyurethanes (PUR) derived from hydroxy-functional components such as polyhydric alcohols, polyethers, polyesters, polyacrylics and/or polybutadienes on the one hand, and aliphatic and/or aromatic isocyanates on the other, as well as precursors thereof including isocyanate cross-linked polymers; and blends thereof.
15. Polyamides (PA) and copolyamides derived from diamines, dicarboxylic acids and/or aminocarboxylic acids or the corresponding lactams, such as NYLON® plastics, e.g., polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyepoxides, polyethylene glycol, polypropylene glycol or polytetramethylene glycol; and polyamides condensed during processing (RIM polyamide systems); and blends thereof.
16. Polyureas, polyimides, polyamide-imides, polyetherimides, polyesterimides, polyhydantoins and polybenzimidazoles; and blends thereof.
17. Polyesters derived from dicarboxylic acids, diols and/or hydroxycarboxylic acids or the corresponding lactones, such as polyethylene terephthalate (PET), polybutylene terephthalate (PBT), polyethylene terephthalate, glycol modified (PETG), polyethylene terephthalate modified with 1,4-cyclohexanedimethanol (PCTG),poly-1,4-dimethylcyclohexane terepthalate and polyhydroxybenzoates, as well as block copolyether esters derived from hydroxyl-terminated ethers; and also polyesters modified with polycarbonate or MBS; PEN, PTT; and blends thereof.
18. Polycarbonates (PC) and polyester carbonates such as resins are polycarbonates based on dihydric phenols such as 2,2-bis-(4-hydroxyphenyl)propane (bisphenol A); 2,4-bis (4-hydroxyphenyl)-2-methylbutane; 1,1-bis-(4-hydroxyphenyl)-cyclohexane; 2,2-bis-(3-chloro-4-hydroxyphenyl)propane; 4,4'-sulfonyldiphenol; and 1,1-bis-(4-hydroxyphenyl)-3,3,5-trimethylcyclohexane; and blends thereof. Also preferred are polycarbonate copolymers incorporating two or more phenols, branched polycarbonates wherein a polyfunctional aromatic compound is reacted with a dihydric phenol(s) and carbonate precursor, and polymer blends of which polycarbonate comprises a significant portion of the blend (i.e., more than 20%, preferably more than 50%). Preferred resins for both layers are polycarbonates based on bisphenol A.

U.S. Pat. No. 5,288,788 also describes polycarbonates and polyester carbonates, especially aromatic polycarbonates, for example those based on 2,2-bis(4-hydroxyphenyl) propane or 1,1-bis(4-hydroxyphenyl)cyclohexane. Mixtures (polyblends) of such polymers with one another or with other polymers, for example with polyolefins, polyacrylates, polydienes or other elastomers in the form of impact strength modifiers can also be stabilized with the HALS compounds of the invention.

Among those compounds, preference is given to the polycarbonates, polyesters, polyamides, polyacetals, polyphenylene oxides and polyphenylene sulfides, but especially to the polycarbonates. Those compounds are to be understood as being especially those polymers the constitutional repeating unit of which corresponds to the formula:

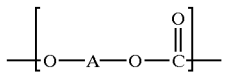

wherein A is a divalent phenolic radical. Suitable examples of A are given in U.S. Pat. No. 4,960,863 and DE-A-3 922,496 whose contents are incorporated herein by reference thereto. "A" can be derived, for example, from hydroquinone, resorcinol, dihydroxybiphenylene or bisphenols in the broadest sense of the term, such as bis (hydroxyphenyl)alkanes, cycloalkanes, sulfides, ethers, ketones, sulfones, sulfoxides, a,a'-bis(hydroxyphenyl)-diisopropylbenzenes, for example the compounds 2,2-bis(4-hydroxyphenyl)propane, 2,2-bis(3,5-dimethyl-4-hydroxyphenyl)-propane, 2,2-bis(3,5-dichloro-4-hydroxyphenyl) propane, 1,1-bis(4-hydroxypehnyl)cyclohexane, or from the compounds of the formula:

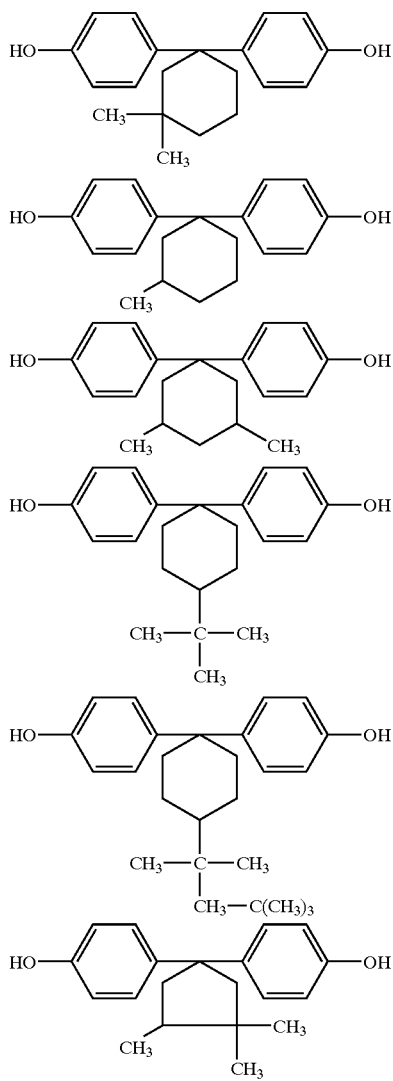

-continued

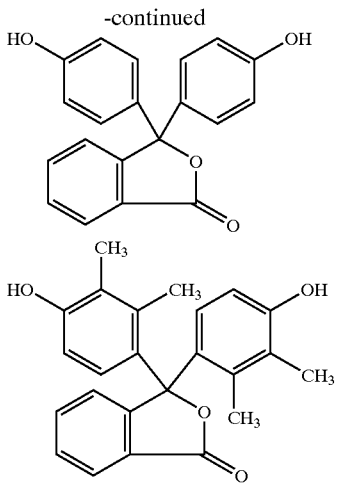

19. Polysulfones, polyether sulfones and polyether ketones.
20. Cross-linked polymers derived from aldehydes condensation resins such as phenol/formaldehyde resins, urea/formaldehyde resins and melamine/formaldehyde resins; and blends thereof.
21. Drying and non-drying alkyd resins; and blends thereof.
22. Unsaturated polyester resins derived from copolyesters of saturated and unsaturated dicarboxylic acids with polyhydric alcohols and vinyl compounds as crosslinking agents, and also halogen-containing modifications thereof; and blends thereof.
23. Cross-linkable acrylic resins derived from substituted acrylates such as epoxy acrylates, hydroxy acrylates, isocyanato acrylates, urethane acrylates or polyester acrylates; and blends thereof.
24. Alkyd resins, polyester resins and acrylate resins cross-linked with melamine resins, urea resins, isocyanates, isocyanurates, carbamates or epoxy resins; and blends thereof.
25. Cross-linked epoxy resins derived from aliphatic, cycloaliphatic, heterocyclic and/or aromatic glycidyl compounds such as bisphenol A and bisphenol F, which are cross-linked with customary hardeners such as anhydrides or amines; and blends thereof.
26. Natural polymers such as cellulose, rubber, gelatin and chemically modified homologous compounds thereof, including cellulose acetates, cellulose propionates and cellulose butyrates, nitrocellulose, or the cellulose ethers such as methyl cellulose, as well as rosins and their compounds; and blends thereof.
27. Polysiloxanes; and blends thereof.
28. Michael addition polymers of amines or blocked amines (e.g., ketimines) with activated unsaturated and/or methylene compounds such as acrylates and methacrylates, maleates and acetoacetates; and blends thereof.
29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6,6 and copolymers, PA/HDPE, PP/HDPE, PP/LDPE, LDPE/HDPE, LDPE/EVA, LDPE/EAA, PA/PP, PA/PPO, PBT/PC/ABS, PBT/PET/PC and the like.
30. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.
31. Aqueous emulsions of natural or synthetic rubber such as natural latex or latexes of carboxylated styrene/butadiene copolymers; and blends thereof.
32. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines; and blends thereof.
33. Radiation curable compositions containing ethylenically unsaturated monomers or oligomers and a polyunsaturated aliphatic oligomer; and blends thereof.
34. Epoxymelamine resins such as light-stable epoxy resins cross-linked by an epoxy functional coetherified high solids melamine resin. The aminoresin-cross-linked polymer may be an aminoresin-cross-linked thermoset acrylic or an aminoresin-cross-linked thermoset polyester. The suitable aminoresins include alkylated and unalkylated melamine-formaldehyde resins, guanamine-formaldehyde resins, urea-formaldehyde resins, glycouril formaldehyde resins, and the like; and blends thereof.
35. Organic dyes such as azo dyes (diazo, triazo, and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles, and perylene tetracarboxylic diimides; and blends thereof.
36. Cosmetic products, such as skin lotions, collagen creams, sunscreen, facial make-up, etc., comprising synthetic materials such as antioxidants, preservatives, lipids, solvents surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc; and blends thereof.
37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc., and combinations thereof.
38. Photographic film paper.
39. Ink.

The term "copolymer," as used herein, is a polymer of two or more different monomers. Preferably, the light-stabilized polymeric material is formed from a polyolefin homopolymer or copolymer, and more preferably a homopolymer or copolymer of polyethylene or polypropylene.

The novel HALS of the present invention can also be employed in multilayer systems. In such systems, a polymer composition having from about 0.1 to 20 percent by weight and preferably having a relatively high content of the novel HALS of the invention, for example, from about 5 to 15 percent by weight, is applied in a thin film (typically between about 5 to 500 $\mu$m and preferably from about 10 to 100 $\mu$m thick) to a shaped article made from a polymer containing little or no ultraviolet stabilizers. Such composition may be applied at the same time as the shaping of the base structure, for example by coextrusion. Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to 20 percent, preferably about 1 to 15 percent and more preferably about 2 to 10 percent by weight of the outer layer composition, of at least one of the HALS of the present invention.

British Patent Appn. No. 2,290,745 describes a number of methods that have been developed to concentrate UV absorbers near or at the surface of polymeric materials. These include surface impregnation (see U.S. Pat. Nos. 3,309,220, 3,043,709, 4,481,664 and 4,937,026) and coating a plastic article with solutions containing thermoplastic resins and UV absorbers (see U.S. Pat. Nos. 4,668,588 and 4,353,965). Both techniques, however, suffer from drawbacks such as requiring additional processing steps (i.e., applying, drying or curing), and encounter difficulties associated with the handling of large processed articles. An additional drawback, particularly relevant to polycarbonate sheet production, is the detrimental effect such post addition treatment would have on the surface of the polymeric substrate.

As described in the U.S. Pat. No. 5,445,872, application of surface layers via coextrusion takes place in a known manner with known coextrusion equipment as taught in U.S. Pat. Nos. 3,487,505 and 3,557,265, which is a preferred way to incorporate HALS compounds onto the surface of a polymeric article according to the present invention. Coextrusion is a well recognized method of producing laminated thermoplastic materials by simultaneously extruding various numbers of layers which form a single composite material. U.S. Pat. No. 4,540,623 describes coextruded materials of at least forty layers. Other methods known to those of ordinary skill in the art produce as few as two or three different layers.

In one embodiment, the invention relates to thermoplastic articles coated with a thermoplastic layer about 0.1 to 10 mil (0.00254 mm to 0.254 mm) thick, preferable about 0.1 to 5 mil (0.00254 mm to 0.127 mm) thick, in which the layer contains between about 0.1% to 20% by weight of one or more of the HALS of the invention. Preferred concentrations are from about 2% to 15% by weight; most preferred are concentrations from about 5% to 10% by weight.

The HALS of the instant invention may be incorporated into the thermoplastics of the surface layer by standard methods, such as dry mixing the additives with a granular resin prior to extruding. The HALS layer may be applied to one or more sides of a thermoplastic article according to the present invention.

Laminated thermoplastic articles corresponding to the present invention which contain additional layers such as a water resistant layer, as found in U.S. Pat. No. 4,992,322, are also within the scope of the present invention.

The core layer and the coating layer may be of the same thermoplastic resin or different. Examples of thermoplastic resins include thermoplastic polyesters, polyester carbonates, polyphenylene oxide, polyvinyl chloride, polypropylene, polypropylene, polyethylene, polyacrylates, polymethacrylates and copolymers and blends such as styrene and acrylonitrile on polybutadiene and styrene with maleic anhydride; and blends thereof.

The polymers stabilized in this way are notable for high weathering resistance, especially for high resistance to UV light. This enables them to substantially retain their mechanical properties and their color and gloss for a long time even when used in harsh environments.

Coating Stabilizers Including HALS Compounds and Preparation of the Same

In another embodiment of the present invention, novel mixtures comprising at least one HALS of the invention can be used as stabilizers for coatings, for example for paints. Of particular interest are coatings and paints for the automobile industry. "Coating" means a free flowing composition that can be applied to the surface of an article in a thin film that then hardens to form a substantially solid surface on the article. Typically, the coating provides an interface between the article and the environment.

Such novel coating compositions comprise from about 0.01 to 20 percent, preferably from about 0.01 to 10 percent and more preferably from about 0.02 to 5 percent by weight of one or more of the HALS of the present invention.

The coating may be applied to the surface of the article in one or more than one layer to provide a multilayered system. In multilayer systems, the concentration of the novel HALS compounds in the outer layer can be relatively high, for example from about 0.01 to 20 percent, preferably from about 0.01 to 10 percent, and more preferably from about 0.02 to 5 percent by weight.

The use of the novel stabilizer in coatings is accompanied by the additional advantage that it inhibits or prevents delamination, i.e., the flaking-off of the coating from the substrate. This advantage is particularly important in the case of metallic substrates, including multilayer systems on metallic substrates, which have such flaking tendencies.

The coatings typically include a binder that suspends pigments and other additives in the coating and allows attachment of the coating to the substrate.

The binder can in principle be any binder which is customary in industry, for example those described in Ullmann's Encyclopedia of Industrial Chemistry, 5th Edition, Vol. A18, pp. 368–426, VCH, Weinheim, 1991, which is incorporated herein by reference. In general, it is a film-forming binder based on a thermoplastic or thermosetting resin, predominantly on a thermosetting resin. Examples thereof are alkyd, acrylic, polyester, phenolic, melamine, epoxy, and polyurethane resins, and mixtures thereof.

Such binders can be a cold-curable or hot-curable binder. Further, in some systems it may be advantageous to add a curing catalyst to such systems. Suitable catalysts which accelerate curing of the binder are described, for example, in Ullmann's Encyclopedia of Industrial Chemistry, Vol. A18, p. 469, VCH Verlagsgesellschaft, Weinheim, 1991, which is incorporated herein by reference.

Preferred binders include those which comprise a functional acrylate resin and a crosslinking agent.

A wide variety of binders may be employed in such coating systems. Examples of suitable coating compositions containing specific binders, include but are not limited to:

1. paints based on cold- or hot-cross-linkable alkyd, acrylate, polyester, epoxy or melamine resins, or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates; or mixtures thereof;
3. one-component polyurethane paints based on blocked isocyanates, isocyanurates or polyisocyanates which are deblocked during baking;or mixtures thereof;
4. two-component paints based on (poly)ketimines and aliphatic or aromatic isocyanates, isocyanurates or polyisocyanates; or mixtures thereof;
5. two-component paints based on (poly)ketimines and an unsaturated acrylate resin or a polyacetoacetate resin or a methacrylamidoglycolate methyl ester; or mixtures thereof;
6. two-component paints based on carboxyl- or amino-containing polyacrylates and polyepoxides; or mixtures thereof;
7. two-component paints based on acrylate resins containing anhydride groups and on a polyhydroxy or polyamino component; or mixtures thereof;
8. two-component paints based on (poly)oxazolines and acrylate resins containing anhydride groups, or unsaturated acrylate resins, or aliphatic or aromatic isocyanates, isocyanurates or polyisocyanates; or mixtures thereof;
9. two-component paints based on unsaturated polyacrylates and polymalonates; or mixtures thereof;
10. thermoplastic polyacrylate paints based on thermoplastic acrylate resins or externally crosslinking acrylate resins in combination with etherified melamine resins; or mixtures thereof;
11. paint systems based on siloxane-modified or fluorine-modified acrylate resins or mixtures thereof;.

In addition to the binder and novel HALS of the present invention, the coating composition according to the invention may further comprise one or more additional additives, such as an antioxidant or additional ultraviolet light absorber or stabilizer. Additional additives include, but are not limited to, those specifically listed above. The additional additive is employed in coating compositions in an amount of from about 0.01 to 5 percent, preferably from about 0.02 to 2 percent by weight.

In addition, well known to those of ordinary skill in the art to be suitable for coating compositions the coating composition can also comprise further components including, but not limited to, solvents, pigments, dyes, plasticizers, stabilizers, thixotropic agents, drying catalysts and/or leveling agents, or combinations thereof. Examples of possible components are those described in Ullmann's Encyclopedia of Industrial Chemistry, 5th Edition, Vol. A18, pp. 429–471, VCH, Weinheim 1991, which is incorporated herein by reference.

Exemplary drying catalysts or curing catalysts are, for example, organometallic compounds, amines, amino-containing resins and/or phosphines.

Examples of organometallic compounds are metal carboxylates, especially those of the metals Pb, Mn, Co, Zn, Zr or Cu, or metal chelates, especially those of the metal Al, Ti or Zr, or organometallic compounds such as organotin compounds, for example, and mixtures thereof.

Examples of metal carboxylates are the stearates of Pb, Mn or Zn, the octoates of Co, Zn or Cu, the naphthenates of Mn and Co or the corresponding linoleates, resinates or tallates, and mixtures thereof.

Examples of metal chelates are the aluminum, titanium, or zirconium chelates of acetylacetone, ethyl acetylacetate, salicylaldehyde, salicylaldoxime, o-hydroxyacetophenone, or ethyl trifluoroacetylacetate, and the alkoxides of these metals, and mixtures thereof.

Examples of organotin compounds are dibutyltin oxide, dibutyltin dilaurate or dibutyltin dioctoate, and mixtures thereof.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof, and mixtures thereof. Further examples are quaternary ammonium salts, for example trimethylbenzylammonium chloride. Amino-containing resins are simultaneously a binder and a curing catalyst. Examples thereof are amino-containing acrylate copolymers.

The curing catalyst used can also be a phosphine, for example triphenylphosphine.

The novel coating compositions can also be radiation-curable coating compositions. In this case, the binder includes monomeric or oligomeric compounds containing ethylenically unsaturated bonds, which after application are cured by actinic radiation, i.e., converted into a crosslinked, high molecular weight form. Where the system is UV-curable, it generally contains a photoinitiator as well. Corresponding systems are described in the above-mentioned publication Ullmann's Encyclopedia of Industrial Chemistry, 5th Edition, Vol. A18, pages 451–453, which is incorporated herein by reference. In radiation-curable coating compositions, the novel stabilizers can also be employed with or without additional UV light stabilizers, including sterically hindered amines.

The coating compositions according to the invention can be applied to any desired substrates, for example to metal, wood, plastic, or ceramic materials. They are preferably used as topcoats in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by any conventional methods available to those or ordinary skill in the art, for example by brushing, spraying, pouring, dipping, or electrophoresis; see also Ullmann's Encyclopedia of Industrial Chemistry, 5th Edition, Vol. A18, pp. 491–500, which is incorporated herein by reference.

Depending on the binder system, the coatings can be cured at room temperature or may require heating. The coatings are preferably cured at a temperature of from about 50° C. to 150° C., and in the case of powder coatings, even at higher temperatures.

The coatings obtained in accordance with the invention generally have excellent resistance to the damaging effects of light, oxygen, and heat. In particular, the presently claimed coatings provide good light stability and weathering resistance.

The invention therefore encompasses coatings, in particular a paint, which has been stabilized against the damaging effects of light, oxygen, and/or heat by a content of at least one of the HALS of the present invention incorporated into or onto an article. The paint may be a pigmented mono-coat which includes a film-forming binder and an organic pigment or dye, an inorganic pigment, a metallic pigment, or a mixture thereof. The paint may also be a composition which comprises a primer in adhesion to a metal or plastic substrate; a pigmented base coat that is in adhesion to the primer, and which comprises a film-forming binder and an organic pigment or dye, an inorganic pigment, a metallic pigment, or a mixture thereof; and a clear top coat that is in adhesion to the base coat, and which comprises a film-forming binder and optionally a transparent pigment. The paint is preferably a topcoat for automobiles.

The invention furthermore relates to a process for stabilizing a coating based on organic polymers against damage by light, oxygen, and/or heat, which comprises mixing with the coating composition a mixture comprising one or more HALS of the present invention, as well as the use of mixtures comprising the one or more HALS of the present invention in coating compositions as stabilizers against damage by light, oxygen, and/or heat.

The coating compositions can comprise an organic solvent or solvent mixture in which the binder is soluble. The coating composition can otherwise be an aqueous solution or dispersion. The carrier can also be a mixture of organic solvent and water. The coating composition may be a high-solids paint or can be solvent-free (e.g., a powder coating material).

The pigments can be inorganic, organic or metallic pigments. The novel coating compositions preferably contain no pigments and preferably are used in clearcoat compositions.

Likewise preferred is the use of the coating composition as a topcoat for applications in the automobile industry, especially as a pigmented or unpigmented topcoat of the paint finish. Its use for underlying coats, however, is also possible.

EXAMPLES

The following examples are merely illustrative of preferred embodiments of the present invention and are not to be construed as limiting the invention, the scope of which is defined by the appended claims.

Examples 1–9
Preparation of HALS Compounds Based on Multifunctional Carbonyl Compounds Eight HALS compounds of the general structure depicted below were synthesized according to the invention.

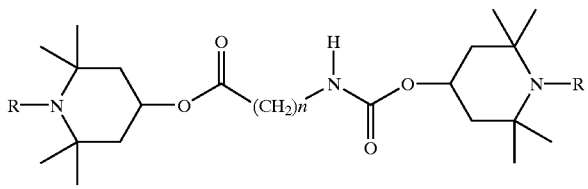

Compound I (n = 5, R = hydrogen)
Compound II (n = 5, R = methyl)
Compound III (n = 11, R = hydrogen)
Compound IV (n = 11, R = methyl)

Compound V

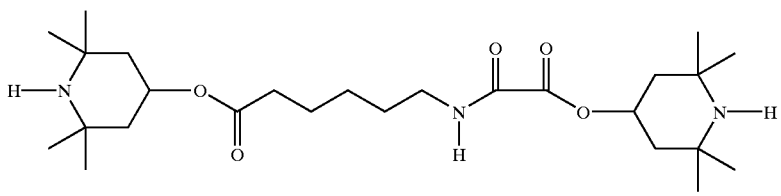

-continued

Compound VI

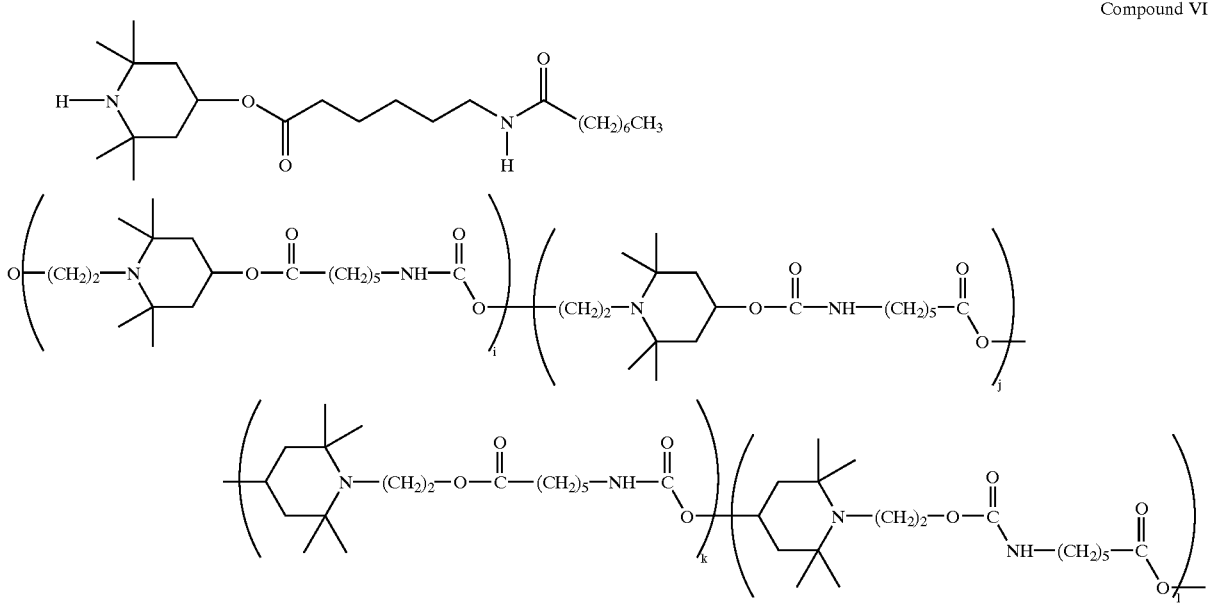

wherein i, j, k, and l are integers and the sum of i, j, k and l is greater than 2.
Compound VII (Mn = approximately 2,000)
Compound VIII (Mn = approximately 8,800)

Compounds I and II were prepared from methyl 6-(methoxycarbonylamino) hexanoate (Compound A), compounds III and IV were prepared from butyl 6-butoxycarbonylaminoundecanoate (Compound B), compound V was prepared from methyl 6-[(methoxyoxoacetyl) amino]-hexanoate (Compound C) and compound VI was prepared from methyl 6-(octanoylamino)hexanoate (Compound D). Compounds VII and VIII were prepared from compound A and N-(2-hydroxyethyl)-2,2,6,6-tetramethyl-4-piperidinol.

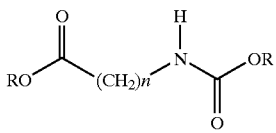

Compound A (n = 5, R = methyl)
Compound B (n = 11, R = butyl)

Compound C

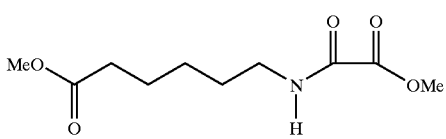

Compound D

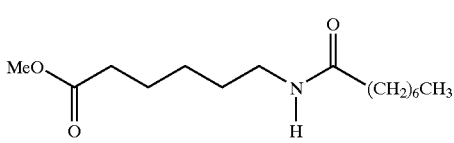

N-(2-hydroxyethyl)-2,2,6,6-tetramethyl-4-piperidinol was prepared by the hydrolysis of TINUVIN 622 with aqueous sodium hydroxide/tetrahydrofuran, removal of the tetrahydrofuran under reduced pressure, extraction of the aqueous layer with chloroform, drying and filtering the chloroform layer, and removal of the chloroform under reduced pressure. The recovered N-(2-hydroxyethyl)-2,2,6, 6-tetramethyl-4-piperidinol had a melting point of 179–183° C. (literature melting point 182° C., DE 2,352,658). The synthesis of Compounds A, B, C and D are described below.

Synthesis of Compound A

To a 300 mL 3-necked round bottom flask equipped with a mechanical stirrer, a ground glass stopper and a condenser fitted with an argon inlet and outlet to a bubbler was charged 10 g (88 mmol) of caprolactam, 10.5 g (117 mmol) of dimethylcarbonate, 5.23 g (96.8 mmol) of sodium methoxide, and 100 mL of methanol. The mixture was heated at reflux for 24 hours, then cooled to room temperature. 7.3 g (121 mmol) of glacial acetic acid was added and the methanol removed by rotary evaporation. The residue was dissolved in 100 mL of methylene chloride and the organic layer extracted with water to remove unreacted caprolactam. Solvent removal by rotary evaporation, followed by further solvent removal in vacuo (<1 mm) at 95° C. gave 5.23 g (29%) of compound A as a nearly colorless oil. The structure of compound A was established by NMR. $^1$H NMR (CDCl$_3$): $\delta$4.63 (br s, 1H, NH); 3.68 (s, 3H, CH$_3$—OCO); 3.66 (s, 3H, CH$_3$—OCO); 3.17 (br dt, 2H, —C$\underline{H}_2$—NH—); 2.31 (t, 2H, —CH$_2$COO); 1.65–1.21 (m, 6H, CH$_2$(C$\underline{H}_2$)$_3$CH$_2$).

Synthesis of Compound B

To a three-necked, 250 mL reaction flask equipped with a magnetic stirrer, a reflux condenser, and a thermometer adapter, was charged 13.96 g (0.070 mol) of laurolactam, 13.4 g (0.076 mol) of dibutyl carbonate, 4.16 g (0.077 mol) of sodium methoxide, and 130 g of butanol. The mixture was heated for 64 hours at 110° C. After cooling to room temperature, 4.9 g (0.10 mol) of glacial acetic acid in 30 g of butanol was added and the mixture stirred for 5 min. The resulting mixture was diluted with 500 mL of methylene chloride, washed with water, and dried (MgSO$_4$). Filtration and rotary evaporation gave 19.6 g of a greasy solid. Flash chromatography on 200–400 mesh, 60A silica gel (0.5% methanol/methylene chloride) gave 7.2 g (25%) of the title compound as a white semi-solid. The structure of compound B was established by NMR. $^1$H NMR (CDCl$_3$): $\delta$4.61 (br s, 1H, NH); 4.05 (q, 4H, —CH$_2$CH$_2$—OCO); 3.16 (br dt, 2H, —CH$_2$—NH—); 2.28 (t, 2H, —CH$_2$COO); 1.65–1.21 (m, 26H, CH$_2$(CH$_2$)$_9$CH$_2$, (CH$_2$)$_2$CH$_3$), 0.93 (t, 6H, CH$_3$).

Synthesis of Compound C

To a 100-mL round bottom flask equipped with a stir bar was charged 8.45 g (75 mmol) of caprolactam, 8.85 g (75 mmol) of dimethyl oxalate, and 0.16 g (3 mmol) of sodium methoxide. The mixture was immersed in a 50° C. oil bath and heated for 30 min, then cooled over an hour to 35° C. After stirring at this temperature for several hours, the mixture was cooled and allowed to stand overnight at room temperature. The mixture was diluted with 125 mL of methylene chloride and washed with water, then washed with saturated sodium chloride solution. Drying over molecular sieves, filtration, and removal of solvent under reduced pressure gave 12.5 g (72% yield) of a light yellow liquid which crystallized to a low melting solid on standing. The structure of the material was confirmed by $^1$H NMR analysis. $^1$H NMR (CDCl$_3$): δ7.18 (br s, 1H, NH); 3.90 (s, 3H, CH$_3$—OCOCO); 3.67 (s, 3H, CH$_3$—OCCH$_2$); 3.35 (app q, 2H, —CH$_2$—NH—); 2.32 (t, 2H, —CH$_2$COO); 1.70–1.30 (m, 6H, CH$_2$(CH$_2$)$_3$CH$_2$).

Synthesis of Compound D

To a 100-mL round bottom flask equipped with a stir bar was charged 16.9 g (150 mmol) of caprolactam, 23.7 g (150 mmol) of methyl caprylate and 0.32 g (6 mmol) of sodium methoxide. The mixture was immersed in a 185–195° C. oil bath and heated for 58 hours. After cooling to 75° C. and addition of 0.35 g (6 mmol) of acetic acid the flask was cooled further and residual methyl caprylate (17 g) removed by distillation at 48–67° C./0.8 mm, followed by caprolactam (10 g) at 90–95° C./0.8 mm. The residue was diluted with methylene chloride, washed with water to further remove caprolactam, dried (MgSO$_4$), filtered, and evaporated under reduced pressure to give compound D (6.3 g, 38% yield based on unrecovered caprolactam) as a light brown wax. The structure of the material was confirmed by $^1$H NMR analysis. $^1$H NMR (CDCl$_3$): δ5.60 (br m, 1H, NH); 3.62 (s, 3H, CH$_3$—OCO); 3.20 (app q, 2H, —CH$_2$—NH—); 2.25 (t, 2H, —CH$_2$COO—); 2.16 (t, 2H, —CH$_2$CONH—); 1.70–1.18 (m, 16H, CH$_2$(CH$_2$)$_3$CH$_2$, CH$_2$(CH$_2$)$_5$(CH$_3$).

Synthesis of a Mixture of Compound E and F

To a 50 mL thick-walled reaction vessel equipped with a magnetic stir bar and a Teflon screw cap was added 10.6 g(53.7 mmol) of laurolactam, 9.83 g (56.4 mmol) of dibutyl carbonate, and 0.58 g (10.7 mmol) of sodium methoxide. The mixture was immersed in a 120° C. oil bath and heated for 2 hours. After cooling to room temperature the mixture was diluted with 100 mL of methylene chloride and to it was added 0.67 g (11.2 mmol) of acetic acid. Filtration and solvent removal by rotary evaporation, followed by further solvent removal in vacuo (<1 mm) at 95° C. gave the product as an off-white paste. $^1$H NMR (CDCl$_3$) indicated the presence of mainly two compounds, E and F, in an approximately 80:20 mole ratio. Flash chromatography (3.5% methanol/methylene chloride) gave pure samples of the two components.

Compound E: $^1$H NMR (CDCl$_3$): δ4.61 (br s, 1H, NH) 4.05 (q, 4H, —CH$_2$CH$_2$—OCO); 3.16 (br dt, 2H, —CH$_2$—NH—); 2.28 (t, 2H, -2H, —CH$_2$COO); 1.65–1.21 (m, 26H, CH$_2$(CH$_2$)$_9$CH$_2$, (CH$_2$)$_2$CH$_3$), 0.93 (t, 6H, CH$_3$).

Compound F: $^1$H NMR (CDCl$_3$): δ5.50 (br t, 1H, CH$_2$N HCOCH$_2$); 4.65 (br s, 1H —CH$_2$ NHCOOCH$_2$ 4.05 (q, 4H, —CH$_2$CH$_2$—OCO); 3.21 (dt 2H, —CH$_2$NHCOCH$_2$—); 3.16 (br dt, 2H, —CH$_2$NHCOOCH$_2$); 2.28 (t, 2H, —CH$_2$COO); 2.15 (t, 2H, —CH$_2$CONH); 1.65–1.21 (M, 26H, CH$_2$(CH$_2$)$_9$CH$_2$, (CH$_2$)$_2$CH$_3$), 0.93 (t, H, CH$_3$).

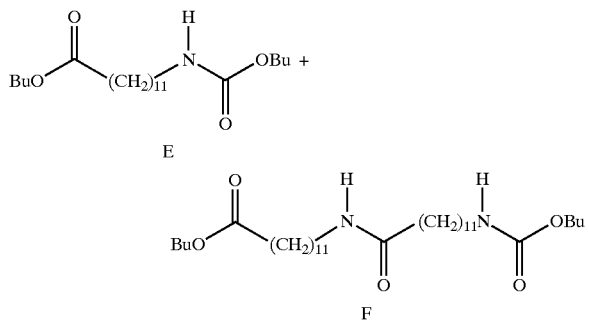

E

F

The lower temperature reaction of these reactants gives little or no compound F.

Synthesis of a Mixture of Compound G and H

To a 50 mL thick-walled reaction vessel equipped with a magnetic stir bar and a Teflon screw cap as added 6.06 g (53.7 mmol) of caprolactam, 9.83 g (56.4 mmol) of dibutyl carbonate, and 0.58 g (10.7 mmol) of sodium methoxide. The mixture was immersed in a 129° C. oil bath and heated for 2 hours. After cooling to room temperature the mixture was diluted with 100 mL of methylene chloride and to it was added 0.67 g (11.2 mmol) of acetic acid. Filtration and solvent removal by rotary evaporation, followed by further solvent removal in vacuo (<1 mm) at 95° C. gave the product as a yellow paste. $^1$H NMR (CDCl$_3$) indicated the presence of compounds G and H in an approximately 80:20 mole ratio.

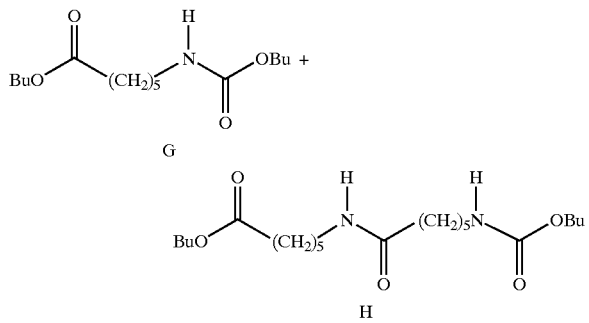

G

H

The lower temperature reaction of these reactants gives little or no compound H.

Synthesis of a Mixture of Compound I and J

To a 25 thick-walled reaction vessel equipped with a magnetic stir bar and a Teflon screw cap was added 2.26 g (20 mmol) of caprolactam, 1.89 g (21 mmol) of dimethyl carbonate, and 54 mg (1.0 mmol) of sodium methoxide. The mixture was immersed in a 130° C. oil bath and heated for ½ hour. After cooling to room temperature the mixture was diluted with 100 mL of methylene chloride and to it was added 0.67 g (11.2 mmol) of acetic acid. Filtration and solvent removal by rotary evaporation, followed by further solvent removal in vacuo (<1 mm) at 95° C. gave the product as a yellow paste. H NMR (CDCl$_3$) indicated the presence of compounds I and J in an approximately 80:20 mole ratio.

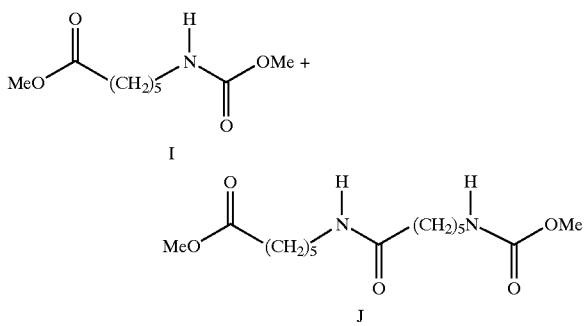

The lower temperature reaction of these reactants gives little or no compound J.

The synthesis of a mixture of Compounds E and F, G and H, and I and J show that, especially at higher temperatures, the multifunctional carbonyl compound can be formed by nucleophilic acyl addition of a lactam anion at the carbonyl of a carbonate to produce an intermediate followed by reaction of a second lactam anion at the lactam carbonyl of the intermediate. The resulting multifunctional carbonyl compounds can then be reacted with a 4-aminopiperidine radical to provide a HALS mixture which is an effective stabilizer. Generally the product produced in the lower temperature reactions are less colored.

Example 1

Preparation of 2,2,6,6-tetramethylpiperidin-4-yl 6-(2,2,6,6-tetramethyl-4-piperidinoxycarbonyl amino)hexanoate (Compound I).

To a 500 mL three-necked flask equipped with a magnetic stirrer, a Dean-Stark trap with a condenser, a thermometer, and a glass stopper was added 20 g (98.4 mmol) of Compound A, 46.3 g (0.295 mol) of 2,2,6,6-tetramethyl-4-piperidinol, and 150 mL of toluene. Under a slow nitrogen flow, 20 mL of toluene was distilled off and the trap drained. The glass stopper was removed and 1.0 g (1.67 mmol) of 1,3-diacetoxy-1,1,3,3-tetrabutyldistannoxane was added. Another 75 mL of toluene was slowly distilled off over 8 hours. After addition of another 110 mL of toluene, 80 mL of toluene was removed over an additional 2 hours. The degree of conversion by NMR analysis was >98%. The mixture was cooled to room temperature and diluted with ether. The organic solution was washed with water to remove excess amino alcohol and dried over sodium carbonate. Filtration and removal of solvent under reduced pressure followed by further solvent removal in vacuo (<1 mm) at 95° C. gave 41.2 g (92%) of Compound I as an white solid, m.p. 59–62° C. The structure of the material was confirmed by $^1$H NMR analysis. $^1$H NMR (CDCl$_3$): δ5.19 (m, 1H, R$_2$CH—OCOCH$_2$—); 5.05 (m, 1H, R$_2$CHOCONH—); 4.63 (br s, 1H, NH); 3.17 (br dt, 2H, —CH$_2$—NH—); 2.28 (t, 2H, —CH$_2$COO); 2.00–1.30 (m, 14H, CH$_2$C(CH$_3$)$_2$, CH(CH$_2$)$_3$CH$_2$, 1.20 (d, 24H, CH$_2$C(CH$_3$)$_2$).

Example 2

Preparation of 1,2,2,6,6-pentamethylpiperidin-4-yl 6-(1,2,2,6,6-pentamethyl-4-piperidinoxycarbonylamino)hexanoate (Compound II).

To a 100 mL three-necked flask equipped with a magnetic stirrer, a Dean-Stark trap with a condenser, a thermometer, and a glass stopper was added 4.85 g (23.9 mmol) of Compound A, 12.2 g (71.6 mmol) of 1,2,2,6,6-pentamethyl-4-piperidinol, and 30 mL of toluene. Under a slow argon flow, 17 mL of toluene was distilled off and the trap drained. The glass stopper was removed and 0.26 g (0.43 mmol) of 1,3-diacetoxy-1,1,3,3-tetrabutyldistannoxane was added. Another 22 mL of toluene was slowly distilled off over 1 hour. After addition of another 10 mL of toluene, 11 mL of toluene was removed over an additional 3 hours. The degree of conversion by NMR analysis was >97%. The mixture was cooled to room temperature and diluted with ethyl acetate. The organic solution was washed with water to remove excess amino alcohol and dried over magnesium sulfate. Filtration and removal of solvent under reduced pressure followed by further solvent removal in vacuo (<1 mm) at 95° C. gave 10.23 g (89%) of Compound II as a nearly colorless viscous oil. The structure of the material was confirmed by $^1$H NMR analysis. $^1$H NMR (CDCl$_3$): δ5.03 (m, 1H, R$_2$CH—OCOCH$_2$—); 4.92 (m, 1H, R$_2$CHOCONH—); 4.68 (br s, 1H, NH); 3.18 (br dt, 2H, —CH$_2$—NH—); 2.28 (t, 2H, —CH$_2$COO —); 2.23 (s, 3H, CH$_3$NC(CH$_3$)$_2$); 1.90–1.35 (in, 14H, CH$_2$(CH$_2$)$_3$CH$_2$, CH$_2$C(CH$_3$)$_2$), 1.13 (d, 24H, CH$_2$C(CH$_3$)$_2$). The TGA T-10% value of Compound II was 237° C.

Example 3

Preparation of 2,2,6,6-tetramethylpiperidin-4-yl 6-(2,2,6,6-tetramethyl-4-piperidinoxycarbonylamino)undecanoate (Compound III).

A 250 mL single-necked reaction flask was equipped with a magnetic stirrer and a distillation head fitted with a thermometer, condenser, and receiving flask with a nitrogen inlet and outlet to a bubbler. To this flask was charged 4.3 g (11.57 mmol) of Compound B, 7.27 g (46.3 mmol) of 2,2,6,6-tetramethyl-4-piperidinol, and 200 mL of xylene. Under a slow nitrogen flow, 25 mL of xylene was distilled off and the trap drained. After lowering the heat source and allowing the mixture to cool to 110° C., 0.17 g (0.28 mmol) of 1,3-diacetoxy-1,1,3,3-tetrabutyldistannoxane was added and the heat source raised. Another 290 mL of xylenes were slowly distilled off over 7 hours, charging 100 mL of xylenes at the 3 hour point. After addition of another 240 mL of xylenes, distillation was continued for another 12 hours, during which time 175 mL was collected. NMR analysis indicated >90% conversion. The mixture was cooled to room temperature and diluted with ether. The organic solution was washed with water to remove excess amino alcohol and dried over magnesium sulfate. Filtration and removal of solvent under reduced pressure followed by further solvent removal in vacuo (<1 mm) at 95° C. gave 5.5 g (83%) of Compound III as a yellow oil. The structure of the material was confirmed by $^1$H NMR analysis. $^1$NMR (CDCl$_3$): δ5.19 (m, 1H, R$_2$CH—OCOCH$_2$—); 5.06 (m, 1H, R$_2$C HOCONH—); 4.62 (br s, 1H, NH); 3.17 (br dt, 2H, —CH$_2$——NH—); 2.25 (t, 2H, —CH$_2$COO); 2.00–1.20 (m, 26H, CH$_2$C(CH$_3$)$_2$, CH$_2$(CH$_2$)$_9$CH$_2$), 1.20 (d, 24H, CH$_2$C(CH$_3$)$_2$).

Example 4

Preparation of 1,2,2,6,6-pentaamethylpiperidin-4-yl 6-(1,2,2,6,6-pentamethyl-4-piperidinoxycarbonylamino) undecanoate (Compound IV).

A 250 mL single-necked reaction flask was equipped with a magnetic stirrer and a distillation head fitted with a thermometer, condenser, and receiving flask with a nitrogen inlet and outlet to a bubbler. To this flask was charged 4.5 g (12.1 mmol) of Compound B, 8.3 g (48.4 mmol) of 1,2,2,6,6-pentamethyl-4-piperidinol, and 200 mL of xylene. Under a slow nitrogen flow, 25 mL of xylene was distilled off and the trap drained. After lowering the heat source and allowing the mixture to cool to 110° C., 0.19 g (0.31 mmol) of 1,3-diacetoxy-1,1,3,3-tetrabutyldistannoxane was added.

Another 450 mL of xylenes were distilled off over 24 hours, adding 100 mL, 100 mL and 150 mL at the 5, 21 and 23 hour points, respectively. The mixture was cooled to room temperature and diluted with ether. The organic solution was washed with water to remove excess amino alcohol, followed by washing with aqueous NaOH and then more water, and finally dried over magnesium sulfate. Filtration and removal of solvent under reduced pressure followed by further solvent removal in vacuo (<1 mm) at 95° C. gave 5.4 g (79%) of Compound IV as a nearly colorless oil. The structure of the material was confirmed by $^1$H NMR analysis. $^1$H NMR (CDCl$_3$): δ5.05 (m, 1H, R$_2$C$\underline{H}$—OCOCH$_2$—); 4.94 (m, 1H, R$_2$C$\underline{H}$OCONH—); 4.65 (br s, 1H, NH); 3.16 (br dt, 2H, —C$\underline{H}_2$—NH—); 2.25 (t, 2H, t, 2H, —CH$_2$COO—); 2.23 (5, 3H, CH$_3$NC(CH$_3$)$_2$); 1.90–1.28 (m, 26H, CH$_2$(C$\underline{H}_2$)$_9$CH$_2$, C$\underline{H}_2$C(CH$_3$)$_2$), 1.10 (d, 24H, CH$_2$C(C$\underline{H}_3$)$_2$).

Example 5

Preparation of 2,2,6,6-tetramethylpiperidin-4-yl 6-[(2,2,6,6-tetramethyl-4-piperidinyloxy)oxoacetyl]amino hexanoate (Compound V).

A 250 mL single-necked reaction flask was equipped with a magnetic stirrer and a Dean-Stark trap fitted with a condenser and nitrogen inlet/outlet. The flask was charged with 10.0 g (43.3 mmol) of compound C, 20.4 g (130 mmol) of 2,2,6,6-tetramethyl-4-piperidinol, and 150 mL of toluene. Under a slow nitrogen flow, 15 mL of toluene was distilled off and the trap drained. After lowering the heat source and allowing the mixture to cool to 110° C., 0.46 g (0.76 mmol) of 1,3-diacetoxy-1,1,3,3-tetrabutyldistannoxane was added and the heat source raised. Another 110 mL of toluene was slowly distilled off over 9 hours, then 25 mL of xylenes were added and 20 mL of additional solvent distilled off over 6 hours. The resulting mixture was cooled to room temperature and diluted with ethyl acetate. The organic solution was washed with water to remove excess amino alcohol and dried over molecular sieves. Filtration and removal of solvent under reduced pressure followed by further solvent removal in vacuo (<1 mm) at 95° C. gave 13.0 g (62%) of Compound V as a yellow oil. The structure of the material was confirmed by $^1$H NMR analysis. $^1$H NMR (CDCl$_3$): δ7.15 (m, 1H, NHCO—); 5.32 (m, 1H, R$_2$CHOCO—); 5.20 (m, 1H, R$_2$CHOCO—); 3.38 (dt, 2H, —C$\underline{H}_2$—NH—); 2.28 (t, 2H, —CH$_2$COO—); 2.05–1.10 (m, 14H, CH$_2$-(C$\underline{H}_2$)$_3$CH$_2$), C$\underline{H}_2$C(CH$_3$)$_2$), 1.20 (d, 12H, CH$_2$C(C$\underline{H}_3$)$_2$); 1.18 (d, 12H, CH$_2$C(C$\underline{H}_3$)$_2$).

Example 6

Preparation of 2,2,6,6-tetramethylpiperidin-4-yl 6-(octanoylamino)hexanoate (Compound VI).

A 250 mL single-necked reaction flask was equipped with a magnetic stirrer and a Dean-Stark trap fitted with a condenser and nitrogen inlet/outlet. To this flask was charged 6.1 g (22.5 mmol) of compound D, 5.29 g (33.7 mmol) of 2,2,6,6-tetramethyl-4-piperidinol, and 150 mL of toluene. Under a slow nitrogen flow, 8 mL of toluene was distilled off and the trap drained. After lowering the heat source and allowing the mixture to cool to 110° C., 0.17 g (0.28 mmol) of 1,3-diacetoxy-1,1,3,3-tetrabutyldistannoxane was added and the heat source raised. Another 100 mL of toluene was slowly distilled off over 16 hours and the resulting mixture was cooled to room temperature and diluted with methylene chloride. The organic solution was washed with water to remove excess amino alcohol and dried over anhydrous sodium carbonate. Filtration and removal of solvent under reduced pressure followed by further solvent removal in vacuo (<1 mm) at 60° C. gave 8.0 g (90%) of Compound VI as a light brown wax. The structure of the material was confirmed by $^1$H NMR analysis. $^1$H NMR (CDCl$_3$): δ5.60 (m, 1H, NHCO—); 5.18 (m, 1H, R$_2$CHOCO—); 3.25 (dt, 2H, —C$\underline{H}_2$—NH—); 2.28 (t, 2H, —CH$_2$COO—); 2.16 (t, 2H, —CH$_2$CONH—); 1.95–1.10 (m, 20H, CH$_2$(C$\underline{H}_2$)$_3$CH$_2$, CH$_2$(C$\underline{H}_2$)$_5$, CH$_2$CH$_2$C(CH$_3$)$_2$); 1.20 (d, 12H, CH$_2$C(C$\underline{H}_3$)$_2$; 0.88 (t, 3H, —CH$_2$C$\underline{H}_3$).

Example 7

Synthesis of Oligomeric HALS Compounds (Compounds VII and VIII).

To a 100 ml 3-necked round bottom flask equipped with a magnetic stirrer, a thermometer and a Dean-Stark trap fitted with a condenser and a nitrogen inlet/outlet to a bubbler was charged 5.45 g (26.8 mmol) of Compound A, 27 mL of toluene, 163 mg (0.27 mmol) of 1,3-diacetoxy-1,1,3,3-tetrabutyldistannoxane, and 5.4 g of N-(2-hydroxyethyl)-2,2,6,6-tetramethyl-4-piperidinol. The mixture was heated so that 13 mL of solvent distilled off over three hours. A 12 mL aliquot was removed from the reaction mixture (Fraction A), and was worked up as described below. The remaining reaction mixture was heated for an additional 2.5 hours, over which time 8 mL of solvent distilled off. After addition of 10 mL of xylenes, the temperature was increased so that 15 mL of additional solvent distilled off over 3 hours. The resulting reaction mixture (Fraction B) was worked up as described below.

Workup of Fraction A: The 12 mL aliquot was diluted with methylene chloride, washed with water, dried (MgSO$_4$), filtered, and the solvent removed under reduced pressure. Further solvent removal in vacuo (<1 mm) at 50–60° C. gave 4.4 g of compound VII as a clear colorless semisolid. High Performance Size-Exclusion Chromatography (HPSEC) gave a value of 2,000 for the number average molecular weight (Mn) of the material using a polystyrene standard. The structure of the material was confirmed by $^1$H NMR analysis. $^1$H NMR (CDCl$_3$): δ5.07 (m, 0.5H, R$_2$-C$\underline{H}$—OCOCH$_2$—); 4.94 (m, 0.5H, R$_2$C$\underline{H}$OCONH—); 4.65 (br s, 1H, NH); 3.92 (app q, 2H, —C$\underline{H}_2$—OCOCH$_2$, —C$\underline{H}_2$—OCONH—); 3.68 (s, 0.44H, —CH$_2$COOC$\underline{H}_3$); 3.66 (s, 0.44H, —NHCOOC$\underline{H}_3$); 3.18 (br m, 2H, —C$\underline{H}_2$—NH—); 2.65 (t, 2H, CH$_2$C$\underline{H}_2$—N); 2.28 (app q, 2H, —CH$_2$COO—); 1.90–1.30 (m, 12H, CH$_2$(C$\underline{H}_2$)$_3$CH$_2$), C$\underline{H}_2$C(CH$_3$)$_2$), 1.10 (d, 12H, CH$_2$C(C$\underline{H}_3$)$_2$)

Workup of Fraction B: The remainder of the reaction mixture was diluted with methylene chloride, washed with water, dried (MgSO$_4$), filtered, and the solvent removed under reduced pressure. Further solvent removal in vacuo (<1 mm) at 80–90° C. gave 4.6 g of compound VIII as a white foam. High Performance Size-Exclusion Chromatography (HPSEC) gave a value of 8,800 for the number average molecular weight (Mn) of the material using a polystyrene standard. The structure of the material was confirmed by $^1$H NMR analysis. $^1$H NMR (CDCl$_3$): δ5.07 (m, 0.5H, R$_2$C$\underline{H}$—OCOCH$_2$—); 4.94 (m, 0.5H, R$_2$-CHOCONH—); 4.65 (br s, 1H, NH); 3.92 (app q, 2H, —C$\underline{H}_2$—OCOCH$_2$, —C$\underline{H}_2$—OCONH—); 3.68 (s, 0.16H, —CH$_2$COOC$\underline{H}_3$); 3.66 (s, 0.16H, —NHCOOC$\underline{H}_3$; 3.18 (br m, 2H, —C$\underline{H}_2$—NH—); 2.65 (t, 2H, CH$_2$C$\underline{H}_2$—N); 2.28 (app q, 2H, —CH$_2$COO—); 1.90–1.30 (m, 12H, CH$_2$-(C$\underline{H}_2$)$_3$CH$_2$), C$\underline{H}_2$C(CH$_3$)$_2$), 1.10 (d, 12H, CH$_2$C(C$\underline{H}_3$)$_2$)

Example 8

Single Step Reaction to Produce 2,2,6,6-tetramethyl-4-piperidine 6-(2,2,6,6-tetramethyl-4-piperidinoxycarbonyl amino)hexanoate (Compound I), Base Catalyzed.

To a 100 mL three-necked round bottom flask equipped with a magnetic stir bar, an addition funnel containing anhydrous toluene, and a Dean-Stark trap fitted with a condenser and a nitrogen inlet/outlet, was charged 1.69 g (15 mmol) of caprolactam, 2.74 g (15.75 mmol) of dibutyl carbonate, 4.94 g (31.5 mmol) of 2,2,6,6-tetramethyl-4-piperidinol, and 50 mL of toluene. The mixture was heated to a heating mantle temperature of 142° C., so that 6 mL of solvent distilled into the trap. The mixture was cooled and 75 mg (1.39 mmol) of sodium methoxide was added to the mixture. The mixture was reheated to boiling and 20 mL distilled into the trap over 4 hours. The trap was drained and 25 mL of toluene was added to the mixture through the addition funnel. After another 25 mL of solvent distilled off over 4 hours, 25 mL of anhydrous xylenes was added, and 35 mL of solvent removed over 6 hours. $^1$H NMR indicated >95% conversion of starting material. Cooling to room temperature, dilution with methylene chloride, washing with water, drying (molecular sieves), filtration, and removal of solvent under reduced pressure gave a yellow oil. Further removal of volatiles at 90° C./0.8 mm gave 5.0 g, 75% yield, of a light yellow semisolid. $^1$H NMR indicated the presence of the desired hindered amine, compound I, with approximately 85% purity.

Example 10

Preparation of Oligomeric HALS from BPIP and Compound A Compound (IX)

To a 250 mL 3-necked round bottom flask equipped with a magnetic stirrer, a thermometer, and a Dean-Stark trap fitted with a condenser and nitrogen inlet/outlet to a bubbler, was charged 5.0 g (24.6 mmol) of Compound A, 100 mL of mixed xylenes, and 9.69 g (24.6 mmol) of N,N'-bis(2,2,6,6-tetramethyl-4-piperidinyl)-1,6-hexanediamine (BPIP). The mixture was heated to reflux for one hour, after which the heat source was lowered, the Dean-Stark trap drained of 30 mL of xylenes which had collected, and 0.22 g (0.37 mmol) of 1,3-diacetoxy-1,1,3,3-tetrabutyldistannoxane was added. The mixture was reheated to the boiling point, and another 50 mL of solvent was allowed to collect over several hours. Another 100 mL portion of anhydrous xylenes was added and distilled off over several hours. The mixture was cooled to room temperature, diluted with methylene chloride, washed with water, dried (molecular sieves), filtered and the solvent removed under reduced pressure to give 12.1 g of compound IX as a tacky yellowish solid.

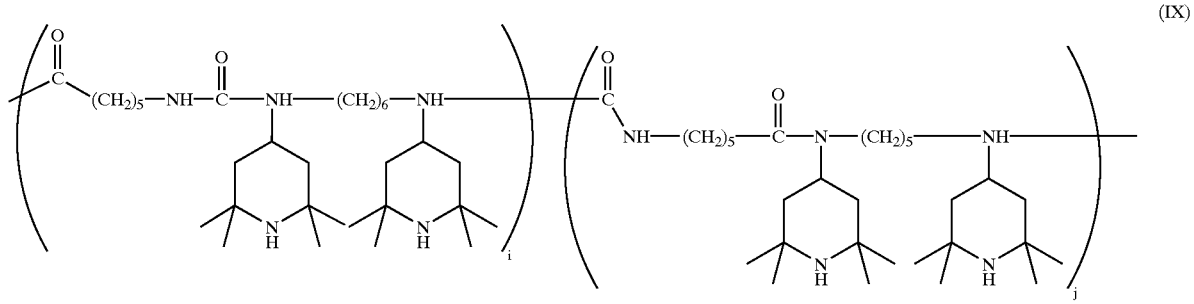

(IX)

Example 9

Single Step Reaction to Produce 2,2,6,6-tetramethyl-4-piperidine 6-(2,2.6,6-tetramethyl-4-piperidinoxycarbonyl amino)hexanoate (Compound I), Lewis Acid Catalyzed.

To a 250 mL three-necked round bottom flask equipped with a magnetic stir bar, and a Dean-Stark trap fitted with a condenser and a nitrogen inlet/outlet, was charged 16.9 g (150 mmol) of caprolactam, 39.2 g (225 mmol) of dibutyl carbonate, 70.65 g (450 mmol) of 2,2,6,6-tetramethyl-4-piperidinol, and 200 mL of toluene. The mixture was heated to a pot temperature of 120° C., so that 12 mL of solvent distilled into the trap. The mixture was cooled, and 0.85 g (3 mmol) of titanium (IV) isopropoxide was added to the mixture. The mixture was reheated to boiling and the pot temperature gradually increased from 120° C. to 210° C. so that solvent distilled off over 20 hours. $^1$H NMR indicated >95% conversion of starting material. The trap was removed and the flask fitted with a distillation head and a condenser with a steam jacket. A solid impurity (28.0 g) distilled over at 75–120° C./0.8 mm. The flask residue was diluted with methylene chloride and to it was added 0.3 mL of water. Overnight stirring at room temperature, filtration, and removal of solvent gave 59.0 g (89% yield) of a thick, light yellow oil. $^1$H NMR indicated the presence of the desired hindered amine I with approximately 90% purity. To this oil was added 30 g hexanes and the mixture heated until homogeneous. After cooling to 5° C. and standing 12 hours at this temperature, filtration afforded 36 g (53% yield) of the desired hindered amine I as a white solid, mp 51–54° C., with a purity by $^1$H NMR of approximately 95%.

wherein i and j are integers and the sum of i and j is greater than or equal to 2. The structure of compound IX was confirmed with $^1$H NMR analysis. $^1$H NMR (CDCl$_3$): δ4.58 (br m, NH); 4.35 (m, R$_2$CHNR$_2$); 3.65 (s, CH$_3$O—); 3.25 (app q, —CH$_2$—NH—); 3.00 (app q, —CH$_2$—NRCO —); 2.89 (m, R$_2$CHNHR); 2.37 (t, 2H, —CH$_2$COO); 1.90–0.89 (m, N—CH$_2$(CH2)$_4$CH$_2$—N, COCH$_2$(CH$_2$)$_3$CH$_2$NH, CH$_2$C(CH$_3$)$_2$, CH$_2$C(CH$_3$)$_2$).

Example 11

Single Step Reaction to Produce Oligomeric HALS from Caprolactam, N-hydroxyethyl-2,2,6,6-tetramethyl-4-piperidinol, and Dibutyl Carbonate.

To a 50 ml three-necked reaction flask, equipped with a magnetic stirrer and a Dean-Stark trap fitted with a condensor and nitrogen inlet/outlet, was charged 1.0 g (4.97 mmol) of N-hydroxyethyl-2,2,6,6-tetramethyl-4-piperidinol, 0.56 g (4.97 mmol) of caprolactam, 0.86 g (4.97 mmol) of dibutyl carbonate, 30 mL of toluene, and 40 mg (0.75 mmol) of sodium methoxide. The flask was immersed in an oil-bath and heated so that the solvent was distilled off over 4 hours. 20 mL of xylenes was then added to the reaction mixture and 20 mL of additional solvent distilled off over 4 hours. The resulting mixture was cooled to room temperature and diluted with dichloromethane. The organic solution was washed with water, dried (MgSO$_4$), and filtered. The solvent was then removed under reduced pressure using a rotary evaporator and further removed under vacuum (<1 mm of Hg) at 95° C. to give 1.5 g (88%) of compound VII. The structure of compound VII was confirmed by $^1$H NMR.

Example 12
Low Temperature Synthesis of Compound A.

To a 250 mL three-neck round bottom flask equipped with a magnetic stirrer, a ground glass stopper, a condenser and nitrogen inlet, and a thermometer was placed 50.33 g (558 mmol) of dimethyl carbonate and 1.04 g (19.3 mmol) of sodium methoxide. The mixture was cooled to 15° C. and 21.8 g (193 mmol) of caprolactam was added. The mixture was stirred with intermittent cooling to maintain the reaction temperature between about 9 and 18° C. for 45 minutes, then 2.4 g (40 mmol) of glacial acetic acid was added at <19° C. The mixture was dissolved in 100 mL of methylene chloride and the organic layer extracted with water, dried ($MgSO_4$), filtered, and the solvent removed under reduced pressure, followed by further removal in vacuo (<1 mm of Hg) at 95° C. 39.0 g (99%) of Compound A was recovered as a nearly colorless oil.

Example 13
Preparation of HALS Mixtures by Reaction of 2,2,6,6-tetramethyl-4-piperidinol and a Mixture of Compounds E and F A 250 mL 3-necked reaction flask was equipped with a magnetic stirrer, a thermometer adapter, and a distillation head fitted with a condenser, a receiver, and a nitrogen inlet/outlet. To this flask was charged 4.3 g (10.45 mmol) of the E/F mixture generated above, 7.27 g (46.3 mmol) of 2,2,6,6-tetramethyl-4-piperidinol, and 200 mL of xylenes. Under a slow nitrogen flow, 10 mL of xylenes were distilled off and the trap drained. After lowering the heat source and allowing the mixture to cool to 110° C., 0.17 g (0.28 mmol) of 1,3-diacetoxy-1,1,3,3-tetrabutyldistannoxane was added and the heat source raised. Another 172 mL of xylenes were slowly distilled off over 12 hours. The resulting mixture was cooled to room temperature and diluted with ethyl acetate. The organic solution was washed with water to remove excess amino alcohol and dried over molecular sieves. Filtration and removal of solvent by rotary evaporation, and further solvent removal in vacuo (<1 mm) at 95° C. gave 5.6 g (93%) of composition M-I as a yellow oil. The structure of the compounds in the mixture was verified by $^1$H NMR analysis. $^1$H NMR ($CDCl_3$): δ5.41 (br s, NH); 5.19 (m, $R_2$-C$\underline{H}$—OCOCH$_2$—); 5.06 (m, $R_2$C$\underline{H}$OCONH—); 4.62 (br s, NH); 3.22 (dt, —C$\underline{H}_2$—NH—); 3.17 (br dt, —C$\underline{H}_2$—NH—); 2.25 (t, —CH$_2$COO); 2.00–1.20 (m, C$\underline{H}_2$C(CH$_3$)$_2$, CH$_2$(C$\underline{H}_2$)$_9$CH$_2$), 1.20 (d, CH$_2$C(C$\underline{H}_3$)$_2$).

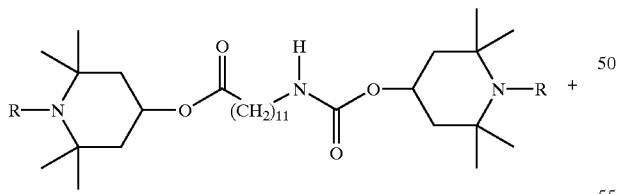

M-I(R=H)

Example 13
Preparation of HALS Mixtures by Reaction of 1,2,2,6,6-pentamethyl-4-piperidinol and a Mixture of Compounds E and F A 500 mL 3-necked reaction flask was equipped with a magnetic stirrer, a thermometer adapter, and a distillation head fitted with a condenser, a receiver, and a nitrogen inlet/outlet. To this flask was charged 7.9 g (19.2 mmol) of the E/F mixture generated above, 14.5 g (85.04 mmol) of 1,2,2,6,6-pentamethyl-4-piperidinol, and 300 mL of xylenes. Under a slow nitrogen flow, 100 mL of xylenes were distilled off and the trap drained. After lowering the heat source and allowing the mixture to cool to 100° C., 0.34 g (0.56 mmol) of 1,3-diacetoxy-1,1,3,3-tetrabutyldistannoxane was added and the heat source raised. Another 160 mL of xylenes were slowly distilled off over 10 hours. After addition of another 20 mL portion of xylenes, heating was continued for 8 hours, over which time 32 mL of xylenes were collected. The resulting mixture was cooled to room temperature and diluted with methylene chloride. The organic solution was washed with water to remove excess amino alcohol and dried over MgSO4. Filtration and removal of solvent by rotary evaporation, and further solvent removal in vacuo (<1 mm) at 95° C. gave 11.2 g (96%) of composition M-II as a yellow oil. The structure of the compounds in the mixture was verified by $^1$H NMR analysis. $^1$H NMR ($CDCl_3$): δ5.42 (br s, 1H, NH); 5.05 (m, $R_2$-C$\underline{H}$—OCOCH$_2$—); 4.94 (m, $R_2$C$\underline{H}$OCONH—); 4.65 (br s, NH); 3.22 (dt, —C$\underline{H}_2$—NH—); 3.16 (br dt, —C$\underline{H}_2$—NH—); 2.25 (t, —CH$_2$COO—); 2.23 (s, CH$_3$NC(CH$_3$)$_2$); 1.90–1.28 (m, CH$_2$(C$\underline{H}_2$)$_9$CH$_2$, C$\underline{H}_2$C(CH$_3$)$_2$), 1.10 (d, CH$_2$C(C$\underline{H}_3$)$_2$).

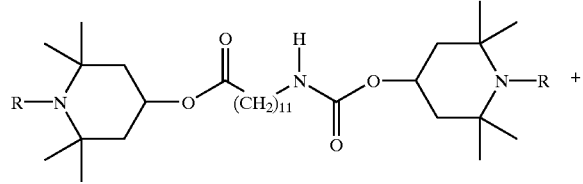

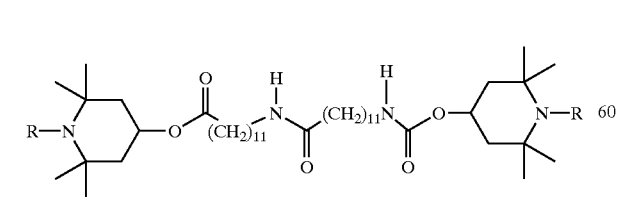

M-II(R=CH$_3$)

PERFORMANCE OF HALS COMPOUNDS ACCORDING TO THE PRESENT INVENTION

Examples 15–21
Weathering Performance of 2 k Acrylic Urethane Clear Coat Composition Containing 1,2,2,6,6-pentamethyl-4-piperidine 6-(1,2,2,6,6-pentamethyl-4-piperidinoxycarbonylamino)hexanoate (Compound II).

Compound II (1% based on total resin solids) was pre-dissolved in the solvent mixture (5–10% solids) and added to the clear 2 k acrylic urethane formulation given in Table I. The 2 k acrylic urethane is a two-component urethane formed by reacting a hydroxy functional acrylic polymer with an isocyanate cross linker. Components I and II were mixed just before use. The clear coats were applied to cold roll steel panels, measuring 4"×12" and pre-coated with an E-coat primer and white base-coat, obtained from ACT Laboratories, Inc. of Hillsdale, Mich. The draw-down technique, using WC-60 WIRE-CATORS™ available from Leneta Co. of Ho-Ho-Kus, N.J., was used to apply the clear coat to the pre-coated panels. The clear coats were allowed to flash for 10 min at ambient temperature and cured for 30 min. at 120° C.

TABLE I

Acrylic Urethane Clear Coat Formulation

| Raw Material | Amount |
| --- | --- |
| Component I | |
| JONCRYL ® CDX-588 Acrylic Resin[a] | 100 parts |
| T-12 (2% Solids in Catalyst Solution)[b] | 5 parts |
| Solvent Mixture | 45 parts |
| Compound II | 1 part[c] |
| Component II | |
| DESMODUR ® N-3390 (90% Solids)[d] | 33 parts |
| Solvent Mixture | 17 parts |
| Catalyst Solution | |
| T-12 (Dibutyltin dilaurate)[b] | 1 part |
| Acetic Acid | 4 parts |
| Propylene glycol methyl ether acetate | 45 parts |

TABLE I-continued

Acrylic Urethane Clear Coat Formulation

| Raw Material | Amount |
| --- | --- |
| Solvent Mixture: | |
| Xylenes | 1 part |
| Propylene glycol methyl ether acetate | 1 part |
| Methyl amyl ketone | 1 part |

[a]JONCRYL is commercially available from S.C. Johnson and Sons Inc. of Racine, WI.
[b]T-12 is commercially available from Air Products of Allentown, PA.
[c]1% based on total resin solids
[d]DESMODUR is commercially available from Bayer Corp. of Pittsburg, PA.

Accelerated weathering was carried out on the coatings with a QUV Accelerated Weather Tester device (commercially available from Q Panel Laboratory Products of Cleveland, Ohio) equipped with UVA-340 fluorescent bulbs and with an Atlas Ci65 WeatherOmeter ("Xenon WOM") (commercially available from Atlas Electronic Devices Co., Chicago, Ill.) equipped with Xenon arc lamps following the SAE J1960 automotive exterior test protocol. Natural weathering was carried out using 5 deg South direct weathering in South Florida. Specular properties (gloss and distinctness of image, or DOI), total color change (Delta E), and yellowing (Delta b) were measured as a function of weathering time. Specular properties were determined as described in ASTM E284 and D253. Color change and yellowing were determined as described in ASTM D2244.

The performance of Compound II under QUV weathering is summarized in Examples 15–17. The effect of Compound II on gloss retention is given in Example 15, the effect on DOI retention is given in Example 16, and the effect on delta E is given in Example 17.

Example 15

QUV Weathering (UVA-340 Bulbs) of a 2k Acrylic Urethane Clear Coat Stabilized with Compound II, Effect on Percent Gloss Retention

| | Exposure (hours) | | | | | | | | | | |
| --- | --- | --- | --- | --- | --- | --- | --- | --- | --- | --- | --- |
| Stabilizer | 1527 | 2500 | 3006 | 3508 | 4014 | 4495 | 5000 | 5500 | 6002 | 6500 | 7011 |
| None | 102 | 86 | 91.9 | 72.2 | 65.1 | 49.9 | 41.7 | 42.2 | 34.0 | 33.8 | 2.1 |
| Compound II | 102 | 96.8 | 98.7 | 99.7 | 99.6 | 98.9 | 101 | 99.3 | 100 | 99.9 | 96.2 |

A 2 k acrylic urethane clear coat stabilized with 1% of Compound II showed superior percent gloss retention compared to the 2 k urethane clear coat containing no stabilizer.

Example 16

QUV Weathering (UVA-340 Bulbs) of a 2k Acrylic Urethane Clear Coat Stabilized with Compound II, Effect on Percent DOI Retention

| | Exposure (hours) | | | | | | | | | | |
| --- | --- | --- | --- | --- | --- | --- | --- | --- | --- | --- | --- |
| Stabilizer | 1527 | 2500 | 3006 | 3508 | 4014 | 4495 | 5000 | 5500 | 6002 | 6500 | 7011 |
| None | 101 | 97.4 | 83.7 | 45.3 | 26.1 | 14 | 12.9 | 12.7 | 8.4 | 9.1 | 0.1 |
| Compound II | 102 | 101 | 101 | 102 | 106 | 106 | 107 | 107 | 107 | 107 | 107 |

A 2 k acrylic urethane clear coat stabilized with 1% of Compound II showed superior percent DOI retention compared to the a 2 k urethane clear coat containing no stabilizer.

Example 17

QUV Weathering (UVA-340 Bulbs) of a 2k Acrylic Urethane Clear Coat Stabilized with Compound II, Effect on Delta E

| Stabilizer | Exposure (hours) | | | | | |
|---|---|---|---|---|---|---|
| | 473 | 1527 | 3006 | 4014 | 5000 | 6002 |
| None | 1.19 | 1.99 | 3.29 | 3.51 | 4.01 | 4.41 |
| Compound II | 0.39 | 0.63 | 1.22 | 1.22 | 1.36 | 1.73 |

A 2 k acrylic urethane clear coat stabilized with 1% of Compound II had a superior effect on total color change (Delta E) compared to the a 2 k urethane clear coat containing no stabilizer. An increase in Delta E indicates an unfavorable discoloration of the urethane coat.

In addition to the above properties, a visual evaluation of blistering was done. After about 7011 hrs, the unstabilized coating was completely delaminated while the coating containing Compound II showed no signs of blistering.

The performance of Compound II under Xenon WOM weathering is summarized in Examples 18–20. The effect of Compound II on gloss retention is given in Example 18, the effect of Compound II on DOI retention is given in Example 19, and the effect on delta E is given in Example 20. The effect of Compound II under natural weathering (Florida) on gloss retention, yellowing (delta b), and total color change (delta E) is given in Example 21.

Example 18

Xenon Weathering (SAE J1960 Automotive Exterior) of a 2k Polyurethane Acrylic Coating Stabilized with Compound II, Effect on Percent Gloss Retention

| Stabilizer | Exposure (hours) | | | | | | | |
|---|---|---|---|---|---|---|---|---|
| | 485 | 987 | 1513 | 2011 | 2517 | 2947 | 3539 | 4039 |
| None | 97.3 | 94.5 | 95.9 | 90.6 | 76.4 | 64.2 | 47.3 | 34.5 |
| Compound II | 96.5 | 95.0 | 95.4 | 96.0 | 92.7 | 84.7 | 73.1 | 62.4 |

A 2 k acrylic urethane clear coat stabilized with 1% of Compound II showed superior gloss retention compared to the a 2 k urethane clear coat containing no stabilizer.

Example 19

Xenon Weathering (SAE J1960 Automotive Exterior) of a 2k Polyurethane Acrylic Coating Stabilized with Compound II, Effect on Percent DOI Retention

| Stabilizer | Exposure (hours) | | | | | | | | | |
|---|---|---|---|---|---|---|---|---|---|---|
| | 485 | 987 | 1513 | 2011 | 2517 | 2947 | 3539 | 4039 | 4443 | 5003 |
| None | 104 | 101 | 101 | 96.4 | 86.5 | 76.7 | 54.2 | 36.6 | 24.1 | 16.6 |
| Compound II | 101 | 102 | 101 | 101 | 100 | 99.6 | 96.0 | 93.8 | 89.0 | 75.3 |

A 2 k acrylic urethane clear coat stabilized with 1% of Compound II showed superior percent DOI retention compared to the a 2 k urethane clear coat containing no stabilizer.

Example 20

Xenon Weathering (SAE J1960 Automotive Exterior) of a 2k Polyurethane Acrylic Coating Stabilized with Compound II, Effect on Delta E

| Stabilizer | Exposure (hours) | | | | | | | | | |
|---|---|---|---|---|---|---|---|---|---|---|
| | 485 | 987 | 1513 | 2011 | 2517 | 2947 | 3539 | 4039 | 4443 | 5003 |
| None | 0.90 | 1.08 | 1.42 | 2.10 | 2.42 | 3.31 | 3.30 | 3.68 | 3.78 | 4.28 |
| Compound II | 0.42 | 0.54 | 0.51 | 1.06 | 1.08 | 2.29 | 2.24 | 2.44 | 2.41 | 2.45 |

A 2 k acrylic urethane clear coat stabilized with 1% of Compound II had a superior effect on total color change (Delta E) compared to the a 2 k urethane clear coat containing no stabilizer. An increase in Delta E indicates an unfavorable discoloration of the urethane coating.

In addition, to the above properties a visual evaluation of the degree of cracking was done after 5003 hrs. On a scale of 0 to 5, with 0 being the best, the unstabilized coating was rated 5 (severe cracking), while the coating stabilized with 1% Compound II was rated 1 (very slight cracking).

Example 21

| Florida Weathering (50° South, Direct, 18 Months) of a 2k Acrylic Urethane Clear Coat Stabilized with Compound II, Effect on Gloss Retention, Yellowing (Delta b), and Total Color Change (Delta E) | | | |
|---|---|---|---|
| Stabilizer | % Gloss | Delta b | Delta E |
| None | 93 | 0.61 | 0.73 |
| Compound II (1%) | 96 | 0.13 | 0.25 |

Under natural weathering conditions a 2 k acrylic urethane clear coat stabilized with 1% Compound II showed superior performance in gloss retention, yellowing, and total color change compared to the a 2 k urethane clear coat containing no stabilizer. An increase in Delta E indicates an unfavorable discoloration of the urethane coating. An increase in Delta b indicates an unfavorable yellowing of the urethane coating.

Example 22
Comparison of Compound II to Conventional HALS Compounds in a Polypropylene Article.

Compound III and several commercially available HALS compounds were each dry blended at a 0.25% loading level into PROFAX 6501 polypropylene powder containing 0.1% 2,4,6-tri-t-butylphenol (commercially available from Montell USA, Inc. of Wilmington, Del.). The blends were milled with a steam double roller mill at 160–170° C. for four minutes at 25 rpm. The samples were then compression molded into films at 200° C. for three minutes at a maximum pressure of 30 tons. The sample thicknesses for the exposure tests were measured for each film and fell in the range between 2.0 and 2.5 mils. The samples were exposed in a dry Xenon weatherometer and a 120° C. oven. Sample degradation was followed by measurements of the increase in the intensity of the carbonyl absorption using a Perkin-Elmer 1310 infrared spectrophotometer available from Perkin-Elmer Corp. of Norwalk, Conn. Percent carbonyl development was expressed according to the following relationship:

$$\% \text{ Carbonyl development} = (A_x - A_0)/a*1$$

where $A_0$ = absorbance at 5.85 microns less absorbance at 5.35 microns for the unexposed film $A_x$ = absorbance at 5.85 microns less absorbance at 5.35 microns for the exposed film a = 0.20 (absorptivity for "carbonyl" in polypropylene)

l = film thickness in mils

The exposure endpoint was defined as exposure hours required to reach a 0.1% carbonyl development level. The data in Table II provide a comparison of Compound II with a variety of other commercially available HALS compounds.

TABLE II

Performance of HALS compounds in PROFAX 6501 Polypropylene.

| Sample ID | HALS Compound of PROFAX 6501 Polypropylene | Dry XeWOM (hours)[a] | Oven 120° C. (days)[a] |
|---|---|---|---|
| A | CYASORB ® UV-3346[b] | 1320 | 36 |
| B | CHIMASORB ® 944[c] | 1690 | 51 |
| C | TINUVIN ® 783[c] | 987 | 51 |
| D | UVASORB ® HA-88[d] | 1900 | 51 |
| E | UV-CHEK ® AM-340[e] | >2000 | 11 |
| F | TINUVIN ® 770[c] | 1200–1600 | 7 |
| G | TINUVIN ® 765[c] | 1200–1600 | 14 |
| H | Compound II | >2000 | 11 |
| I | N/A | <400 | 9 |

[a] Average of two samples, 2.5 mils
[b] A product of Cytec Industries, Inc. of West Paterson, NJ
[c] A product of Ciba Specialty Chemicals, Inc. of Hawthorne, NY
[d] A product of 3 V Inc. of Georgetown, SC
[e] A product of Ferro Corporation of Cleveland, OH The data in Table II demonstrate that Compound II outperformed the unstabilized system and showed equal or superior performance compared to the other HALS compounds tested after 2000 hours exposure in the XeWOM.

COMPARISON OF HALS COMPOUNDS OF THE PRESENT INVENTION TO CONVENTIONAL HALS

Example 23
Performance of Compounds I–IV, VII, and VIII Relative to Conventional HALS in a PROFAX 6501 Polypropylene Article.

Compounds I–IV, VII, and VIII, as well as several commercially available HALS compounds, were each dry blended at a 0.2 percent loading level into a PROFAX 6501 polypropylene powder (commercially available from Montel USA Inc. of Wilmington, Del.) containing 0.07 percent calcium stearate (commercially available from Witco Corp. of Greenwich, Conn.), and 0.07 percent Cyanox A-2777 (commercially available from Cytec Industries of West Paterson, N.J.). Blended material was melt-mixed in a Brabender PL-2000 torque rheometer base (commercially available from C. W. Brabender Inc., South Hackensack, N.J.) equipped with a single mixing screw extruder-5 zone, single pass at 50–75 rpm, with the temperature of zones 1–5 at 210° C., 215° C., 220° C., 225° C., and 230° C., respectively. The extrudate was cooled, dried, and pelletized. Pellets were compression molded into sample plaques (2×2.5×0.100 inches) using a PHI press (commercially available from Pasadena Hydraulics Inc., The City of Industry, Calif.) at 275° C. Sample plaques were exposed in the xenon-arc weatherometer as determined by ASTM G-26 Standard using Test Method B with alternate exposure to light and darkness and intermittent exposure to water spray maintaining an atmosphere temperature of 63±3° C and a relative humidity of 30±5 percent (Miami, Fla. conditions). Color (ΔE) was determined with a Macbeth Color Eye Colorimeter (commercially available from Gretag-MacBeth LLC of New Windsor, N.Y.) under laboratory conditions with illuminate C, 2° observer, specular component excluded, and UV component included. Specular gloss was measured according to ASTM D523 Standard using a Gardner black plate 60° Glossmeter measuring deviation loss to 50 percent. Pellets were also injection-molded into tensile bars using an Arburg "Allrounder" hydraulic injection molder (commercially available from Arburg GmbH & Co. of Lossburg, Germany). Temperatures used were as follows: nozzle, 200° C.; nozzle side, 220° C.; middle, 225° C.; feed, 210° C.; and mold, 52° C. The blended material was also made into thin films. The thin films were prepared as described in Example 22.

Compounds I-IV, VII, and VIII were compared to Tinuvin 765 (bis(1,2, 2,6,6-pentamethyl-4-piperidyl) sebacate, CAS #41556-26-7) (commercially available from Ciba Specialties Corp., Hawthorne, N.Y.); Tinuvin 770 (bis(2,2,6,6-tetramethyl-4-piperidyl) sebacate, CAS #52829-07-9) (commercially available from Ciba Specialties Corp., Hawthorne, N.Y.); Tinuvin 622 (1-(2-hydroxyethyl)-4-hydroxy-2,2,6,6-tetramethyl piperidine-succininic acid, dimethyl ester, copolymer, CAS #65447-77-0) (commercially available from Ciba Specialties Corp., Hawthorne, N.Y.); Chimasorb 944 (poly[6-(1,1,3,3-tetramethylbutyl)amino]-1,3,5-triazine-2,4,-diyl]-[(2,2,6,6-tetramethyl-4-piperidyl)-imino]hexamethylene[(2,2,6,6-tetramethyl-4-piperidyl)imino], CAS #71878-19-8) (commercially available from Ciba Specialties Corp., Hawthorne, N.Y.); Tinuvin 783 (a 1:1 blend of Chimasorb 944 and Tinuvin 622) (commercially available from Ciba Specialties Corp., Hawthorne, N.Y.).

Table III shows a comparison of Hours to $\Delta E=3$ and Hours to 50% Gloss Retention for polypropylene plaques and Hours to Failure (as measured by carbonyl development in thin films) for the HALS of the invention and several commercially available HALS. Table IV shows a comparison of 50% Strength Retention, 50% Elongation Retention, and Hours to 50% Retention of Tensil Strength for the HALS of the invention and several commercially available HALS compounds in PROFAX polypropylene tensile bars.

TABLE III

Performance of HALS of the Invention Relative to Conventional HALS in PROFAX 6501 Polypropylene Plaques and, Polypropylene Thin Films.

| Contained Additive | Hours to $\Delta E = 3$ (plaques) | Hours to 50% Gloss Retention (plaques) | Hours to Failure* (thin films) |
|---|---|---|---|
| Compound VII | 2080 | 1333 | 1000 |
| Compound VIII | 1267 | 707 | 600 |
| Tinuvin 622[a] | 529 | 895 | 600 |
| None | 180 | <100 | 200 |
| Compound II | 2300 | >1600 | |
| Compound IV | >3000 | >1600 | 800 |
| Tinuvin 765[a] | 2740 | >1600 | 600 |
| None | 180 | <100 | 200 |
| Compound I | 474 | >1200 | 600 |
| Compound III | 600 | >600 | 1000 |
| Tinuvin 770[a] | 581 | >1200 | 600 |
| None | 180 | <100 | 200 |

*As measured by the increase in carbonyl absorption to a level of 0.1% as described for Example 22.
[a]A product of Ciba Specialty Chemicals, Inc. of Hawthorne, NY

TABLE IV

Performance of HALS of the Invention Relative to Conventional HALS in PROFAX 6501 Propylene Tensile Bars, Effect of Florida Weathering and Xenon Weathering.

| Contained Additive | 50% Strength Retention Months (Florida Weathering) | 50% Elongation Retention Months (Florida Weathering) | Hours to 50% Retention of Tensile Strength (Xenon Weathering) |
|---|---|---|---|
| Compound VII | >12 | 5 | |
| Compound VIII | 8 | 5 | |
| Tinuvin 622 | 7 | 5 | |
| None | <3 | <3 | |
| Compound II | | | 840 |
| Compound IV | | | 1100 |
| Tinuvin 765 | | | 640 |
| None | | | 204 |
| Compound I | | | 384 |
| Compound III | | | 690 |
| Tinuvin 770 | | | 1000 |
| None | | | 204 |

The data in Tables III and IV demonstrate that HALS of the invention outperformed the unstabilized system and showed equal or superior performance compared to the commercially available HALS compounds.

Example 24

Performance of Compounds I–IV, VII–VIII Relative to Conventional HALS in Polyethylene Articles.

Compounds I–IV and VII–VIII, as well as several commercially available HALS compounds were each dry blended at a 0.1 percent loading level into a LLDPE prills (commercially available from Equistar Chemicals LP. of Houston Tex.) containing 0.01 percent zinc stearate (commercially available from Malinckrodt Chemicals of St. Louis, Mo.), and 0.07 percent Cyanox A-2777 (commercially available from Cytec Industries of West Paterson, N.J.). Blended material was melt-mixed in a Brabender PL-2000 torque rheometer base equipped with a single mixing screw extruder-5 zone, single pass at 50–75 rpm, with the temperature of zones 1–5 at 170° C., 175° C., 180° C., 185° C., and 190°C., respectively. The extrudate was cooled, dried, and pelletized. Pellets were compression molded into sample plaques (2×2.5×0.100 inches) using a PHI press at 177° C. Sample plaques were exposed in the xenon-arc weatherometer as determined by ASTM G-26 Standard using Test Method B with alternate exposure to light and darkness and intermittent exposure to water spray maintaining an atmosphere temperature of 63±3° C. and a relative humidity of 30±5 percent (Miami, Fla. conditions). Color ($\Delta E$) was determined with a Macbeth Color Eye Colorimeter under laboratory conditions with illuminate C, 2° observer, specular component excluded, and UV component included. The blended material was also made into thin films. The thin films were prepared as described in Example 22.

Table V shows a comparison of Hours to $\Delta E=3$ and Hours to 50% Gloss Retention and Hours to Failure (as measured by carbonyl development) for the HALS of the invention and several commercially available HALS compounds in LLDPE plaques and thin films.

TABLE V

Performance of HALS of the Invention Relative to Conventional HALS in LLDPE Plaques and Thin Films.

| Contained Additive | Hours to DE = 3 (plaques) | Hours to 50% Gloss Retention (Plaques) | Hours to Failure* (Thin films) |
|---|---|---|---|
| Compound VII | 6122 | 5729 | 1000 |
| Compound VIII | 6831 | 4900 | 1800 |
| Tinuvin 622 | >7600 | 6212 | 1000 |
| None | 180 | 2467 | 200 |
| Compound II | >7600 | >7600 | 2200 |
| Compound IV | >7600 | 6850 | 1000 |
| Tinuvin 765 | >7600 | >7600 | 1000 |
| None | 180 | 2467 | 200 |
| Compound I | >7600 | 7492 | >1800 |
| Compound III | >7600 | 7446 | >1800 |
| Tinuvin 770 | 600 | 7252 | 1800 |
| None | 180 | 2467 | 200 |

*As measured by the increase in carbonyl absorption to a level of 0.1% as described for Example 22.

The data in Tables III and IV demonstrate that HALS of the invention outperformed the unstabilized system and showed equal or superior performance compared to the commercially available HALS compounds.

Example 25

Performance of Compound VIII Relative to Conventional HALS in a Polypropylene Article.

Compound VIII, 1:1 blends of Compound VIII with Cyasorb$^R$ UV-3346, Cyasorb$^R$ UV-3346, and several commercially available HALS compounds were each dry blended at a 0.2% loading level in PROFAX 6501 polypropylene flake (commercially available from Montel USA Inc. of Wilmington, Del.) containing 0.07 percent calcium stearate (commercially available from Witco Corp. of Greenwich, Conn.), and 0.07 percent Cyanox A-2777 (commercially available from Cytec Industries of West Paterson, N.J.). Blended material was melt-mixed in a Brabender PL-2000 torque rheometer base (commercially available from C. W. Brabender Inc., South Hackensack, N.J.) equipped with a single mixing screw extruder-5 zone, single pass at 50–75 rpm, with the temperature of zones 1–5 at 210° C., 215° C., 220° C., 225° C., and 230° C., respectively. The extrudate was cooled, dried, and pelletized. Pellets were compression molded into sample plaques (2×2.5×0.100 inches) using a PHI press (commercially available from Pasadena Hydraulics Inc., The City of Industry, Calif.) at 275° C. Sample plaques were exposed in the xenon-arc weatherometer as determined by ASTM G-26 Standard using Test Method B with alternate exposure to light and darkness and intermittent exposure to water spray maintaining an atmosphere temperature of 63+3° C. and a relative humidity of 30±5 percent (Miami, Fla. conditions). Specular gloss was measured according to ASTM D523 Standard using a Gardner black plate 60° Glossmeter measuring deviation loss to 50 percent.

Example 25

Performance of Compound VIII of the Invention Relative to Conventional HAtS in PROFAX 6501 Polypropylene Plaques.

| Additive | Hours to 50% Gloss Retention |
|---|---|
| Compound VIII | 2450 |
| Cyasorb UV-3346 | 2400 |
| 1:1 Cyasorb UV-3346:Compound VIII (1:1) | >2850 |
| Tinuvin 783 | 2283 |
| Tinuvin 622 | 2850 |

The data in Example 25 demonstrates that HALS of the invention showed equal or superior performance compared to commercially available HALS compounds.

Example 26

Performance of Compounds I and II Relative to Conventional HALS in Nylon 6 Plaques.

Compounds I and II and several commercially available HALS compounds were each dry blended at a 0.3% loading level into B85ZP Nylon 6 (commercially available from Honeywell Inc. of Morris Township, N.J.) containing 0.075% Cyanox A-2777 (commercially available from Cytec Industries Inc. of West Paterson, N.J.). The blended material was melt mixed in a Haake SS (commercially available from Haake Inc. (USA) of Paramus, N.J.) 0.75 inch, 25:1 single mixing screw extruder-4 zone, single pass at 70 rpm, with the temperature of zones 1–4 at 245° C., 260° C., 270° C., and 260° C., respectively. The extrudate was cooled dried and pelletized. Pellets were injection molded into sample plaques (2×2.5×0.100 inches) using an Arburg Allrounder 320-210-750 injection molding machine (commercially available from Arburg GmbH & Co. of Lossburg, Germany) with the nozzle at 245° C., nozzle side at 260° C., middle at 270° C., feed at 270° C., and mold at 82° C. Sample plaques were exposed in the xenon-arc weatherometer as determined by ASTM G-26 Standard using Test Method B with alternate exposure to light and darkness and intermittent exposure to water spray maintaining an atmosphere temperature of 63+3° C. and a relative humidity of 30±5 percent (Miami, Fla. conditions). Color as measured by yellowing index (YI) and ΔE was determined with a Macbeth Color Eye Colorimeter under laboratory conditions with illuminate C, 2° observer, specular component excluded, and UV component included.

Example 26

Performance of Compounds I and II Relative to Conventional HALS in Nylon 6 Plaques.

| Additive | YI Value after 4000 hours | Δ E value |
|---|---|---|
| UV-3346 | 6 | 8.3 |
| UV-3529 | 5.6 | 8 |
| Nylostab S-EED[a] | 3.3 | 6.8 |
| Tinuvin 770 | 3.4 | 8.3 |
| Compound 1 | 2.3 | 7.8 |
| Compound II | 2.4 | 7.3 |
| None | 8.4 | 12.3 |

[a]Nylostab S-EED is a developmental product from Clariant Corp. of Charlotte, N.C.; N,N'-bis(2,2,6,6-tetramethyl-4-piperidinyl)isophthalamide)

The data in Example 26 demonstrates that HALS of the invention outperformed the unstabilized system and showed equal or superior performance compared to the other HALS compounds.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A polymeric article comprising at least one polymeric material and a sufficient amount of at least one compound of formula I, II, or III to inhibit at least one of photo- or thermal degradation, wherein the compound of formula (I) is:

(I)

wherein n is an integer from 1 to 15, m is either 0 or 1; $R^a$, $R^b$, $R^c$, and $R^d$ are each a hydrogen or a hydrocarbyl group; Y is CO—$(CR^eR^f)_p$, wherein $R^e$ and $R^f$ are each a hydrogen or hydrocarbyl group and p is zero or an integer from 1 to 20 or CO—$C_6H_4$—, wherein the substitution pattern on the phenylene group is an ortho, meta, or para substitution pattern and one or more of the hydrogens of the phenylene group may be substituted by a hydrocarbyl group or a functional group; Z is —O— or —NG—, wherein G is H, $C_1$–$C_{12}$ alkyl or the radical R; and wherein R is

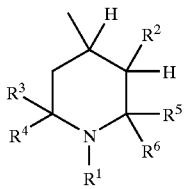

wherein $R^1$ is hydrogen, $C_1$–$C_{18}$ alkyl, O, OH, CH$_2$CN, $C_1$–$C_{18}$ alkoxy, $C_1$–$C_{18}$ hydroxyalkoxy, $C_5$–$C_{12}$ cycloalkoxy, $C_5$–$C_{12}$ hydrocycloalkoxy, $C_3$–$C_6$ alkenyl, $C_1$–$C_{18}$ alkynyl, $C_7$–$C_9$ phenylalkyl, unsubstituted or substituted on the phenyl with 1, 2 or 3 $C_1$–$C_4$ alkyls, or an aliphatic $C_1$–$C_8$ acyl; $R^2$ is hydrogen, $C_1$–$C_8$, alkyl, or benzyl; $R^3$, $R^4$, $R^5$, and $R^6$ are each a hydrogen, $C_1$–$C_8$ alkyl, benzyl or phenethyl, or two geminal R moieties, which together with the carbon to which they are attached form a $C_5$–$C_{10}$ cycloalkyl; and A is either ZR or a hydrocarbyl group; the compound of formula II is:

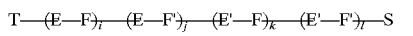
(II)

wherein i, j, k, and l are integers from about 0 to 300 and the sum of i, j, k, and l is greater than 2, wherein E—F is

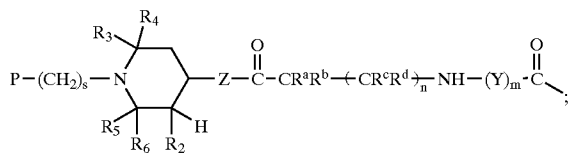

E—F' is

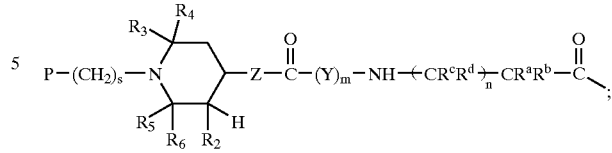

E'—F is

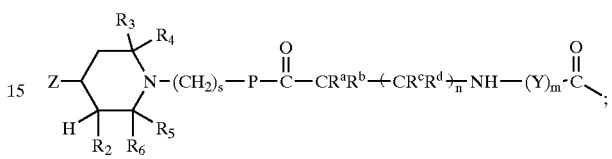

E'—F' is

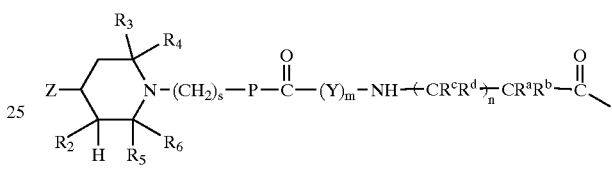

S is a hydrogen, or a unit derived from a piperidin-4-ol or a 4-aminopiperidine moiety having the structure

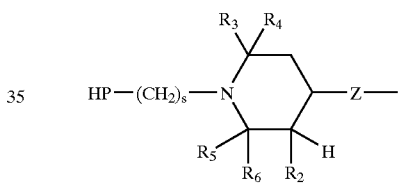

or

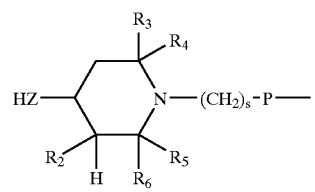

and T is a hydrogen or a unit derived from a multi-functional carbonyl compound having the structure

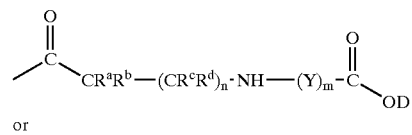

or

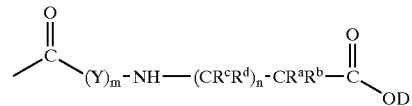

wherein D is a hydrocarbyl group, n is an integer from 1 to 15, m is either 0 or 1, s is 0 or an integer from 1 to 10; $R^a$, $R^b$, $R^c$, and $R^d$, are each a hydrogen or a hydrocarbyl group; Y is CO—$(CR^e R^f)_p$, wherein $R^e$ and $R^f$ are each a hydrogen or hydrocarbyl group and p is an integer from 0 to 20 or CO—C₆H₄—, wherein the substitution pattern on the phenylene group is an ortho, meta, or para substitution pattern, and one or more of the hydrogens of the phenylene group may be substituted by a hydrocarbyl group or a functional group; $R^2$ is hydrogen, $C_1$–$C_8$ alkyl, or benzyl; $R^3$, $R^4$, $R^5$, and $R^6$ are each a hydrogen, $C_1$–$C_8$ alkyl, benzyl or phenethyl, or two geminal R moieties, which together with the carbon to which they are attached form a $C_5$–$C_{10}$ cycloalkyl; Z is —O— or NG, wherein G is H or $C_1$–$C_{12}$ alkyl; and when s is greater than 0, P is NH or O; and when s is 0, P=O or O—L—O, where L is a hydrocarbylene; and the compound of formula III is:

  (III)

wherein i and j are integers from about 0 to 300 and the sum of i and j is greater than 2, M—F is

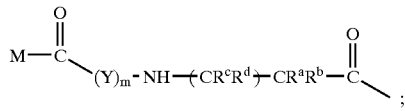

M—F' is:

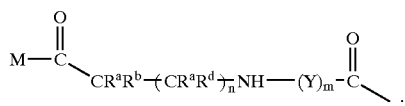

T is a hydrogen or a unit derived from a multi-functional carbonyl compound having the structure

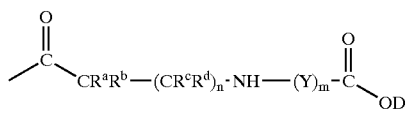

or

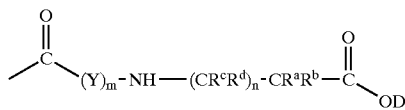

wherein D is a hydrocarbyl group, n is an integer from about 1 to 15, m is either 0 or 1, $R^a$, $R^b$, $R^c$, and $R^d$, are each a hydrogen or a hydrocarbyl group; Y is CO—$(CR^eR^f)_p$, wherein $R^e$ and $R^f$ are each a hydrogen or hydrocarbyl group and p is an integer from about 0 to 20 or CO—C₆H₄—, wherein the substitution pattern on the phenylene group is an ortho, meta, or para substitution pattern, and one or more of the hydrogens of the phenylene group may be substituted by a hydrocarbyl group or a functional group; and M is one or more diamino or a dihydroxy groups that contains a 4-aminopiperidine radical of general structure

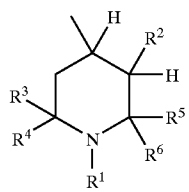

wherein $R^1$ represents hydrogen, $C_1$–$C_{18}$, alkyl, O, OH, $C_1$–$C_{18}$ alkoxy, $C_1$–$C_{18}$ hydroxyalkoxy, $C_5$–$C_{12}$ cycloalkoxy, $C_5$–$C_{12}$ hydroxycycloalkoxy, CH₂CN, $C_3$–$C_6$ alkenyl, $C_1$–$C_{18}$ alkynyl, $C_7$–$C_9$ phenylalkyl, unsubstituted or substituted on the phenyl with 1, 2 or 3 $C_1$–$C_4$ alkyls, or an aliphatic $C_1$–$C_8$ acyl; $R^2$ is hydrogen, $C_1$–$C_8$ alkyl, or benzyl; $R^3$, $R^4$, $R^5$, and $R^6$ are each a hydrogen, $C_1$–$C_8$ alkyl, benzyl or phenethyl, or two geminal R moieties, which together with the carbon to which they are attached, form a $C_5$–$C_{10}$ cycloalkyl; and M is bonded to the multi-functional carbonyl compound by the hydroxy or amino group of M.

2. The polymeric article of claim 1, wherein the amount of the at least one compound is from about 0.01 to 10 percent by weight of the polymeric article.

3. The polymeric article of claim 1, wherein the polymeric material is selected from the group consisting of polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof.

4. The polymeric article of claim 3, wherein the polymeric material comprises a polyamide or a homopolymer or copolymer of a polyolefin.

5. The polymeric article of claim 1, further comprising one or more additives selected from the group consisting of antioxidants, UV absorbers and light stabilizers, metal deactivators, phosphites and phosphonites, hydroxylamines, nitrones, thiosynergists, peroxide scavengers, polyamide stabilizers, basic co-stabilizers, nucleating agents, fillers and reinforcing agents, benzofuranones, indolinones, acid scavengers, antistatic agents, blowing agents, catalysts, clarifying agents, emulsifiers, fillers, flameproofing agents, fluorescent whitening agents, infrared absorbers, leveling assistants, lubricants, metal deactivators, mold release agents, nucleating agents, optical brighteners, pigments, plasticizers, rheological additives, and mixtures thereof.

6. The polymeric article of claim 5, wherein the one or more additives is present in an amount of up to about 10 percent by weight of the polymeric article.

7. A composition comprising
(a) at least one compound of formula I, II, or III wherein the compound of formula (I) is:

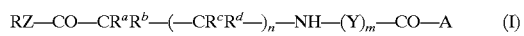  (I)

wherein n is an integer from 1 to 15, m is either 0 or 1; $R^a$, $R^b$, $R^c$, and $R^d$ are each a hydrogen or a hydrocarbyl group;

Y is CO—(CR$^e$R$^f$)$_p$, wherein R$^e$ and R$^f$ are each a hydrogen or hydrocarbyl group and p is zero or an integer from 1 to 20 or CO—C$_6$H$_4$—, wherein the substitution pattern on the phenylene group is an ortho, meta, or para substitution pattern and one or more of the hydrogens of the phenylene group may be substituted by a hydrocarbyl group or a functional group; Z is —O— or —NG—, wherein G is H, C$_1$–C$_{12}$ alkyl or the radical R; and wherein R is

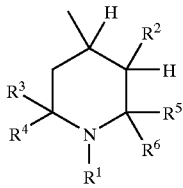

wherein R$^1$ is hydrogen, C$_1$–C$_{18}$, alkyl, O, OH, CH$_2$CN, C$_1$–C$_{18}$ alkoxy, C$_1$–C$_{18}$ hydroxyalkoxy, C$_5$–C$_{12}$ cycloalkoxy, C$_5$–C$_{12}$ hydroxycycloalkoxy, C$_3$–C$_6$ alkenyl, C$_1$–C$_{18}$ alkynyl, C$_7$–C$_9$ phenylalkyl, unsubstituted or substituted on the phenyl with 1, 2 or 3 C$_1$–C$_4$ alkyls, or an aliphatic C$_1$–C$_8$ acyl; R$^2$ is hydrogen, C$_1$–C$_8$ alkyl, or benzyl; R$^3$, R$^4$, R$^5$, and R$^6$ are each a hydrogen, C$_1$–C$_8$ alkyl, benzyl or phenethyl, or two geminal R moieties, which together with the carbon to which they are attached form a C$_5$–C$_{10}$ cycloalkyl; and A is either ZR or a hydrocarbyl group; the compound of formula II is:

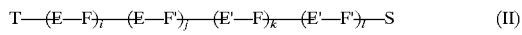

wherein i, j, k, and l are integers from about 0 to 300 and the sum of i, j, k, and l is greater than 2, wherein E—F is

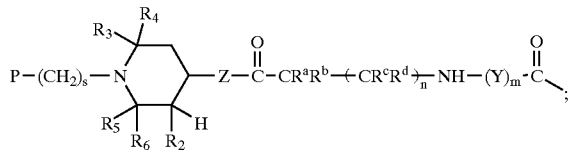

E—F' is

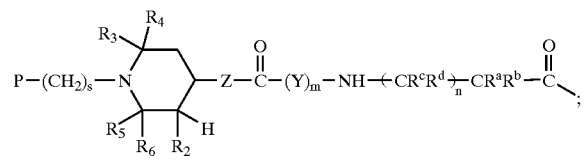

E'—F is

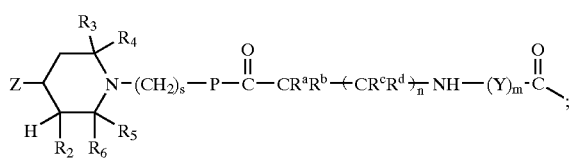

E'—F' is

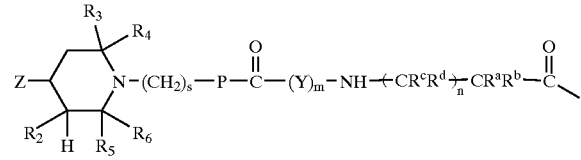

S is a hydrogen, or a unit derived from a piperidin-4-ol or a 4-aminopiperidine moiety having the structure

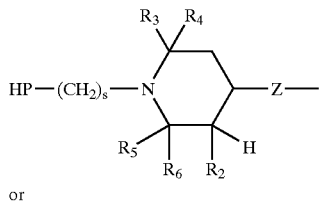

or

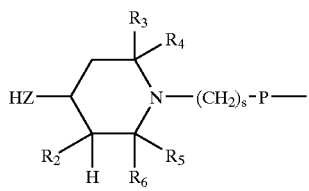

and T is a hydrogen or a unit derived from a multi-functional carbonyl compound having the structure

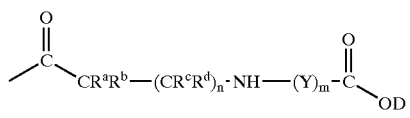

or

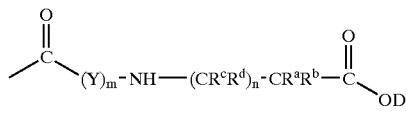

wherein D is a hydrocarbyl group, n is an integer from 1 to 15, m is either 0 or 1, s is 0 or an integer from 1 to 10; R$^a$, R$^b$, R$^c$, and R$^d$, are each a hydrogen or a hydrocarbyl group; Y is CO—(CR$^e$R$^f$)$_p$, wherein R$^e$ and R$^f$ are each a hydrogen or hydrocarbyl group and p is an integer from 0 to 20 or CO—C$_6$H$_4$—, wherein the substitution pattern on the phenylene group is an ortho, meta, or para substitution pattern, and one or more of the hydrogens of the phenylene group may be substituted by a hydrocarbyl group or a functional group; R$^2$ is hydrogen, C$_1$–C$_8$ alkyl, or benzyl; R$^3$, R$^4$, R$^5$, and R$^6$ are each a hydrogen, C$_1$–C$_8$ alkyl, benzyl or phenethyl, or two geminal R moieties, which together with the carbon to which they are attached form a C$_5$–C$_{10}$ cycloalkyl; Z is —O— or NG, wherein G is H or C$_1$–C$_{12}$ alkyl; and when s is greater than 0, P is NH or O; and when s is 0, P=O or O—L—O, where L is a hydrocarbylene; and the compound of formula III is:

wherein i and j are integers from about 0 to 300 and the sum of i and j is greater than 2, M—F is

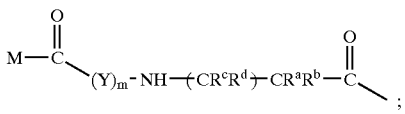

M—F' is:

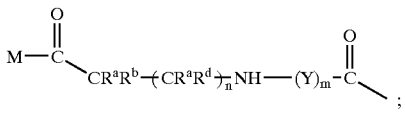

T is a hydrogen or a unit derived from a multi-functional carbonyl compound having the structure

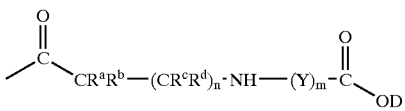

or

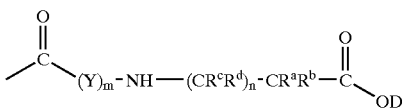

wherein D is a hydrocarbyl group, n is an integer from about 1 to 15, m is either 0 or 1, $R^a$, $R^b$, $R^c$, and $R^d$, are each a hydrogen or a hydrocarbyl group; Y is CO—$(CR^eR^f)_p$, wherein $R^e$ and $R^f$ are each a hydrogen or hydrocarbyl group and p is an integer from about 0 to 20 or CO—$C_6H_4$—, wherein the substitution pattern on the phenylene group is an ortho, meta, or para substitution pattern, and one or more of the hydrogens of the phenylene group may be substituted by a hydrocarbyl group or a functional group; and M is one or more diamino or a dihydroxy groups that contains a 4-aminopiperidine radical of general structure

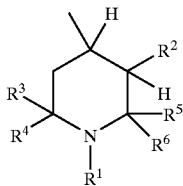

wherein $R^1$ represents hydrogen, $C_1$–$C_{18}$ alkyl, O, OH, $C_1$–$C_{18}$ alkoxy, $C_1$–$C_{18}$ hydroxyalkoxy, $C_5$–$C_{12}$ cycloalkoxy, $C_5$–$C_{12}$ hydroxycycloalkoxy, $CH_2CN$, $C_3$–$C_6$ alkenyl, $C_1$–$C_{18}$ alkynyl, $C_7$–$C_9$ phenylalkyl, unsubstituted or substituted on the phenyl with 1, 2 or 3 $C_1$–$C_4$ alkyls, or an aliphatic $C_1$–$C_8$ acyl; $R^2$ is hydrogen, $C_1$–$C_8$ alkyl, or benzyl; $R^3$, $R^4$, $R^5$, and $R^6$ are each a hydrogen, $C_1$–$C_8$ alkyl, benzyl or phenethyl, or two geminal R moieties, which together with the carbon to which they are attached, form a $C_5$–$C_{10}$ cycloalkyl; and M is bonded to the multi-functional carbonyl compound by the hydroxy or amino group of M;

(b) at least one other additive selected from the group consisting of: UV-absorbers and light stabilizers, and antioxidants.

8. The composition of claim 7 wherein said at least one other additive is selected from the group consisting of 2-(2'-hydroxyphenyl)benzotriazoles, oxamides, 2-(2-hydroxphenyl)-1,3,5-triazines, 2-hydroxybenzophenones, sterically hindered amines and hindered phenol antioxidants.

9. The composition of claim 7 wherein said at least one additive is selected from the group consisting of: 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(a,a-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl) phenylbenzotriazole; 2,2-methylenebis[4-(1,1,3,3-tetramethylbutyl)-6-benzotriazol-2-ylphenol], the transesterification product of 2-[3'-tert-butyl-5'-(2-methoxycarbonylethyl)-2'-hydroxyphenyl]benzotriazole with polyethylene glycol 300; [R—CH2CH—COO(CH2) 3]2 B where R=3'-tert-butyl-4'-hydroxy-5'-2H-benzotriazol-2-ylphenyl; bis(2,2,6,6-tetramethylpiperidin-4-yl) sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2, 6,6-tetramethylpiperidine; bis(1,2,2,6,6-pentamethyl-piperidyl)-2-n-butyl-2-(2-hydroxy-3,5-di-tert-butylbenzyl) malonate; 3-n-octyl-7,7,9,9-tetramethyl-1,3,8-triazaspiro [4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis (2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2, 6,6-tetramethylpiperidine; the condensate of N,N'-bis(2,2,6 6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro- 1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines and the reaction product of 7,7,9,9-tetramethyl-2-cycloundecyl-1-oxa-3,8-diaza-4-oxospiro[4.5]decane and epichlorohydrin; 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3, 5-triazine; 2-[2-hydroxy-4-(2-hydroxy-3-octyloxypropyloxy)-phenyl]-4,6-bis(2,4-dimethylphenyl)-1,3, 5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; 2-(2-hydroxyphenyl)-4-(4-methoxyphenyl)-6-phenyl-1,3,5-triazine, 2,4-dihydroxybenzophenone; 2-hydroxy-4-methoxybenzophenone; 2-hydroxy-4-octyloxybenzophenone; 2-hydroxy-4-decyloxybenzophenone; 2-hydroxy-4-dodecyloxybenzophenone; 2-hydroxy-4-benzyloxybenzophenone, 4,2',4-trishydroxybenzophenone; 2'-hydroxy-4,4'-dimethoxybenzophenone; 1,3,5-tris(2,6-dimethyl-4-tert-butyl-3hydroxybenzyl)isocyanurate; 1,3,5-tris(3,5-di-tert-butyl-4-hydroxybenzyl)isocyanurate; 1,3,5-tris(3,5-di-tert-butyl-4-hydroxybenzyl)-2,4,6-trimethylbenzene; 2,6-di-tert-butyl-4-methylphenol; 2,2'-ethylidene-bis(4,6-di-tert-butylphenol); 1,1,3-tris(5-tert-butyl-4-hydroxy-2-methylphenyl)butane; esters of b-(3,5-di-tert-butyl-4-hydroxyphenyl)propionic acid with mono- or polyhydric alcohols; esters of b-(5-tert-butyl-4-hydroxy-3-methylphenyl)propionic acid with mono- or polyhydric alcohols; dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxy- benzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid; amides of b-(3,5-di-tert-butyl-4-hydroxyphenyl)propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl)trimethylenediamine; and N,N'-bis(3,5-di-tert-butyl-4-hydroxyphenylpropionyl)hydrazine.

10. The composition of claim 9 wherein said at least one compond is the compound of formula I.

11. The composition of claim 9 wherein said at least one compound is the compound of formula II.

12. The composition of claim 9 wherein said at least one compound is the compound of formula III.

13. The composition of claim 7 further comprising a material to be stabilized, said material selected from the group consisting of: polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, styrene acrylonitrile, acrylate styrene acrylonitrile, cellulosic acetate butyrate, cellulosic polymers, polyimides, polyamideimides, polyetherimides, polyphenylsulfides, polyphenylene oxide, polysulfones, polyethersulfones, polyvinylchlorides, polycarbonates, polyketones, aliphatic polyketones, thermoplastic TPO's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and mixtures thereof.

* * * * *